(12) United States Patent
Fahmy et al.

(10) Patent No.: US 12,156,939 B2
(45) Date of Patent: *Dec. 3, 2024

(54) NANOLIPOGEL VEHICLES FOR CONTROLLED DELIVERY OF DIFFERENT PHARMACEUTICAL AGENTS

(71) Applicant: YALE UNIVERSITY, New Haven, CT (US)

(72) Inventors: Tarek M. Fahmy, New Haven, CT (US); Eric Stern, Jamaica Plain, MA (US); Richard A. Flavell, Guillford, CT (US); Jason Park, New York, NY (US); Alyssa Siefert, Naugatuck, CT (US); Stephen H. Wrzesinski, Slingerlands, NY (US)

(73) Assignee: Yale University, New Haven, CT (US)

( * ) Notice: Subject to any disclaimer, the term of this patent is extended or adjusted under 35 U.S.C. 154(b) by 516 days.

This patent is subject to a terminal disclaimer.

(21) Appl. No.: 17/399,544

(22) Filed: Aug. 11, 2021

(65) Prior Publication Data
US 2022/0031617 A1    Feb. 3, 2022

Related U.S. Application Data

(63) Continuation of application No. 16/711,591, filed on Dec. 12, 2019, now Pat. No. 11,173,119, which is a (Continued)

(51) Int. Cl.
*A61K 9/127* (2006.01)
*A61K 9/00* (2006.01)
(Continued)

(52) U.S. Cl.
CPC ............ *A61K 9/127* (2013.01); *A61K 9/0019* (2013.01); *A61K 9/1271* (2013.01); (Continued)

(58) Field of Classification Search
CPC .............................. A61K 9/127; A61K 9/1271
See application file for complete search history.

(56) References Cited

U.S. PATENT DOCUMENTS

| 5,120,727 A | 6/1992 | Kao |
| 5,128,355 A | 7/1992 | Carini |
(Continued)

FOREIGN PATENT DOCUMENTS

| EP | 2177230 A1 | 4/2010 |
| EP | 2389928 A2 | 11/2011 |
(Continued)

OTHER PUBLICATIONS

Murphy et al., Targeted Nanogels: A Versatile Platform for Drug Delivery, Mol. Can. Ther., 10(8) (Year: 2011).*

(Continued)

*Primary Examiner* — Carlos A Azpuru
(74) *Attorney, Agent, or Firm* — Riverside Law LLP

(57) ABSTRACT

A "nanolipogel" is a delivery vehicle including one or more lipid layer surrounding a hydrogel core, which may include an absorbent such as a cyclodextrin or ion-exchange resin. Nanolipogels can be constructed so as to incorporate a variety of different chemical entities that can subsequently be released in a controlled fashion. These different incorporated chemical entities can differ dramatically with respect to size and composition. Nanolipogels have been constructed to contain co-encapsulated proteins as well as small hydrophobic drugs within the interior of the lipid bilayer. Agents incorporated within nanolipogels can be released into the milieu in a controlled fashion, for example, nanolipogels provide a means of achieving simultaneous sustained release of agents that differ widely in chemical composition and molecular weight. Additionally, nanolipogels can favorably modulate biodistribution.

13 Claims, 23 Drawing Sheets

Related U.S. Application Data continuation of application No. 15/923,139, filed on Mar. 16, 2018, now Pat. No. 10,603,276, which is a continuation of application No. 15/155,055, filed on May 15, 2016, now Pat. No. 10,034,917, which is a continuation-in-part of application No. 14/394,161, filed as application No. PCT/US2013/036487 on Apr. 12, 2013, now Pat. No. 9,610,250.

(60) Provisional application No. 61/747,614, filed on Dec. 31, 2012, provisional application No. 61/747,624, filed on Dec. 31, 2012, provisional application No. 61/623,486, filed on Apr. 12, 2012.

(51) Int. Cl.

| | |
|---|---|
| A61K 9/51 | (2006.01) |
| A61K 31/343 | (2006.01) |
| A61K 38/18 | (2006.01) |
| A61K 38/20 | (2006.01) |
| A61K 47/24 | (2006.01) |
| A61K 47/40 | (2006.01) |
| A61K 47/58 | (2017.01) |
| A61K 47/68 | (2017.01) |
| A61K 47/69 | (2017.01) |
| B82Y 5/00 | (2011.01) |
| C07K 16/28 | (2006.01) |

(52) U.S. Cl.
CPC .......... *A61K 9/1273* (2013.01); *A61K 9/1277* (2013.01); *A61K 9/5153* (2013.01); *A61K 31/343* (2013.01); *A61K 38/1841* (2013.01); *A61K 38/2013* (2013.01); *A61K 47/24* (2013.01); *A61K 47/40* (2013.01); *A61K 47/58* (2017.08); *A61K 47/6849* (2017.08); *A61K 47/6937* (2017.08); *A61K 47/6951* (2017.08); *B82Y 5/00* (2013.01); *C07K 16/2812* (2013.01)

(56) References Cited

U.S. PATENT DOCUMENTS

| | | | |
|---|---|---|---|
| 5,138,069 | A | 8/1992 | Carini |
| 5,153,197 | A | 10/1992 | Carini |
| 5,155,118 | A | 10/1992 | Carini |
| 5,162,333 | A | 11/1992 | Failli |
| 5,202,332 | A | 4/1993 | Hughes |
| 5,210,079 | A | 5/1993 | Carini |
| 5,354,867 | A | 10/1994 | Carini |
| 5,385,908 | A | 1/1995 | Nelson |
| 5,484,790 | A | 1/1996 | Failli |
| 5,530,006 | A | 6/1996 | Waranis |
| 5,559,112 | A | 9/1996 | Skotnicki |
| 5,567,709 | A | 10/1996 | Skotnicki |
| 5,780,462 | A | 7/1998 | Lee |
| 5,989,591 | A | 11/1999 | Nagi |
| 6,015,809 | A | 1/2000 | Zhu |
| 7,052,694 | B2 | 5/2006 | Pease |
| 7,390,888 | B2 | 6/2008 | Pease |
| 7,411,051 | B2 | 8/2008 | Rosen |
| 8,114,845 | B2 | 2/2012 | Langermann |
| 8,263,125 | B2 | 9/2012 | Vaya |
| 8,609,089 | B2 | 12/2013 | Langermann |
| 8,709,416 | B2 | 4/2014 | Langermann |
| 9,603,800 | B2 | 3/2017 | Fahmy |
| 9,610,250 | B2 * | 4/2017 | Fahmy .............. A61K 9/1277 |
| 10,603,276 | B2 * | 3/2020 | Fahmy .................. B82Y 5/00 |
| 11,173,119 | B2 * | 11/2021 | Fahmy .................. A61K 47/58 |
| 2003/0035842 | A1 | 2/2003 | Kazakov |
| 2004/0071761 | A1 | 4/2004 | Miller |
| 2006/0099203 | A1 | 5/2006 | Pease |
| 2006/0110383 | A1 | 5/2006 | Honjo |
| 2007/0014845 | A1 | 1/2007 | Zhang |
| 2007/0166281 | A1 | 7/2007 | Kosak |
| 2007/0168281 | A1 | 7/2007 | Kosak |
| 2007/0219122 | A1 | 9/2007 | Glazer |
| 2008/0050920 | A1 | 2/2008 | Kawahara |
| 2008/0187595 | A1 | 8/2008 | Jordan |
| 2009/0004213 | A1 | 1/2009 | Singh |
| 2011/0262406 | A1 | 10/2011 | Del |
| 2014/0343865 | A1 | 11/2014 | Brown |
| 2015/0064265 | A1 | 3/2015 | Fahmy |
| 2015/0118318 | A1 | 4/2015 | Fahmy |

FOREIGN PATENT DOCUMENTS

| | | |
|---|---|---|
| EP | 2494960 A1 | 9/2012 |
| JP | 2015505965 | 2/2015 |
| WO | 9504738 A1 | 2/1995 |
| WO | 9515746 A1 | 6/1995 |
| WO | 9516691 A1 | 6/1995 |
| WO | 9522972 A1 | 8/1995 |
| WO | 0001385 A1 | 1/2000 |
| WO | 03099196 A2 | 12/2003 |
| WO | 2004004771 A1 | 1/2004 |
| WO | 2004056875 A1 | 7/2004 |
| WO | 2006121168 A1 | 11/2006 |
| WO | 2006133396 A2 | 12/2006 |
| WO | 2007005754 A2 | 1/2007 |
| WO | 2007005874 A2 | 1/2007 |
| WO | 2007056539 A2 | 5/2007 |
| WO | 2007072286 A2 | 6/2007 |
| WO | 2008083174 A2 | 7/2008 |
| WO | 2009014708 A2 | 1/2009 |
| WO | 2009073533 A2 | 6/2009 |
| WO | 2010083337 A2 | 7/2010 |
| WO | 2011050710 A1 | 5/2011 |
| WO | 2012009611 A2 | 1/2012 |
| WO | 2012068531 A2 | 5/2012 |
| WO | 2015066535 A1 | 5/2015 |

OTHER PUBLICATIONS

Altincicek, et al., 'Identification of collagen IV derived danger/alarm signals in insect immunity by nanoLC-FTICR MS', 2009, Biol Chem., 390:1303-11.

Anderson and Shive, et al., "Biodegradation and biocompatibility of PLA and PLGA microspheres," 1997, Adv Drug Deliv Rev 28(1):5-24.

Argyo, et al., "Multifunctional Mesoporous Silica Nanoparticles as a Universal Platform for Drug Delivery", 2014, Chem. Mater., 26(1):435-451.

Aubert, et al., "Antigen-specific CD4 T-cell help rescues exhausted CD8 T cells during chronic viral infection," 2011, PNAS, 108:21182-7.

Barbe, et al., "Silica Particles: A Novel Drug-Delivery System," 2004, Advanced Materials, 16(21):1959-66.

Berger et al., "Phase I safety and pharmacokinetic study of CT-011, a humanized antibody interacting with PD-1, in patients with advanced hematologic malignancies," 2008, Clin. Cancer Res., 14:3044-51.

Blanco, et al., "Induction of dendritic cell differentiation by IFN-alpha in systemic lupus erythematosus," 2001, Science 294(5546)1540-3.

Blanco, et al., "Nanomedicine in cancer therapy: innovative trends and prospects," 2011, Cancer Sci, 102(7):1247-52.

Bonifaz, et al., 'Efficient targeting of protein antigen to the dendritic cell receptor DEC-205 in the steady state leads to antigen presentation on major histocompatibility complex class I products and peripheral CD8+ T cell tolerance', J. Exp. Med., 196(12)1627-38 (2002).

Bonifaz, et al., "In vivo targeting of antigens to maturing dendritic cells via the DEC-205 receptor improves T cell vaccination," 2004, J. Exp. Med., 199(6):815-24.

Braumuller, et al., "T-helper-1-cell cytokines drive cancer into senescence," 2012, Nature, 494:361-365.

(56) References Cited

OTHER PUBLICATIONS

Butte, et al., "Programmed death-1 ligand 1 interacts specifically with the B7-1 costimulatory molecule to inhibit T cell responses", Immunity, vol. 27, pp. 111-122, (2007).
Capurso, et al., 'Development of a nanoparticulate formulation of retinoic acid that suppresses Th17 cells and upregulates regulatory T cells', Self Nonself, 1:4:335-40 (2010).
Cavalli, et al., 'Solid lipid nanoparticies as carriers of hydrocortisone and progesterone complexes with beta-cyclodextrins', Intl J Pharma., 182:59-69 (1999).
Chen, et al. 'Evaluation of ion-exchange microspheres as carriers for the anticancer drug doxorubicin: in vitro studies.' J. Pharm. Pharmacol. 44(3):211-5 (1992).
Chen, et al., 'A facile construction strategy of stable lipid nanoparticles for drug delivery using a hydrogel-thickened microemulsion system', 2010, Nanotechnology 21:015101.
Clarke, et al., 'Cancer stem cells—perspectives on current status and future directions: AACR Workshop on cancer stem cells', Cancer Res., 66:9339-9344 (2006).
Clawson, et al., 'Synthesis and characterization of lipid-polymer hybrid nanoparticles with pH-triggered PeG shedding', Langmuir, 27(17):10556-61 (2011).
Corradetti, et al., "Paracrine signaling events in embryonic stem cell renewal mediated by affinity targeted nanoparticles", Biomaterials, 33(28):6634-43 (2012).
Corrected Notice of Allowability dated May 22, 2020 for U.S. Appl. No. 16/238,683 (pp. 1-2).
Corthay, et al., "Primary antitumor immune response mediated by CD4+ T cells", Immunity, 22, 371-83 (2005).
Cubillos-Ruiz, et al., "Polyethylenimine-based siRNA nanocomplexes reprogram tumor-associated dendritic cells via TLR5 to elicit therapeutic antitumor immunity", J. Clin. Invest. 119(8): 2231-44 (2009).
Curiel, 'Regulatory T cells and treatment of cancer', Curr. Opin. Immunol., 20(2):241-6 (2008).
Dacosta, et al., 'SB-505124 is a selective inhibitor of transforming growth factor-beta type I receptors ALK4, ALK5, and ALK7', Mol Pharmacol. 65:744-52 (2004).
Dalerba, et al., 'Cancer stem cells: models and concepts', Annu. Rev. Med., 58:267-84 (2007).
Danhier, et al., 'PLGA-based nanoparticles: an overview of biomedical applications', J. Control Release, 161(2):505-22 (2012).
De Miguel, et al., "Proofs of the structure of lipid coated nanoparticles (SMBV) used as drug carriers", Pharma Res., 17(7):817-24 (2000).
De Rezende, et al., 'Regulatory T cell as a target for cancer therapy', Arch. Immunol. Ther. Exp., 58(3):179-90 (2010).
Demento, et al., 'Inflammasome-activating nanoparticles as modular systems for optimizing vaccine efficacy', Vaccine, 27(23):3013-21 (2009).
Demento, et al., "Role of sustained antigen release from nanoparticle vaccines in shaping the T cell memory phenotype", Biomaterials, 33(19):4957-64 (2012).
Diop-Frimpong, et al., 'Losartan inhibits collagen I synthesis and improves the distribution and efficacy of nanotherapeutics in tumors', PNAS, 108(7):2909-14 (2011).
Egilmez et al., "Cytokine immunotherapy of cancer with controlled release biodegradable microspheres in a human tumor xenograft/SCID mouse model," 1998, Cancer Immunol. Immunother. 46:21-24.
Elamanchili, et al., 'Characterization of poly(D,L-lactic-co-glycolic acid) based nanoparticulate system for enhanced delivery of antigens to dendritic cells', Vaccine, 22(19):2406-12 (2004).
Elbarbry, et al., 'Liquid chromatographic determination of mycophenolic acid and its metabolites in human kidney transplant plasma: pharmacokinetic application', J Chromatogr B Analyt Technol Biomed Life Sci, 859(2):276-81(2007).
Erbe, et al., 'Small molecule ligands define a binding site on the immune regulatory protein B7.1.', J. Biol. Chem., 277:7363-8 (2002).
Fahmy, et al., 'Targeted for drug delivery', Materials Today, 8(8):18-26 (2005).

Farag, et al. 'Rate of release of organic carboxylic acids from ion exchange resins' J. Pharm. Sci. 77(10):872-5(1988).
Filler, et al., 'Random pharmacokinetic profiles of EC-MPS in children with autoimmune disease', Pediatric Rheumatol., 8:1 (2010), 5 pages.
Flavell, et al., The polarization of immune cells in the tumour enviroment by TGFbeta, Nat Rev Immunol., 10(8):1-27 (2010).
Freeman, "Structures of PD-1 with its ligands: sideways and dancing cheek to cheek", PNAS, 105:10275-6 (2008).
Frey, et al., 'Signaling defects in anti-tumor T cells', Immunol. Rev., 222:192-205 (2008).
Ginzler, et al., 'Mycophenolate mofetil or intravenous cyclophosphamide for lupus nephritis', N Engl J Med, 353(21):2219-28 (2005).
Gorelik, et al., 'Immune-mediated eradication of tumors through the blockade of transforming growth factor-beta signaling in T cells', Nat Med., 7(10):1118-22 (2001).
Grell, et al., 'The transmembrane form of tumor necrosis factor is the prime activating ligand of the 80 kDa tumor necrosis factor receptor', Cell, 83:793-802 (1995).
Guo, et al., 'Losartan downregulates the expression of transforming growth factor beta type I and type II receptors in kidney of diabetic rat.', Zhonghua Nei Ke Za Zhi, 42:403-8 (2003).
Hamidi, et al., 'Hydrogel nanoparticles in drug delivery', Adv Drug Deily Rev., 60(15):1638-49 (2008).
Hawiger, et al., "Dendritic cells induce peripheral T cell unresponsiveness under steady state conditions in vivo", J. Exp. Med., 194(6):769-79 (2001).
Health Day, 'Blood pressure drug might boost chemo success, mouse study suggests', http://consumer.healthday.com/circulatory-system-information-7/blood-pres- sure-news-70/blood-pressure-drug-might-boost-chemo-success-mouse-study-sug-gests-680633.html, Retrieved from the internet Oct. 2, 2013. (1 page).
Hoare, et al., 'Hydrogels in drug delivery: Process and challenges', Polymer, 49:1993-2007 (2008).
Honeychurch, et al., 'Anti-CD40 monoclonal antibody therapy in combination with irradiation results in a CD8 T-cell-dependent immunity to B-cell lymphoma', Blood, 102:1449-1457 (2003).
Hong, 'Lipid-hydrogel nanoparticles synthesis methods and characterization', Theses from DRUM, pp. 1-91 (2009).
Hu, et al., "Reaction parameters of targeted gene repair in mammalian cells", Mol. Biotech., 29:197-210 (2005).
Hunder, et al., 'Treatment of metastatic melanoma with autologous CD4+ T cells against NY-ESO-1', NEJM, 358:2698-2703 (2008).
Jain, et al., "Nanolipobeads bases drug delivery system for effective management of peptic ulcer", Intl J Curr Pharmaceutical Res., 3(2):141-9 (2011).
Jhunjhunwala, et al., 'Controlled release formulations of IL-2, TGF-21 and rapamycin for the induction of regulatory T cells', J Cont Rel., 159(1):78-84 (2012).
Jonsson, et al., 'Inosine monophosphate dehydrogenase (IMPDH) inhibition in vitro suppresses lymphocyte proliferation and the production of immunoglobulins, autoantibodies and cytokines in splenocytes from MRLIpr/Ipr mice', Clin Exp Immunol, 124(3):486-91 (2001).
Jonsson, et al., "Mycophenolic acid inhibits inosine 5'-monophosphate dehydrogenase and suppresses immunoglobulin and cytokine production of B cells", Int Immunopharmacol, 3(1):31-7 (2003).
Joshi, et al., 'Targeting tumor antigens to dendritic cells using particulate carriers', J. Control Release, 161(1):25-37 (2012).
Kahn, 'CD4+ T cell clones specific for the human p97 melanoma-associated antigen can eradicate pulmonary metastases from a murine tumor expressing the p97 antigen', J Immunol, 146:3235-41 (1991).
Karnell, et al., "Mycophenolic acid differentially impacts B cell function depending on the stage of differentiation", J Immunol, 187(7):3603-12 (2011).
Kazakov and Levon, "Liposome-nanogel structures for future pharmaceutical applications," 2006, Curr Pharm Des 12:4713-28.
Khalil, et al., "Angiotensin II type 1 receptor antagonist (losarian) down-regulates transforming growth factor-beta in experimental acute pyelonephritis," 2000, J Urology, 164(1):186-91.
Kong, et al., 'Combination therapy with losartan and piog; otazone additively reduces renal oxidative and nitrative stress induced by

(56) References Cited

OTHER PUBLICATIONS chronic high fat, sucrose, and sodium intake', Oxid Med Cell. Longev, doi: 10.1155/2012/856085 (2012). (10 pages).
Lagaraine, et al., 'Induction of human CD4+ regulatory T cells by mycophenolic acid-treated dendritic cells', J Leukoc Biol, 84(4):1057-64 (2008).
Lagaraine, et al., 'Mycophenolic acid-treated human dendritic cells have a mature migratory phenotype and inhibit allogeneic responses via direct and indirect pathways', Int Immunol, 17(4):351-63 (2005).
Lazar-Molnar, et al., 'Crystal structure of the complex between programmed death-1 (PD-1) and its ligand PD-L2', PNAS, 105:10483-8 (2008).
Lee et al., "Amphiphilic poly(D,L-lactic acid)/poly(ethylene glycol)/poly(D,L-lactic acid) nanogels for controlled release of hydrophobic drugs," 2006, 6(10):846-54.
Lee, et al., "Induction and maintenance therapy for lupus nephritis: a systematic review and meta-analysis", Lupus, 19(6):703-10 (2010).
Lipsky, 'Mycophenolate mofetil', Lancet, 348:L1357-9 (1996).
Look, et al., 'Application of nanotechnologies for improved immune response against infectious diseases in the developing world', Adv Drug Deilv Rev, 62(4-5):378-93 (2010).
Look, et al., 'Nanogel-based delivery of mycophenolic acid ameliorates systemic lupus erythematosus in mice', J. Clin Invest., 123(4):1741-9 (2013).
Look, et al., 'The nanomaterial-dependent modulation of dendritic cells and its potential influence on therapeutic immunosuppression in lupus', Biomaterials, 35(3):1089-95 (2014).
Losartan, from Wikipedia encyclopedia, https://en.wikipedia.org/wiki/Losartan, 4 pages, retrieved from the internet Oct. 22, 2013.
Luchini, et al. 'Smart hydrogel nanoparticles for serum cancer biomarkers harvesting', AACR annual meeting, Apr. 14-18, Los Angles CA, 2007. (1 page).
Lui, et al., 'Effect of mycophenolate mofetil on severity of nephritis and nitric oxide production in lupus-prone MRL/Ipr mice', Lupus, 11 (7):411-8 (2002).
Lund, et al., 'Toll-like receptor 9-mediated recognition of Herpes simplex virus-2 by plasmacytoid dendritic cells', J Exp Med, 198(3):513-20 (2003).
Ma et al., 'The comparison of different daidzein-PLGA nanoparticles in increasing its oral bioavailability', Int J Nanomed., 7:559-570 (2012).
Matreya, '1,2-Distearoylphosphatidylethanolamine-methyl-polyethyleneglycol conjugate-200(Na +salt)', http://www.matreya.com/ProductInfo.aspx?peoductid=1439, 2 pages, retrieved from the Internet Mar. 30, 2012. (2 pages).
Maurer, et al., 'Developments in liposomal drug delivery systems', Expert Opin Biol Ther., 1(6):923-47 (2001).
Mehling, et al., Mycophenolate mofetil impairs the maturation and function of murine dendritic cells, J Immunol, 165(5):2374-81 (2000).
Monneaux, et al., 'Molecular therapies for systemic lupus erythematosus: clinical trials and future prospects', Arthritis Res Ther, 11(3):234 (2009).
Moroni, et al., 'A randomized pilot trial comparing cyclosporine and azathioprine for maintenance therapy in diffuse lupus nephritis over four years', Olin J Am Soc Nephrol, 1(5):925-32 (2006).
Mougiakakos, et al., 'Regulatory T cells in cancer', Adv Cancer Res, 107:57-117 (2010).
Moya-Ortega et al., "Cyclodextrin-based nanogels for pharmaceutical and biomedical applications," 2012, Int J Pharm 428:152-63.
Mura, et al., "Development of a new delivery system consisting of drug-in cyclodextrin-in PLGA nanoparticles", J Microencapsulation, 27(6):479-86 (2010).
Murphy, et al., "Targeted Nanogels: A Versatile Platform for Drug Delivery to Tumors", Mole Cancer Therapeutics, 10(6):972-82 (2011).
Nagaraj, et al., 'Anti-inflammatory triterpenoid blocks immune suppressive function of MDSCs and improves immune response in cancer', Clin Cancer Res., 16(6):1812-23 (2010).
Navarra, et al., 'Efficacy and safety of belimumab in patients with active systemic lupus erythematosus: a randomised, placebo-controlled, phase 3 trial', Lancet, 377(9767):721-31 (2011).
Nesbeth, et al., 'CD4+ T cells elicit host immune responses to MHC class II-negative ovarian cancer through CCL5 secretion and CD40-mediated licensing of dendritic cells' , J Immunol., 184:5654-62 (2010).
Notice of Allowance dated Jul. 21, 2021 for U.S. Appl. No. 16/711,591 (pp. 1-8).
Oda, et al., 'Transforming growth factor $^2$ (TGF-$^2$) and regulatory T cells (Treg): The interface of tumor and host immunity,' European journal of clinical & medical oncology 4(1):27-32 (2011).
Office Action dated Dec. 14, 2020 for U.S. Appl. No. 16/711,591 (pp. 1-8).
Office Action dated Mar. 30, 2021 for U.S. Appl. No. 16/711,591 (pp. 1-5).
Office Action dated Sep. 3, 2020 for U.S. Appl. No. 16/711,591 (pp. 1-9).
Olsen, et al., 'Genomic sequence correction by single-stranded DNA oligonucleotides: role of DNA synthesis and chemical modifications of the oligonucleotide ends'. J. Gene Med., 7:1534-44 (2005).
Opal and DePalo, 'Anti-inflammatory cytokines', Chest, 117(4):1162-72 (2000).
Park, 'Rationally engineered nanoparticles for therapeutic modulation of transforming growth factor beta signaling', Dissertation confidentially presented May 2011, not publically available other than abstract from ProQuest UMI No. 3467563, pp. 1-25 only distributed to one party prior to filing of U.S. Appl. No. 61/623,486, filed Apr. 12, 2012.
Park, et al., "Combination delivery TGF-2 inhibitor and IL-2 nanoscale liposomal polymeric gels enhances tumor immunotherapy," 2012, Nat Mater., 11(20):895-905.
Patel, et al., 'Review on hydrogel nanoparticles in drug delivery' AJPTR, 1(3):19-38 (2011).
Peer, et al., "Systemic leukocyte-directed siRNA delivery revealing cyclin D1 as an anti-inflammatory target", Science, 319:627-30 (2008).
Perez-Diez, 'CD4 cells can be more efficient at tumor rejection than CD8 cells' Blood, 109:5346-54 (2007).
Petersen, et al., 'Accumulation in tumor tissue of adoptively transferred T cells: A comparison between intravenous and intraperitoneal injection', J Immunother 29, 241-9 (2006).
Punyamoonwongsa and Tighe, 'A smart hydrogel-based system for controlled drug release', Chiang Mai J Sci., 32(3):471-8 (2005).
Quemeneur, et al., Mycophenolic acid inhibits IL-2-dependent T cell proliferation, but not IL-2-dependent survival and sensitization to apoptosis, J Immunol, 169(5):2747-55 (2002).
Rahman, et al., 'Systemic lupus erythematosus', N Engl J Med, 358(9):929-39 (2008).
Ramos, et al., 'Modulation of autoantibody production by mycophenolate mofetil: effects on the development of SLE in (NZB × NZW)F1 mice', Nephrol Dial Transplant, 18(5):878-83 (2003).
Regen, "Polymerized phosphatidylcholine vesicles as drug carriers," 1985, Ann N Y Acad Sci 446:296-07.
Rehman, et al., "Angiotensin Type 2 receptor agonist compound 21 reduces vascular injury and myocardial fibrosis in stroke-prone spontaneously hypertensive rats", Hypertension, 59(2):291-9 (2012).
Ronnblom, et al., 'Cytokines as therapeutic targets in SLE', Nat Rev Rheumatol, 6(6):339-47 (2010).
Ruoslahti, et al., 'Specialization of tumour vasculature', Nat. Rev. Cancer, 2:83-90 (2002).
Ruoslahti, et al., "RGD and other recognition sequences for integrins", Annu. Rev. Cell Dev. Biol., 12:697-715 (1996).
Sammartino, et al., 'Anti-GBM disease following CTLA4 blockade in a patient with metastatic melanoma', Clinical Kidney J, 3(2):135-137 (2010).
Samstein, et al., 'The use of deoxycholic acid to enhance the oral bioavailability of biodegradable nanoparticles', Biomaterials., 29(6):703-8 (2008).

(56) References Cited

OTHER PUBLICATIONS

Sawhney, et al., 'Bioerodible hydrogels based on photopolymerized poly(ethylene glycol)-co-poly(.alpha.-hydroxy acid) diacrylate macromers', Macromolecules, 26:581-7 (1993).
Schneider, et al., 'Conversion of membrane-bound Fas(CD95) ligand to its soluble form is associated with downregulation of its proapoptotic activity and loss of liver toxicity', J. Exp. Med., 187:1205-121 (1998).
Scindia, et al., 'Anti-alpha8 integrin immunoliposomes in glomeruli of lupus-susceptible mice: a novel system for delivery of therapeutic agents to the renal glomerulus in systemic lupus erythematosus', Arthritis Rheum, 58(12):3884-91 (2008).
Selleckchem, 'TGF-beta/Smad Inhibitors' http://www.selleckchem.com/products/sb-505124.html, 4 pages, Retrieved from the internet Oct. 22, 2013.
Serkova, et al., 'Renal inflammation: targeted iron oxide nanoparticles for molecular MR imaging in mice', Radiology, 255(2):517-26 (2010).
Sfikakis, et al., 'Rituximab anti-B-cell therapy in systemic lupus erythematosus: pointing to the future', Curr Opin Rheumatol, 17(5):550-7 (2005).
Shafer-Weaver, et al., 'Immunity to murine prostatic tumors: continuous provision of T-cell help prevents CD8 T-cell tolerance and activates tumor-infiltrating dendritic cells', Cancer Research, 69:6256-64 (2009).
Shirali, et al., 'Nanoparticle delivery of mycophenolic acid upregulates PD-L1 on dendritic cells to prolong murine allograft survival', Am J Transplant, 11(12):2582-92 (2011).
Shlomchik, et al., 'From T to B and back again: positive feedback in systemic autoimmune disease', Nat Rev Immunol, 1(2):147-53 (2001).
Steenblock, et al., 'A Comprehensive Platform for Ex Vivo T-cell Expansion Based on Biodegradable Polymeric Artificial Antigen-presenting Cells', Mole Therapy, 16(4):765-72 (2008).
Tanaka, et al., "Downregulation of Fas ligand by shedding", Nat. Med., 4: 31-36 (1998).
Teichmann, et al., 'Dendritic cells in lupus are not required for activation of T and B cells but promote their expansion, resulting in tissue damage', Immunity, 33(6):967-78 (2010).
Torchilin, et al., 'Multifunctional nanocarriers', Adv Drug Deliv Rev., 58(14):1532-55 (2006).
Trevelyan, et al., 'Effect of enalapril and losartan on cytokines in patients with stable angina pectoris awaiting coronary artery bypass grafting and their interaction with polymorphisms in the interleukin-6 gene', Am J Caridol., 94(5):564-9 (2004).
Triantafyllopoulou, et al., 'Proliferative lesions and metalloproteinase activity in murine lupus nephritis mediated by type I interferons and macrophages', PNAS, 107(7):3012-7 (2010).
Van Thienen, "Protein Release from Biodegradable Dextran Nanogels," 2007, Langmuir 23:9794-801.
Vonderheide, "Prospect of targeting the CD40 pathway for cancer therapy", Clin Cancer Res, 13(4):1083-1088 (2007).
Wadia, et al., "Mycophenolic acid inhibits maturation and function of human dendritic cells and B cells", Hum Immunol, 70(9):692-700 (2009).
Wang, et al., 'Immune suppression by tumor-specific CD4+ regulatory T-cells in cancer', Semin Cancer Biol., 16:73-9 (2006).
Willimsky, et al., 'The adaptive immune response to sporadic cancer', Immunol. Rev., 220:102-12 (2007).
Wofsy, et al., 'Reversal of advanced murine lupus in NZB/NZW F1 mice by treatment with monoclonal antibody to L3T4', J Immunol, 138(10):3247-53 (1987).
Wofsy, et al., 'Successful treatment of autoimmunity in Nzb/Nzw F1 mice with monoclonal antibody to L3T4', J Exp Med, 161(2):378-91 (1985).
Wong, et al., 'Simultaneous delivery of doxorubicin and GG918 (Elacridar) by new polymer-lipid hybrid nanoparticles (PLN) for enhanced treatment of multidrug-resistant breast cancer', J Cont Rel., 116:275-84 (2006).
Xiao, et al., 'Recent advances in PEG-PLA block copolymer nanoparticles', Int J Nanomed., 5:1057-65 (2010).
Yang, et al., 'Preparation of gel-core-solid lipid nanoparticle: A novel way to improve the encapsulation of protein and peptide', Chem Pharm Bull., 58(9):1195-202 (2010).
Yoshida, et al., 'Effect of poly(lactic-co-glycolic acid) contact on maturation of murine bone marrow-derived dendritic cells', J Biomed Mater Res A, 80(1):7-12 (2007).
Zhang, et al., 'Self-assembled lipid-polymer hubrid nanoparticles: A robust drug delivery platform', ACS Nano, 2(8):1696-1702 (2008).
Ziai, et al., 'Renal allograft protection with losartan in Fisher Lewis rats: Hemodynamics, macrophages, and cytokines', Kidney Int., 57(6):2618-25 (2000).

\* cited by examiner

| nLG composition (per mg of nanoparticles) | | nLG formulation properties | |
|---|---|---|---|
| Lipids (PC:DSPE(PEG2000):Chol.)3:1:1 molar ratio | | ¹Yield | 80-90% |
| ¹PC | 40% ± 5% | ²Size | 120 nm ± 20 nm. |
| ²DSPE(PEG) | 7.5% ± 2% | ³Polydispersity Index | 0.2 ± 0.05% |
| Cholesterol | 10% ± 2 | ⁴Encap. Efficiency (SB) | 36 ± 8% |
| ³CD | 11.3% ± 2 | ⁴Encap. Efficiency (IL-2) | 80 ± 10% |
| ⁴Polymer | 27.7% ± 3 | ⁵Loading (SB) | 40 ± 10 μg/mg |
| ⁵AEM | 3.8% ± 0.5 | ⁵Loading (IL-2) | 10 ± 2 ng/mg |

¹Phosphatidyl Choline
²1,2-distearoyl-sn-glycero-3-phosphoethanolamine-N-[amino(polyethylene glycol)-2000]
³Hydroxypropyl Cyclodextran
⁴acryl-PLA-PEG(4000)-PLA-acryl
⁵Aminoethyl methacrylate ¹mg nanoparticles/mg of lipids
²Dynamic Light scattering (diameter)
³Based on Cumulants analysis (an estimate of the width of the distribution).
⁴Measured loading/Maximum Loading
⁵Mass of drug in nLG/Mass of nLG

FIG. 1E

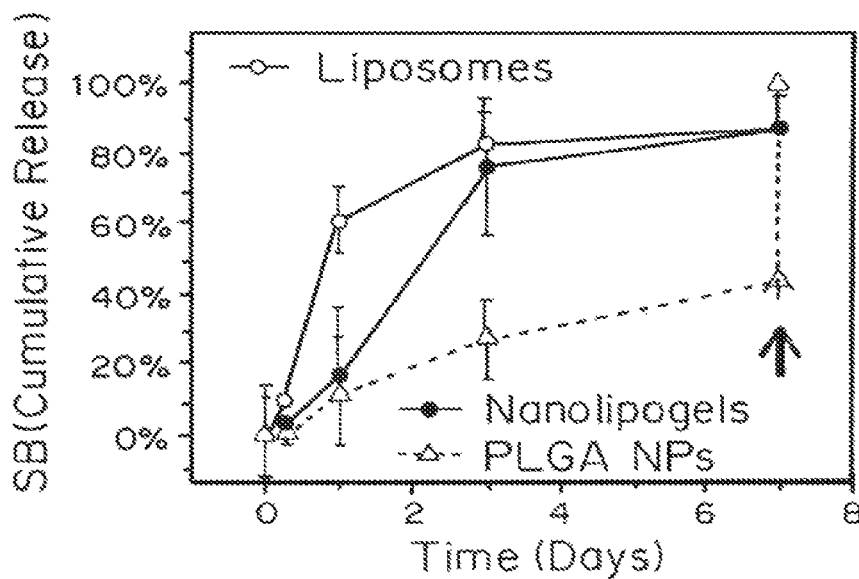
FIG. 2D
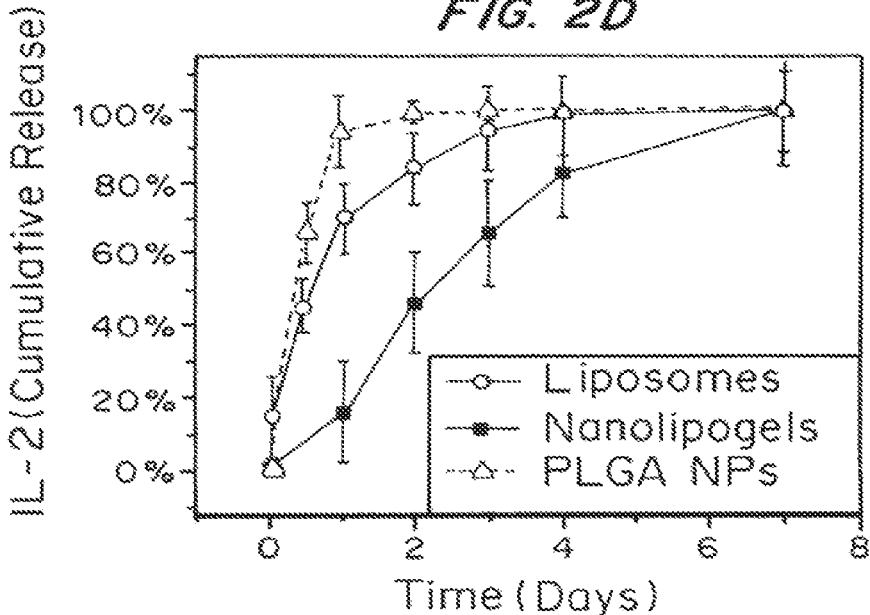
FIG. 2E
| | Size (nm) | Loading* IL-2 (ng/mg) | SB (ug/mg) |
|---|---|---|---|
| PLGA | 150±50 | 1±2 | 20±10 |
| nLG | 120±20 | 10±2 | 40±10 |
| Liposome | 100±20 | 35±15 | 3±2 |
*mass of drug in particle/particle mass
FIG. 2F

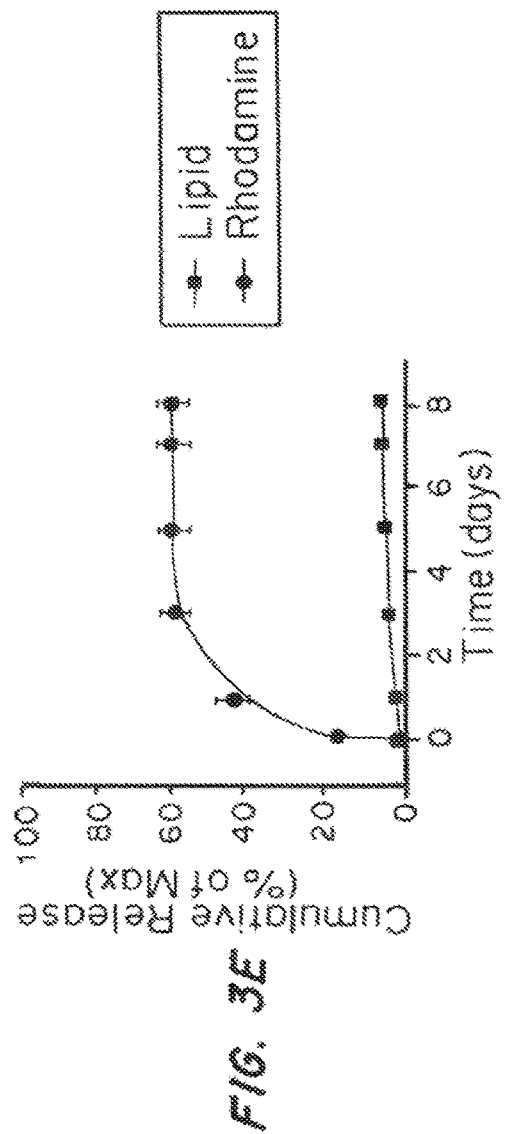
FIG. 3E
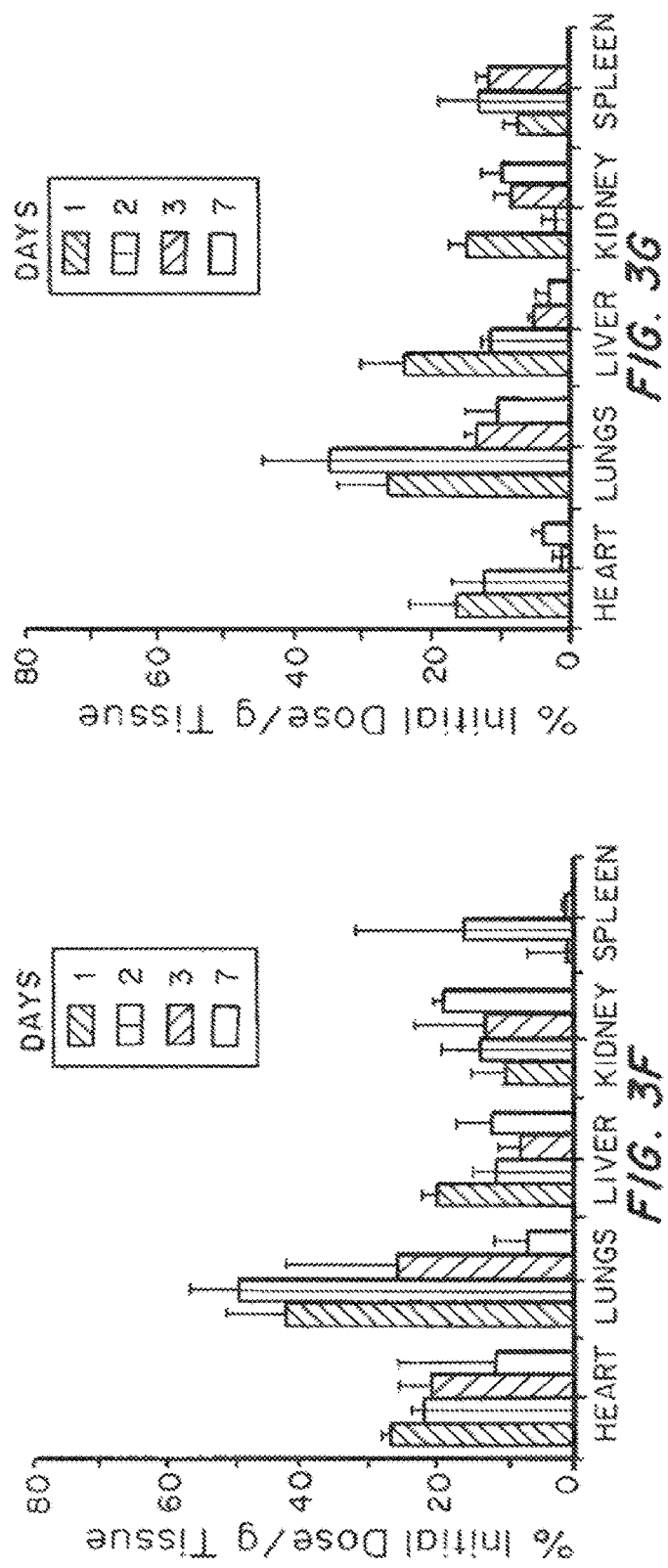
FIG. 3F
FIG. 3G

NANOLIPOGEL VEHICLES FOR CONTROLLED DELIVERY OF DIFFERENT PHARMACEUTICAL AGENTS

CROSS-REFERENCE TO RELATED APPLICATIONS

This application is a continuation of pending application U.S. application Ser. No. 16/711,591 filed on Dec. 12, 2019, which is a continuation of U.S. application Ser. No. 15/923,139, filed Mar. 16, 2018, now U.S. Pat. No. 10,603,276, which is a continuation of U.S. application Ser. No. 15/155,055, filed May 15, 2016, now U.S. Pat. No. 10,034,917, which is a continuation-in-part of U.S. application Ser. No. 14/394,161, filed Oct. 13, 2014, which is a U.S. national phase application filed under 35 U.S.C. § 371 claiming priority to PCT International Patent Application No. PCT/US2013/036487, filed Apr. 12, 2013, which claims the benefit of and priority to U.S. Provisional Application No. 61/623,486, filed Apr. 12, 2012, U.S. Provisional Application No. 61/747,624, filed Dec. 31, 2012, and U.S. Provisional Application No. 61/747,614, filed Dec. 31, 2012, each of which disclosures is incorporated herein by reference in its entirety.

STATEMENT REGARDING FEDERALLY SPONSORED RESEARCH OR DEVELOPMENT

This invention was made with Government Support under EB008260, HL055397, and HL085416 awarded by the National Institutes of Health, and 0609326 awarded by the National Science Foundation. The Government has certain rights in the invention.

FIELD OF THE INVENTION

The present invention is generally in the field of sustained delivery of high and low molecular weight, or hydrophilic and hydrophobic molecules, especially antigen or tumor and immunomodulatory molecules, using core-shell nanoparticulates, which may be targeted by size and composition to a desired cell or tissue type to enhance efficacy.

BACKGROUND OF THE INVENTION

Although efficacy of therapeutic treatments is critically dependent upon mechanism of action of the agent(s) used, other factors are often instrumental in eliciting an optimal response. Tolerable dose and time of administration relative to onset of disease are other key considerations. Additionally, there are a number of complex issues involving pharmacokinetic and pharmacodynamic characteristics that can also be significant in therapeutic response. Over the years many studies have been carried out with a vast array of therapeutic agents in an effort to establish optimal strategies for drug delivery. Over time, more and more drug remines for virtually all types of diseases have been designed to involve combination therapies; in some instances, combinations are used to improve efficacy by combining drugs that have the same or different disease targets; in others, drugs with different mechanisms of action may act synergistically; and in still others, combination therapies might involve one or more drugs that act directly on the disease state together with one or more agents that have a beneficial effect, such as reduction of pain and/or protection from side effects of organs not directly involved in the disease and/or promotion of desirable activities by natural defensive mechanisms, notably the immune system. Such disparate drugs with disparate roles in disease treatment often differ dramatically with respect to chemical nature and thus drug delivery issues in combination therapy can be very challenging.

Strategies involving the use of miniaturized vehicles that can encapsulate drugs in such a way as to allow for controlled release have shown promise as a way to optimize drug delivery characteristics. Such systems offer the possibility of successful treatment and control of many diseases with drugs whose systemic half-lives and biodistribution are critical. Because of the diverse chemical nature of different drugs, there is a distinct advantage in the design and availability of a miniaturized vehicle that can usefully control drug release in a manner that is agnostic to the chemical nature of the drug.

Particulate vaccines are promising technologies for creation of tunable prophylactics and therapeutics against a wide variety of conditions.

Vesicular and solid biodegradable polymer platforms, exemplified by liposomes and polyesters, respectively, are two of the most ubiquitous platforms in vaccine delivery studies. Immunization with poly(lactide-co-glycolide) (PLGA) nanoparticles elicits prolonged antibody titers compared to liposomes and alum. The magnitude of the cellular immune response is highest in animals vaccinated with PLGA, which also shows a higher frequency of effector-like memory T-cell phenotype, leading to an effective clearance of intracellular bacteria. The difference in performance of these two common particulate platforms is shown not to be due to material differences but appears to be connected to the kinetics of antigen delivery. Liposomes are easily modified for encapsulation of small hydrophilic molecules, and even proteins. However, the stability of these formulations and the release profiles of encapsulated agents are not easily controlled. Biodegradable solid particles, on the other hand, such as those fabricated from poly(lactic-co-glycolic acid) (PLGA), are highly stable and have controllable release characteristics, but pose complications for facile encapsulation and controlled release of therapeutic cytokines or for combinatorial delivery. To overcome these limitations, hybrid platforms that integrate features of different materials can offer advantages in combinatorial encapsulation and delivery. Such systems have been demonstrated based on a core-shell methodology in which an organic or inorganic mesoporous or nanoporous core entrapping molecules of interest is coated with lipids or polymers. These hybrid systems can enhance encapsulation and release of a wide variety of agents, such as small molecule drugs, proteins and nucleic acids, while promoting favorable pharmacokinetics and biodistribution of the encapsulant.

Hybridized systems, as such, are clearly attractive drug delivery alternatives and have been explored in different studies. Such systems can be engineered with a fluid biological bilayer that enhances their circulation or potential for targeting while enabling the delivery of agents of different physical properties. Several core-shell hybrid systems have been demonstrated for this purpose and indeed offer exciting new possibilities for combinatorial delivery that can work in cancer therapy.

It is clear that the rate of release of bioactives, especially in the vaccine field, is critically important to the function, not just which bioactives are incorporated. The complexity associated with delivery of two different agents, such as an antigen and an immunomodulator, makes it more difficult to find a delivery vehicle that allows for controlled release of the agents at different rates. This is particularly the case where the properties of the two agents are different, such as when one is hydrophobic and one is hydrophilic, or one is high molecular weight and the other is low molecular weight. Even though it is possible to provide particles that differ in chemical properties, it is difficult to ensure that the agents are released at the correct time, for example, without having to diffuse from the core through the shell, where the core is hydrophobic and the shell is hydrophilic (or vice versa) and the properties of the agents lead them to migrate into another area of the delivery device rather than out of the device, or, for example, where one agent is very low molecular weight and tends to diffuse out rapidly and the other agent is very high molecular weight and tends to diffuse out extremely slowly.

It is therefore an object of the present invention to provide means for delivery of two or more pharmaceutical agents at different rates, especially agents with different chemical properties and/or molecular weights.

SUMMARY OF THE INVENTION

Nanolipogels, methods of incorporation of agents into these delivery vehicles and making and using these compositions for the treatment of disease have been developed. These are designed to be loaded with agents either prior to, during or after formation and subsequently function as controlled-release vehicles for the agents. "Nanolipogel", is a nanoparticle that combines the advantages of both liposomes and polymer-based particles for sustained delivery of both proteins and small molecules. In a preferred embodiment, the nanolipogel is a Lipid-Enveloped Dendrimer (LED).

The nanolipogel is typically loaded with more than one agent such that controlled release of the multiplicity of agents is subsequently achieved.

The nanolipogel is loaded with one or more first agents during formation and one or more second agents following formation by the process of rehydration of the nanolipogel in the presence of the second agents. For example, the nanolipogel is loaded with a molecule that serves as an adjuvant and the nanolipogel thereafter incorporates one or more target antigens after formation, for the controlled release of adjuvant together with the antigens. Alternatively, the nanolipogel loaded with adjuvant is inserted into the site of a tumor in a patient, the tumor is ablated, the nanolipogel is loaded with released tumor antigens and the nanolipogel releases the tumor antigens together with adjuvant into the body of the patient in a controlled manner.

A nanolipogel is constructed of any of several suitable hydrogel materials, or combinations thereof, or other materials that are capable of in situ loading and release of agent such as cyclodextrin or ion exchange resins. The nanolipogel can be in the form of spheres, discs, rods or other geometries with different aspect ratios. The nanolipogel is typically formed of synthetic or natural polymers capable of encapsulating agents by remote loading and tunable in properties so as to facilitate different rates of release.

A nanolipogel is a delivery vehicle including a lipid bilayer surrounding a hydrogel core, which may include an absorbent such as a cyclodextrin or ion-exchange resin. Nanolipogels can be constructed so as to incorporate a variety of different chemical entities that can subsequently be released in a controlled fashion. These different incorporated chemical entities can differ dramatically with respect to size and composition. Nanolipogels have been constructed to contain co-encapsulated proteins as well as small hydrophobic drugs within the interior of the lipid bilayer. Agents incorporated within nanolipogels can be released into the milieu in a controlled fashion, for example, nanolipogels provide a means of achieving simultaneous sustained release of agents that differ widely in chemical composition and molecular weight. Additionally, nanolipogels can favorably modulate biodistribution.

In a non-limiting example, one of the agents is an antigen and a second agent is an immunoadjuvant, resulting in sustained release of the antigen together with the adjuvant to optimize an immune response. In one example, simultaneous sustained delivery by nanolipogels of an immunostimulatory protein, Interleukin-2 (IL-2), as well as a low molecular weight organic molecule, 2-(5-benzo[1,3]dioxol-5-yl-2-tert-butyl-3H-imidazol-4-yl)-6-methylpyridine hydrochloride, an inhibitor of transforming growth factor-β (TGF-β), is achieved. This construct leads to an anti-tumor response in a murine system that is far superior to that achievable with the administration in solution of either agent alone or a combination of the two.

The examples demonstrate the importance of antigen persistence mediated by particulate platforms and its role in the long-term appearance of effector memory cellular response. Systemic administration of CD4-targeted cytokine-loaded nanoparticles ("NPs") was able to promote tolerance through expansion of host regulatory cells in murine allograft models. CD4-targeted TGF-β/IL-2 NPs alone induced a 3% increase in Treg frequency in the spleen and mesenteric lymph nodes of healthy mice. Donor-specific transfusion of splenocytes pretreated with CD4-targeted LIE nanoparticles NPs resulted in a 4-fold increase in donor-specific Tregs and significantly enhanced tolerance of fully mismatched heart allografts from 7 to 12 days.

In the B16 murine melanoma model, the proliferative and antitumor effects of IL-2 cytokine therapy are hypothesized to be thwarted by TGF-β secretion and the activity of Tregs within the tumor. Therefore, nanolipogels were used to co-deliver the small molecule TGF-β inhibitor SB505124 and IL-2 to the tumor microenvironment. Tumor-localized drug delivery was found to be critical. The most striking and significant survival benefits or reductions in tumor growth were observed in mice receiving simultaneous Nanolipogel ("nLG")-mediated delivery of SB and HL-2. Monotherapies and soluble agent therapy failed to delay subcutaneous tumor growth even when administered via intratumoral injection, but nLG-SB+IL-2 induced significant delays in tumor growth rates and even resulted in complete regression in 40% of mice followed for long-term survival. Encapsulation in nanolipogels improved drug circulation following intravenous dosing and resulted in a nearly 4-fold dose increase in the lungs up to 72 hours after administration. After one week of therapy, intravenous Nanolipogel (nLG-SB+IL-2) therapy significantly reduced the number of metastatic lung growths compared to controls.

BRIEF DESCRIPTION OF THE DRAWINGS

In FIG. 1A, methacrylate-functionalized cyclodextrin (CD) was used to solubilize a bioactive such as the TGF-0 inhibitor (SB505124). In FIG. 1B, nanolipogels were formulated from lyophilized liposomes loaded with biodegradable crosslinking polymer, acrylated-drug (CD-SB505) complex, and a second drug such as the peptide IL-2 cytokine. This core-shell structure facilitated entrapment of drug loaded CD and the IL-2 in an interior biodegradable polymer matrix with a PEGylated liposomal exterior. Succinylated β-cyclodextrin (CTD, Inc.) was functionalized with 2-aminoethyl methacrylate (Sigma)

by stirring a 1:3 molar ratio of the compounds in 1×PBS for 1 hour at room temperature. The $^1$H NMR spectra (500 MHz, $D_2O$) of SB505124, randomly succinylated β-CD, and the inclusion complex of SB505124 with randomly succinylated β-CD was determined. The differences observed in the aromatic proton region of SB505124 demonstrate formation of the inclusion complex. The $^1$H NMR spectra (500 MHz, $D_2O$) of rhodamine B, randomly succinylated β-CD, and the inclusion complex of rhodamine B with randomly succinylated β-CD showed the differences observed in the aromatic proton region of rhodamine B demonstrate formation of the inclusion complex.

Figure 1A:
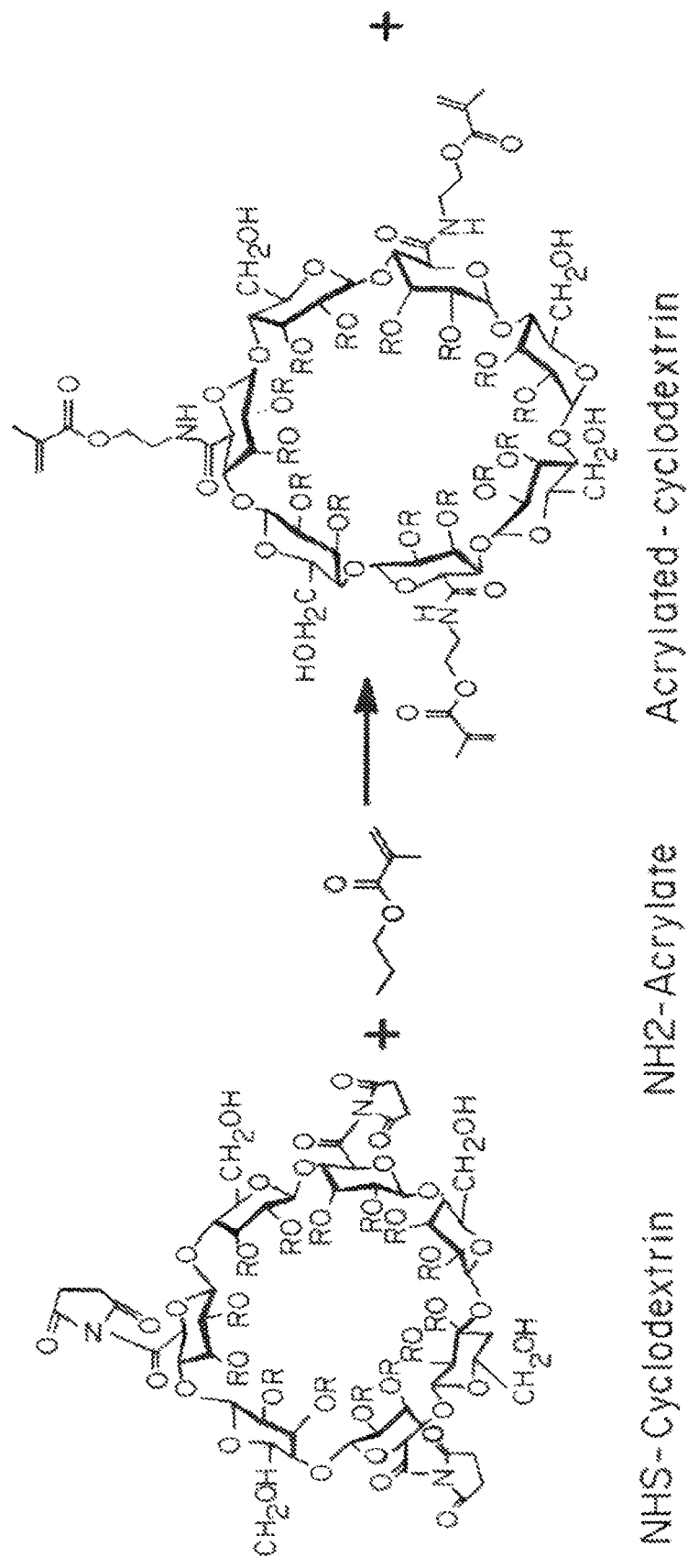
FIGS. 1A-1B are schematics of the fabrication of the nanolipogel particles (nLG).
Figure 1A:
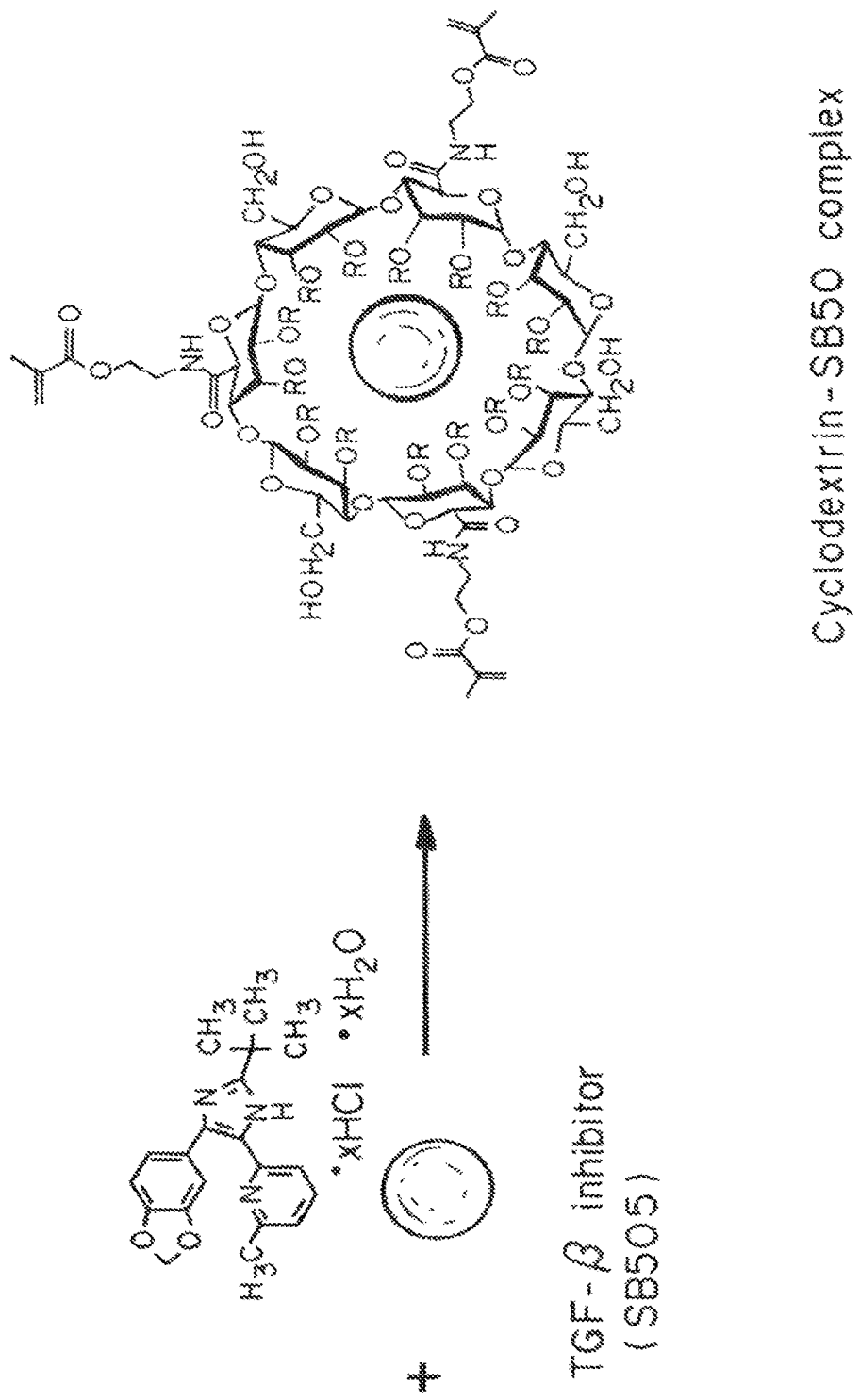
Figure 1B:
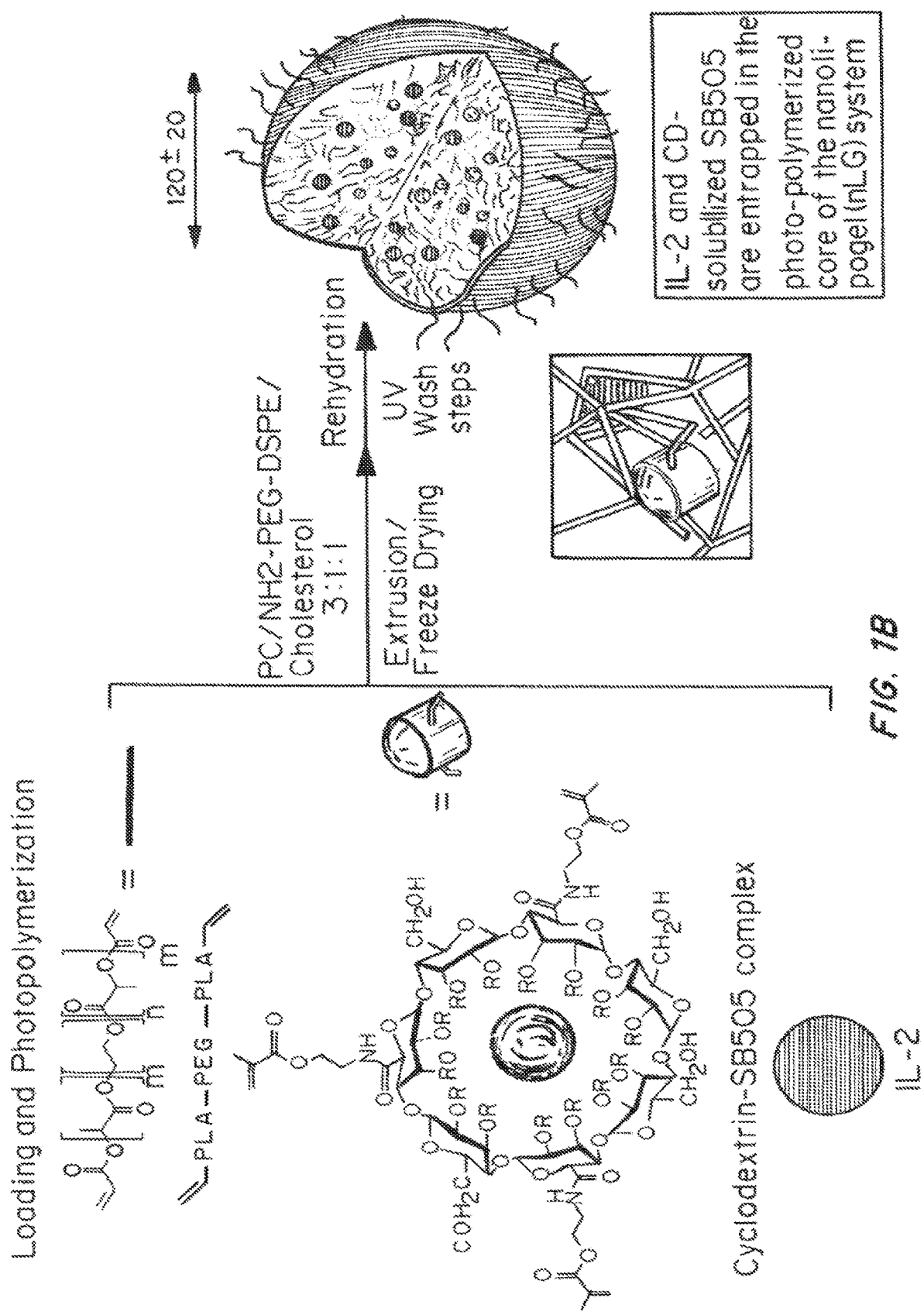
Figure 1C:
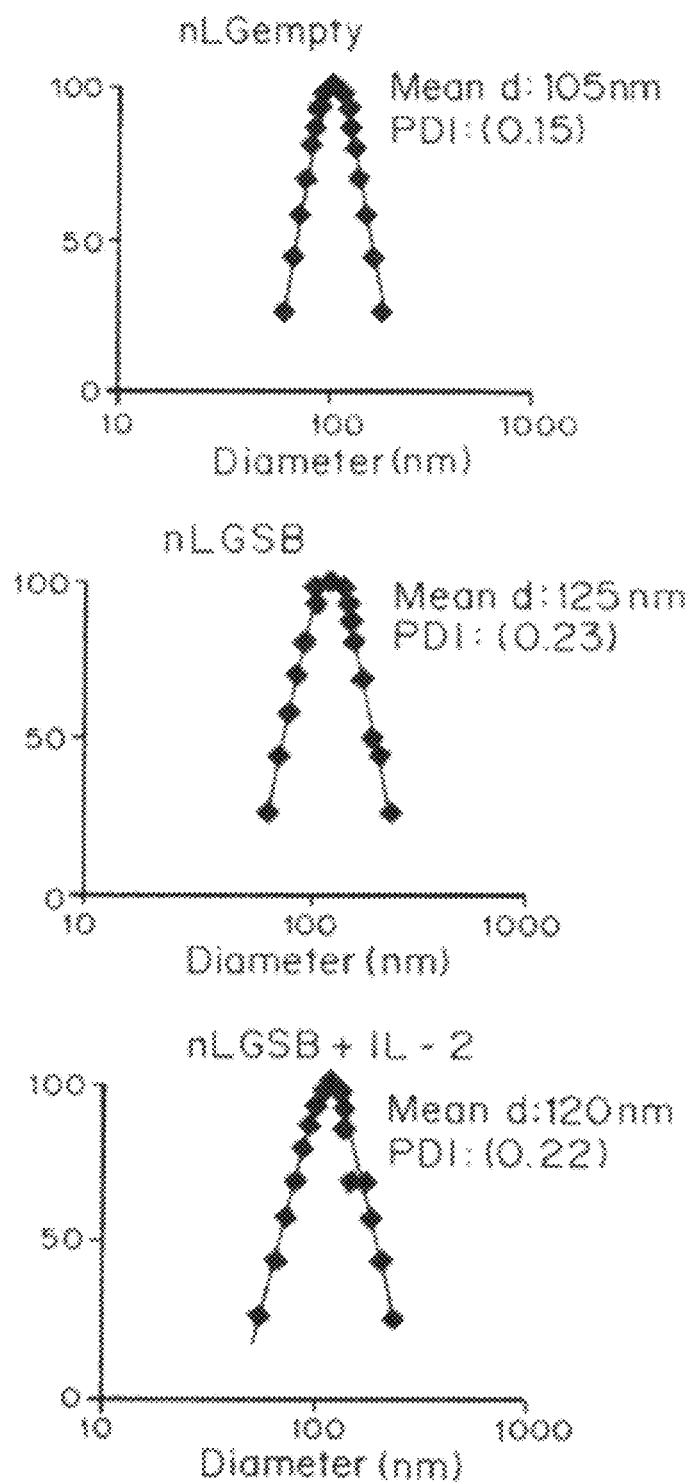
Figure 1D:
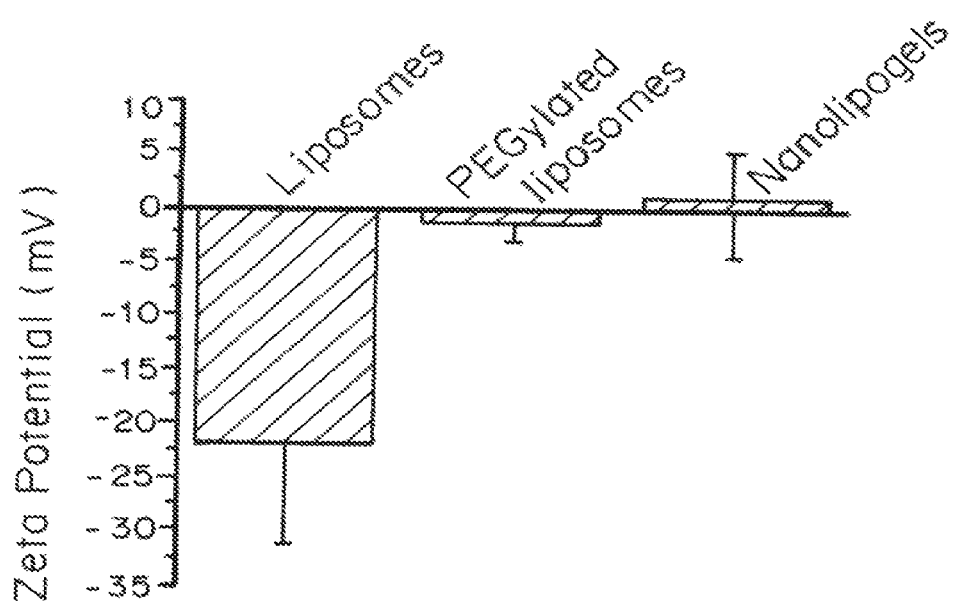
Figure 1F:
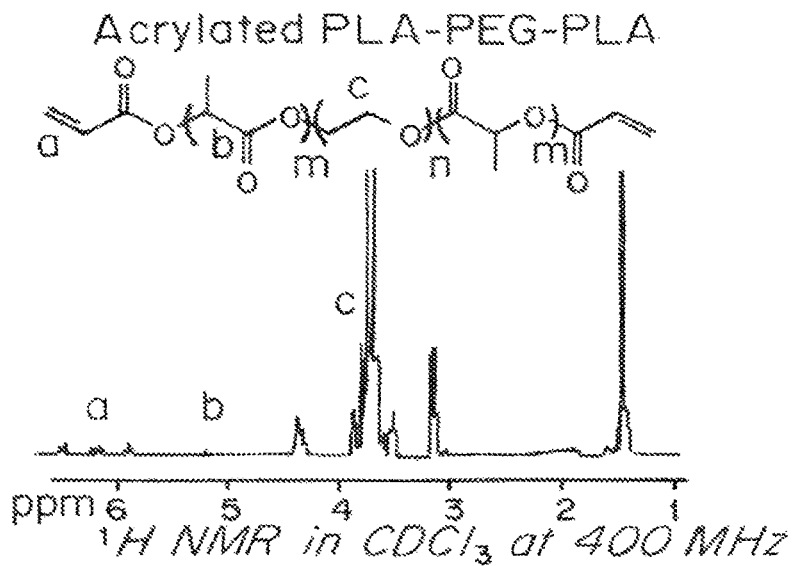
Figure 1G:
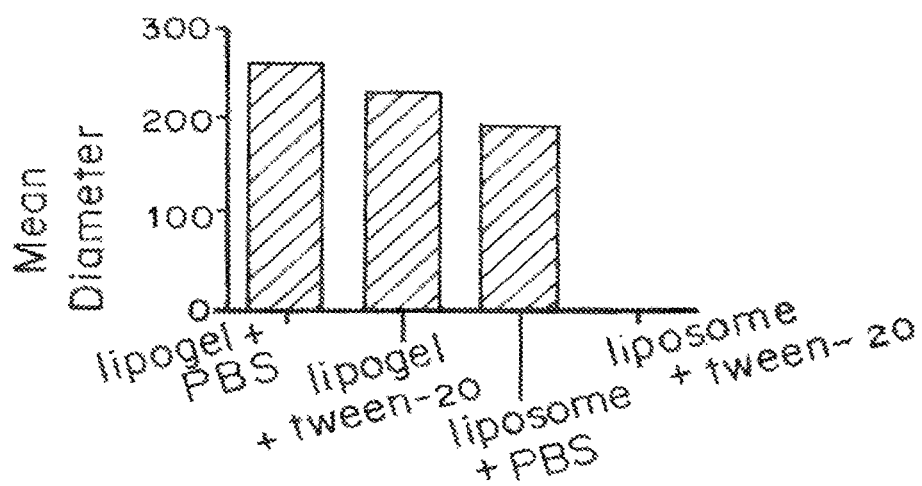

FIGS. 1C-1G show nanolipogel characterization. Nanolipogel size was determined by dynamic light scattering on a ZetaPALS instrument (Brookhaven Instruments) in PBS at room temperature. FIG. 1C shows that encapsulation of SB or SB+IL-2 had no significant effect on particle mean diameter or polydispersity. Mean diameter and polydispersity index are representative of 2 lots of each nanolipogel type (n=10 measurements per sample). The zeta potential of PC/cholesterol liposomes, PC/cholesterol/PE-PEG-$NH_2$ liposomes, and nanolipogels were evaluated in 0.1×PBS using a Malvern nanosizer. FIG. 1D shows that the zeta potential of liposomes and nanolipogels incorporating amine-terminated PE-PEG was found to be close to neutral. FIG. 1E shows the composition and formulation properties of the nanolipogel formulation. FIG. 1F shows the polymer structure verified by $^1$H NMR. Cryo-TEM of nanolipogels demonstrate the formation of spherical liposomal structures. For TEM analysis, nanolipogel samples were stained with osmium tetroxide and then imaged on an FEI Tenai Biotwin microscope. Lipid-specific osmium tetroxide staining of cryosectioned samples had a localized staining pattern confined to the exterior membrane of the particle. FIG. 1G shows that the photopolymerized polymer/CD forms nanoparticulate hydrogel structures that are detectable by light scattering even after disruption of the liposomal exterior by detergent.

Figure 2A:
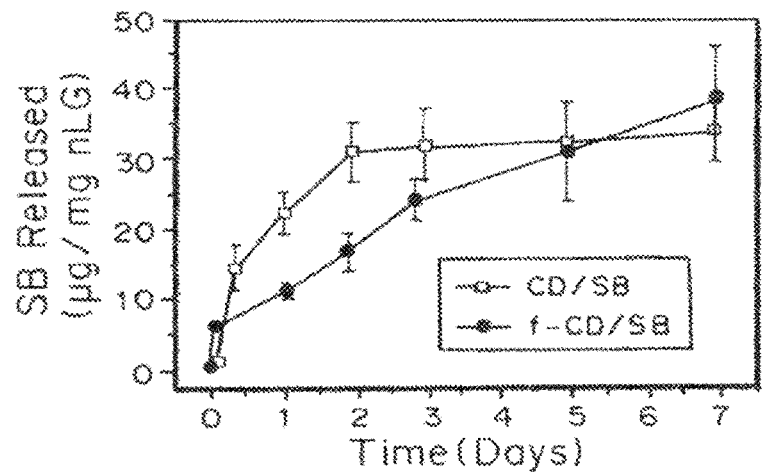
Figure 2B:
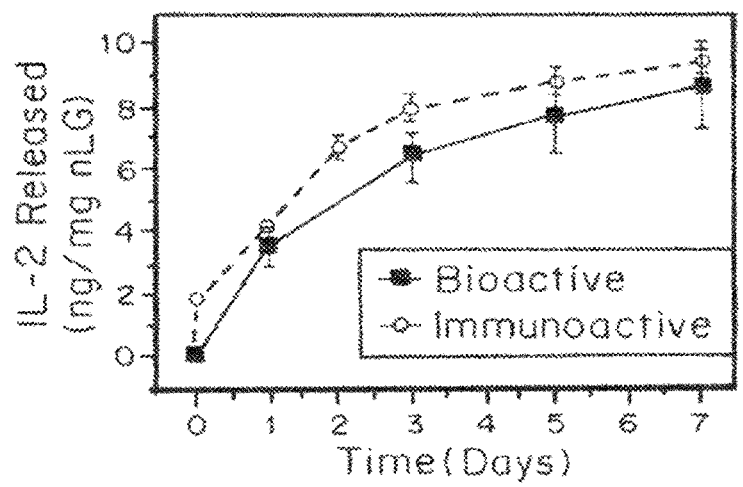
Figure 2C:
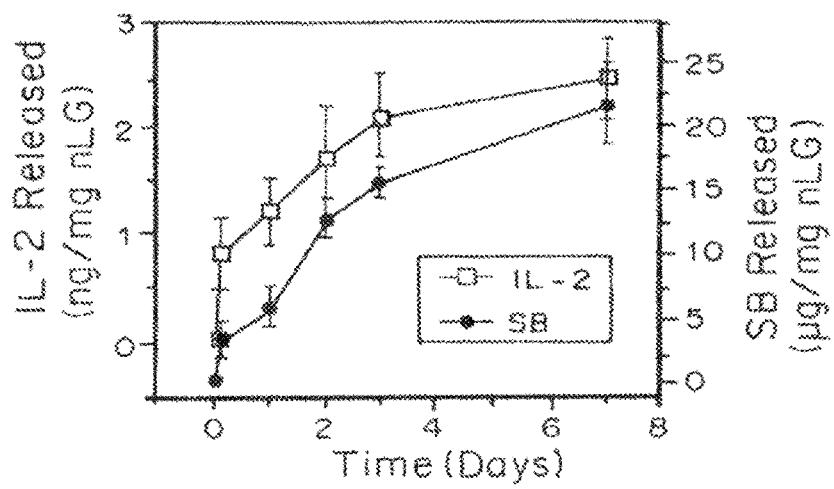

FIGS. 2A-2E are comparative release profiles from nLG, liposomes and solid polymer nanoparticles (PLGA). Cumulative CD- or methacrylate functionalized-CD (f-CD)-solubilized SB released from nLGs normalized by initial carrier mass demonstrated that polymerization of nanolipogels improved the sustained nature of SB release (FIG. 2A). Hydroxypropyl β-CD was used for SB complexation with the unfunctionalized CD. Cumulative IL-2 released determined by ELISA (immunoactive) and by a bioactivity study (bioactive) from nLGs normalized by initial nanolipogel mass demonstrated that bioactivity of IL-2 was unaffected by encapsulation (FIG. 2B). Release of SB and IL-2 was not affected by incubation of 10 mg nLG in 1 ml full serum (FIG. 2C). Comparative cumulative release of SB from liposomes, nanolipogels, and degradable polymeric (poly lactide-co-glycolide) nanoparticles (PLGA NPs) demonstrated that incorporation of photo-cured polymer in the nanolipogel vehicle enabled better sustained release and more complete release of cyclodextrin-solubilized SB (FIG. 2D). PLGA NPs (mean diameter=150±50 nm) were prepared by using a modified water/oil/water double emulsion technique. Liposomes were prepared in an identical manner as the nLG without the polymer core. Liposomes were loaded with IL-2 and SB similar to nanolipogels. The diminished percent of encapsulated SB released from PLGA NPs is attributed to the interaction of the relatively hydrophobic polymer with SB. All particulate formulations were dissolved in 0.1N NaOH+1% SDS to determine 100% release at 7 days (arrow) (FIG. 2D). Comparative cumulative release of IL-2 from liposomes, nanolipogels, and PLGA NPs demonstrated that encapsulation of IL-2 in nanolipogels enabled better sustained release of cytokine. Cumulative release is presented as % of total IL-2 released through 7 days. (FIG. 2E) Data in all graphs represent mean of triplicate samples & 1 standard deviation. FIG. 2F compares the sizes and loading of IL-2 and SB in PLGA, nanolipogels and liposomes.

Figure 3A:
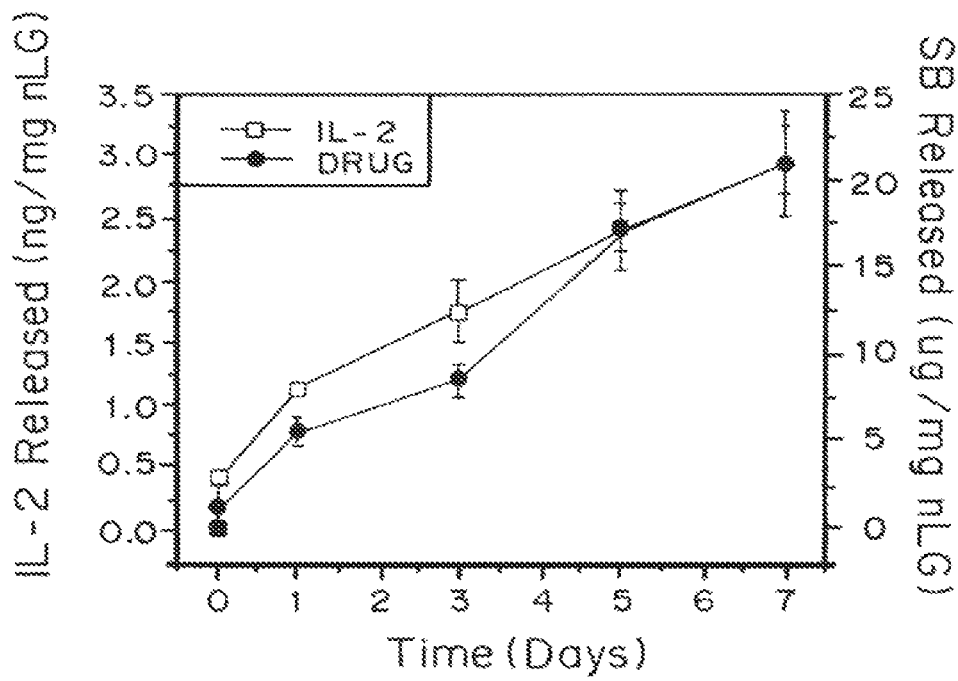
Figure 3B:
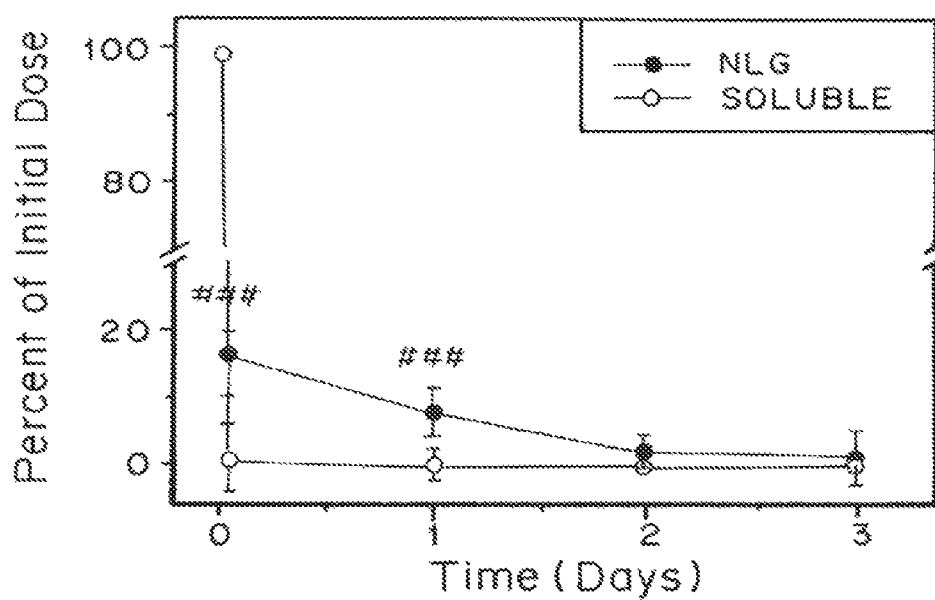
Figure 3C:
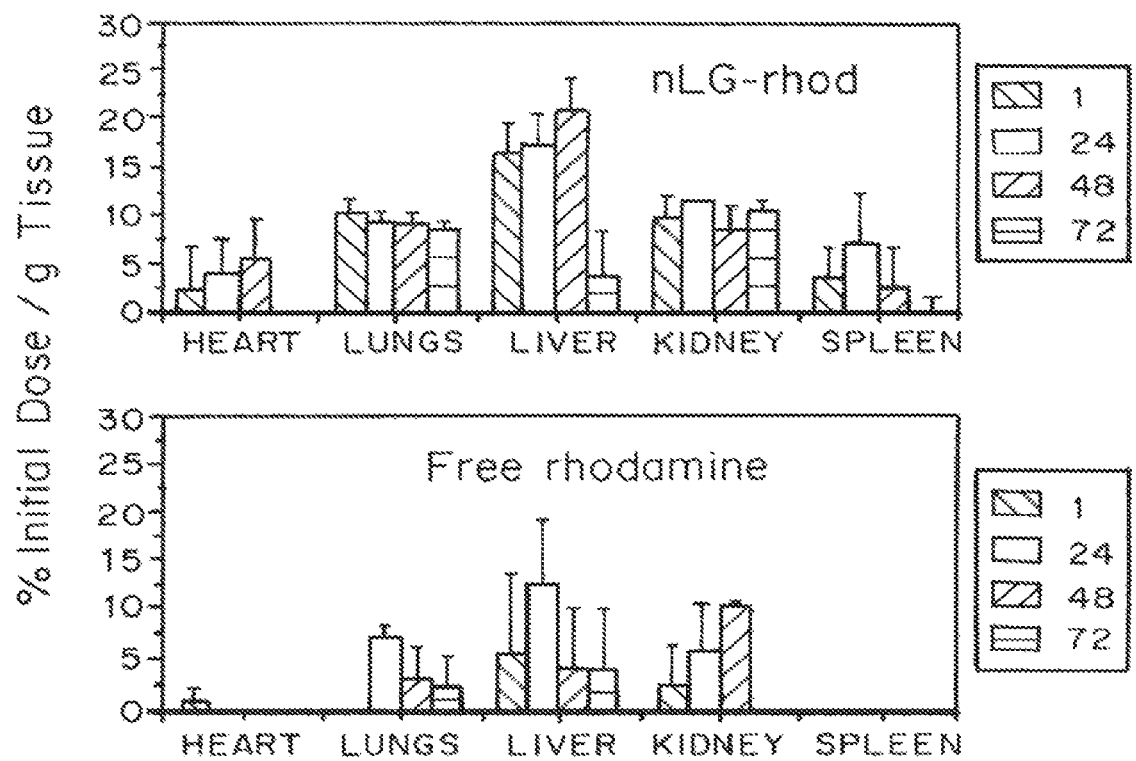
Figure 3D:
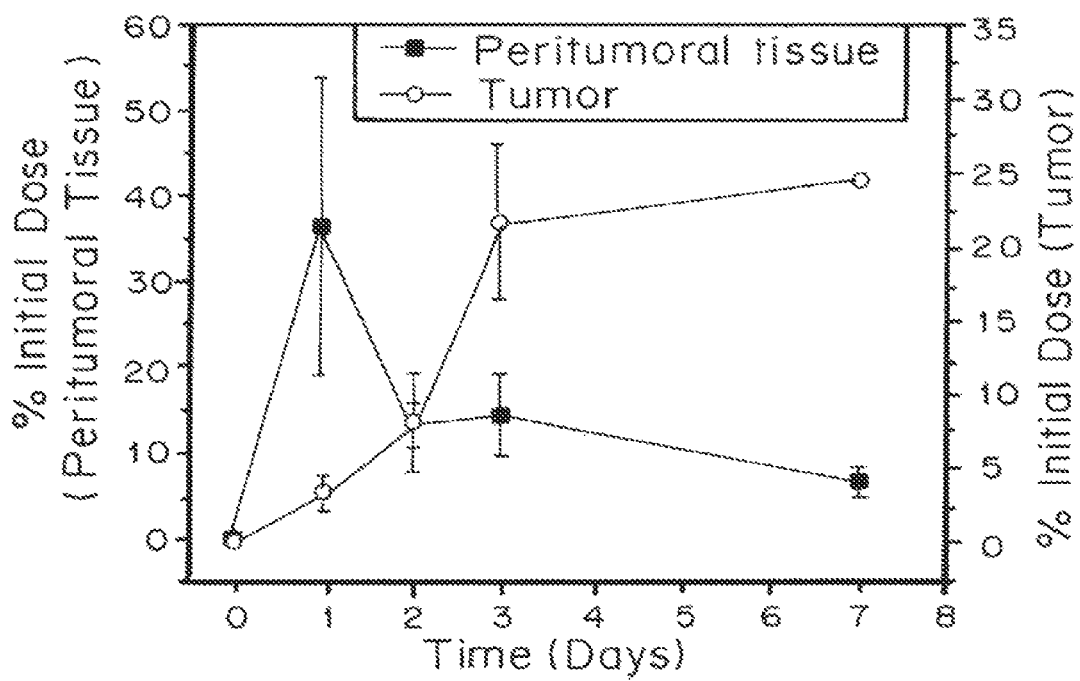

FIGS. 3A-3G are graphs showing controlled release, clearance, and biodistribution. The distribution of both nanolipogel carrier and encapsulated drug payload was investigated using dual-labeled NLG; fluorescein-labeled phosphoethanolamine was incorporated into the lipid component of rhodamine-loaded nanolipogels. Spectrofluorimetric analysis at 540/625 nm and 490/517 nm show dose-dependent fluorescence with no spectral overlap. FIG. 3A is a graph of cumulative IL-2 (ng/mg nLG) and drug (μg SB/mg nLG) released from co-loaded nLGs normalized by carrier mass. Error bars in all plots represent ±1 standard deviation. All experiments were repeated at least twice with similar results. FIG. 3B is a graph showing clearance (percent of initial dose) of drug dose overtime in days: Encapsulation in nanolipogels significantly increased the remaining percentage of initial dose in the blood at 1 and 24 hours post-injection (two population t test, $p<0.01$ ###). FIG. 3C is a graph of whole body distribution. Mice received a single dose of rhodamine-loaded nanolipogel or soluble rhodamine (in saline) via intravenous tail vein injection. Animals were sacrificed at 1, 24, 48, and 72 hours post-injection for extraction and quantification of fluorescence; whole body biodistribution was determined with rhodamine labeling. Significantly higher (two population t test, $p<0.01$) amounts of rhodamine were detected in the major organs of nanolipogel-treated animals compared to animals injected with free dye. FIG. 3D is a graph of time dependent accumulation n in subcutaneous tumor: Cumulative rhodamine tumor penetration (circles) after B16 peritumoral injection in B6 mice. Peritumoral tissue was collected to quantify the remaining dose of nLG surrounding the tumor (squares). Controlled release demonstrates release of rhodamine, but not lipid (FIG. 3E). Mice bearing subcutaneous B16 tumors received a single IV (tail vein) injection of dual-labeled NLG. Animals were sacrificed at 1, 2, 3, and 7 days post injection and tissues collected for homogenization, extraction, and quantification of rhodamine and fluorescein-PE. Analysis of serum shows prolonged circulation of both encapsulant and delivery vehicle. Similar patterns of biodistribution were observed between lipid (FIG. 3F) and drug payload (FIG. 3G), with highest accumulations of drug occurring in the lungs and liver.

Figure 4A:
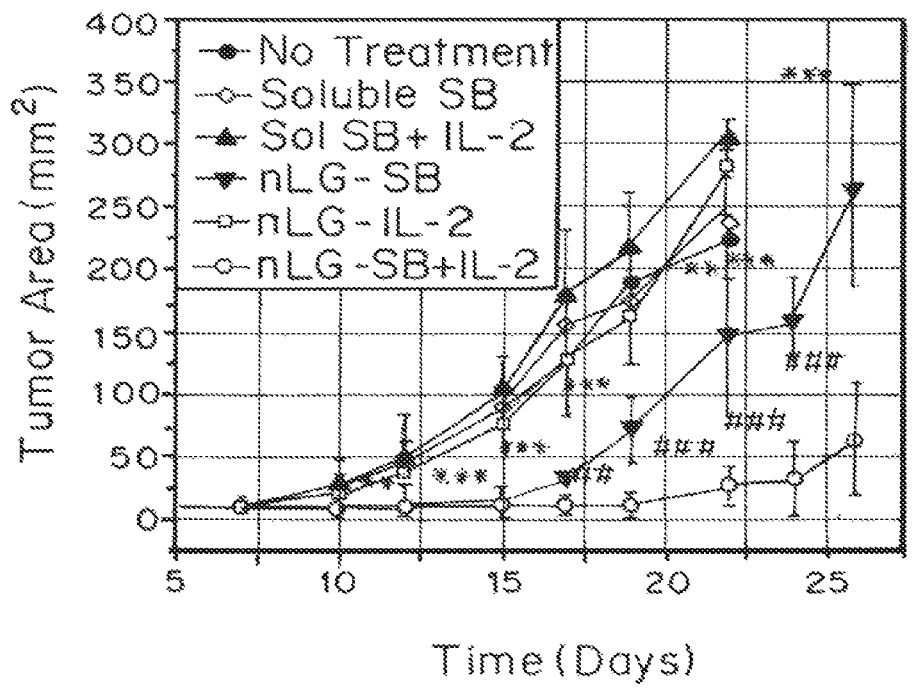
Figure 4B:
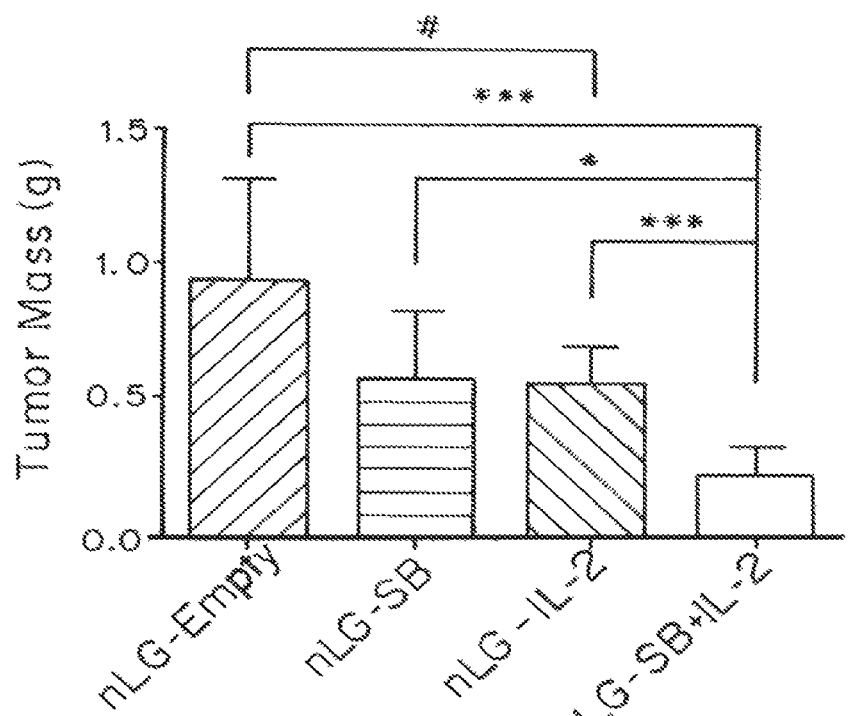
Figure 4C:
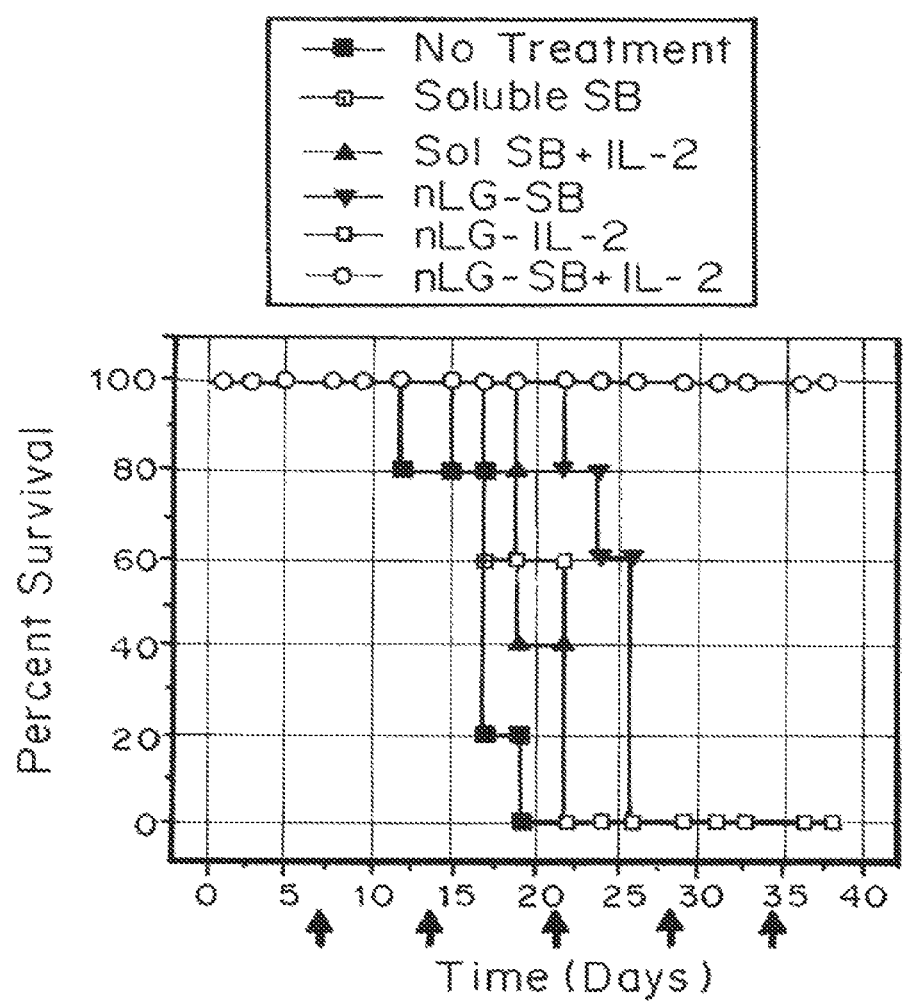

FIGS. 4A-4C are graphs showing the clinical effects of intratumoral nanolipogel therapy on subcutaneous melanoma. FIG. 4A is a graph of tumor area versus time (day 0 was the day of tumor cell injection). Red arrows indicate treatments (via intratumoral injection). Mice bearing subcutaneous tumors were euthanized when either greatest tumor dimension was larger than 15 mm or when exhibiting signs of illness. Tumor areas of deceased mice were not included after the day of death. Each group initially contained five mice except for the nLG-SB+IL-2 group, which contained four. Error bars represent ±1 standard deviation. Tumors in the nLG-SB and nLG-SB+IL-2 groups are significantly smaller than all other groups (two population T test, $P<0.001$) beginning day 12. Tumors in the nLG-SB+IL-2 group are significantly smaller than in the nLG-SB group starting day 17 ($P<0.01$, ##) and all other days afterwards ($P<0.001$). FIG. 4B is a graph of tumor masses of nLG-treated groups seven days after treatment. Mice were euthanized directly prior to tumor mass determination. Error bars represent ±1 standard deviation averaged across six (nLG-Empty), ten (nLG-IL-2), nine (nLG-SB), and ten (nLG-SB+IL-2) mice. Each group initially contained 10 mice. Two population T tests showed tumors in the nLG-SB+IL-2 group were significantly lower than the nLG-Empty (P<0.001, *), nLG-IL-2 (P<0.001, *), and nLG-SB (P<0.05, *) groups. A two population T test showed tumor masses in the nLG-IL-2 group were significantly lower than the nLG-Empty (P<0.05, #). FIG. 4C is a survival plot of mice from the same study given in FIG. 4A. Arrows denote treatment days. The survival of mice treated with nLG-SB was significantly longer by Mantel-Cox and Gehan-Breslow-Wilcoxon analyses (P<0.01) and nLG-SB+IL-2 significantly extended survival by both analyses (P<0.001).

Studies were repeated 2-3 times with similar results.

Figure 5A:
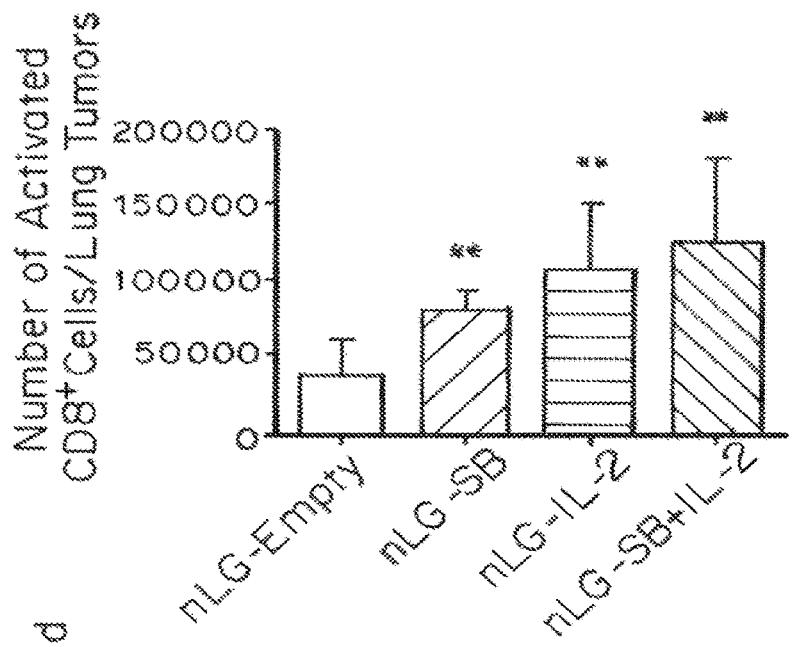
Figure 5B:
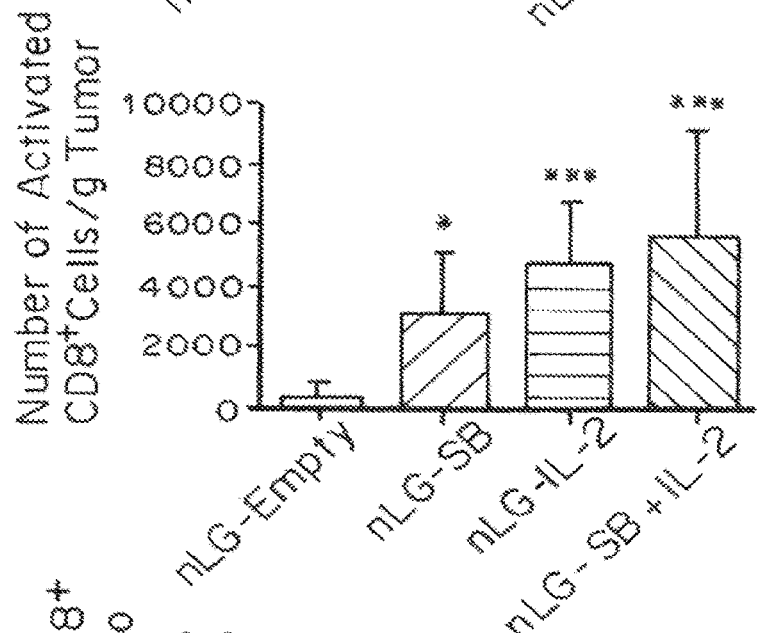
Figure 5C:
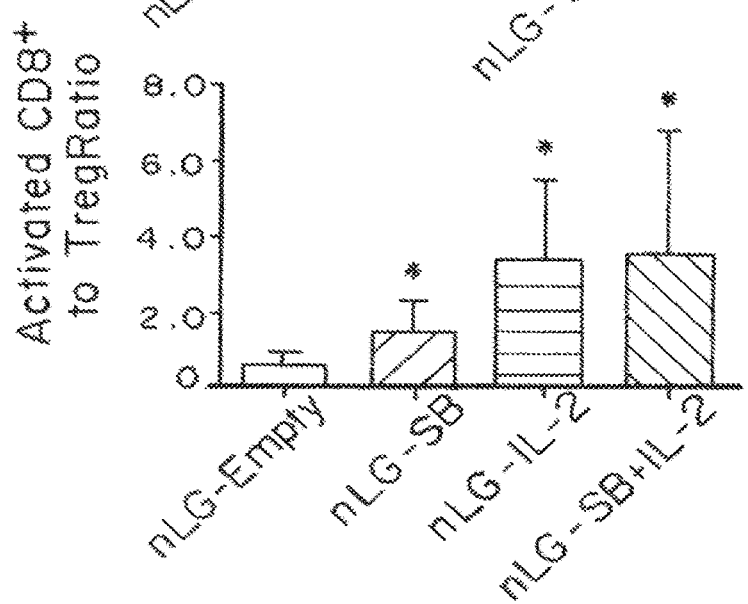

FIGS. 5A-5C shows the adaptive immune response and mechanism of nLG-SB+IL-2 action. Each group contained six mice and studies were repeated 2-3 times with similar results. FIG. 5A is a graph of the absolute number of activated $CD8^+$ cells present in lung tumors (normalized per number of tumors). All groups have significantly greater numbers (P<0.01) compared with empty nLGs. FIG. 5B is a graph of the absolute number of activated $CD8^+$ cells present in tumors (normalized per tumor mass) removed from mice seven days after treatment. Treatment with nLG-SB significantly increased activated $CD8^+$ populations (P<0.05), as did treatment with nLG-IL-2 or nLG-SB+IL-2 (P<0.001), over unloaded particles. Error bars represent L 1 standard deviation averaged across six (nLG-Empty), ten (nLG-IL-2), nine (nLG-SB), and ten (nLG-SB+IL-2) mice. Each group initially contained 10 mice. FIG. 5C is a graph of the activated $CD8^+$: Treg ratio in TILs. All groups have significantly greater ratios (P<0.05) compared with empty nLGs.

Figure 6A:
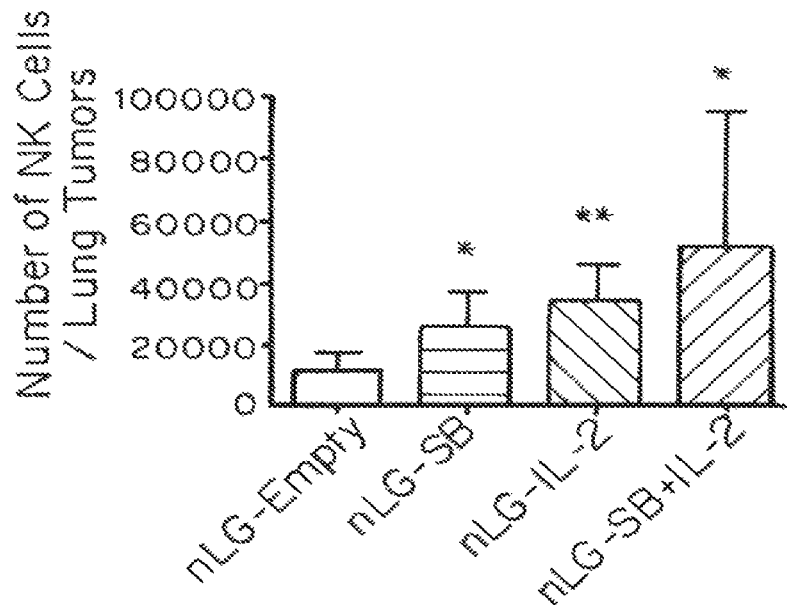
Figure 6B:
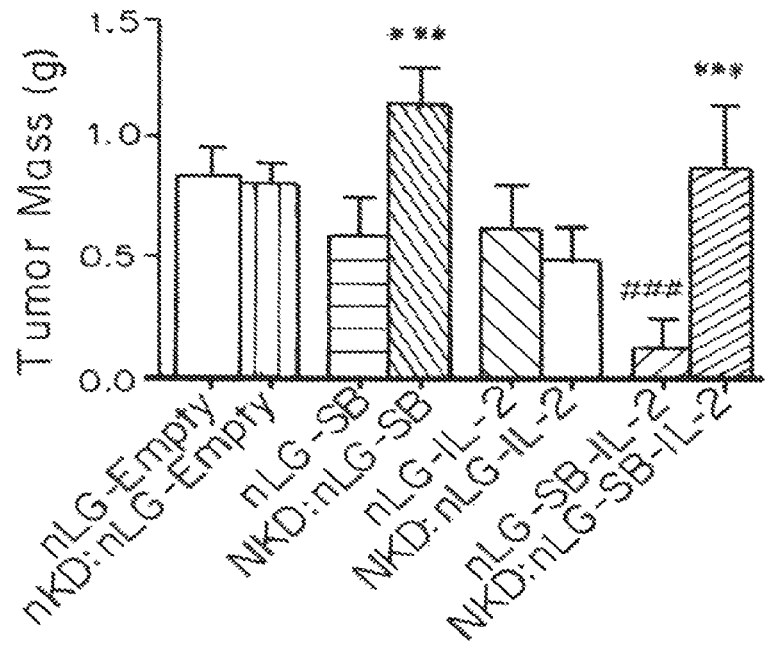
Figure 6C:
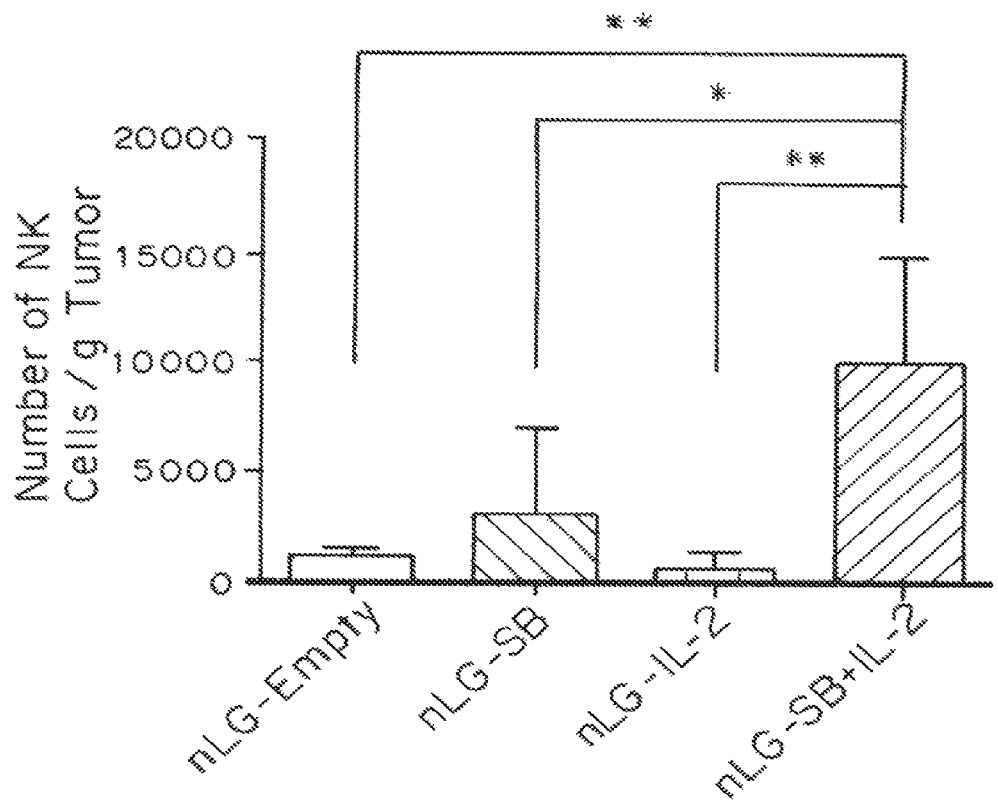

FIGS. 6A-6C are graphs showing the role of NK cells in tumor immunotherapy after combination delivery. Each group contained six mice and studies were repeated 2-3 times with similar results. FIG. 6A is a graph of the absolute number of NK cells present in tumors (normalized per number of tumors). Compared to the empty particle group, significantly more NKs were present in the lungs following treatment by nLG-SB+IL-2 (P<0.05), nLG-SB (P<0.05), and nLG-IL-2 (P<0.01). FIG. 6B is a graph comparing tumor masses from wild type (WT) or NK-depleted (NKD) mice euthanized seven days after initial treatment. Each group initially contained 10 mice. The nLG-SB+IL-2-treated WT group has significantly smaller tumors than all other treatment groups (P<0.001). The NKD nLG-SB and nLG-SB+IL-2 groups have significantly larger tumors than their WT counterparts (both P<0.001). Studies were repeated 2-3 times with similar results, FIG. 6C is a graph of the absolute number of NK cells present in tumors (normalized per tumor mass) for the same study. The nL-SB+IL-2-treated group has significantly more NKs than the control group (P<0.01), the SB-treated group (P<0.05), and the IL-2-treated group (P<0.01). Error bars represent ±1 standard deviation averaged across six (nLG-Empty), ten (nLG-IL-2), nine (nLG-SB), and ten (nLG-SB+IL-2) mice.

Figure 7A:
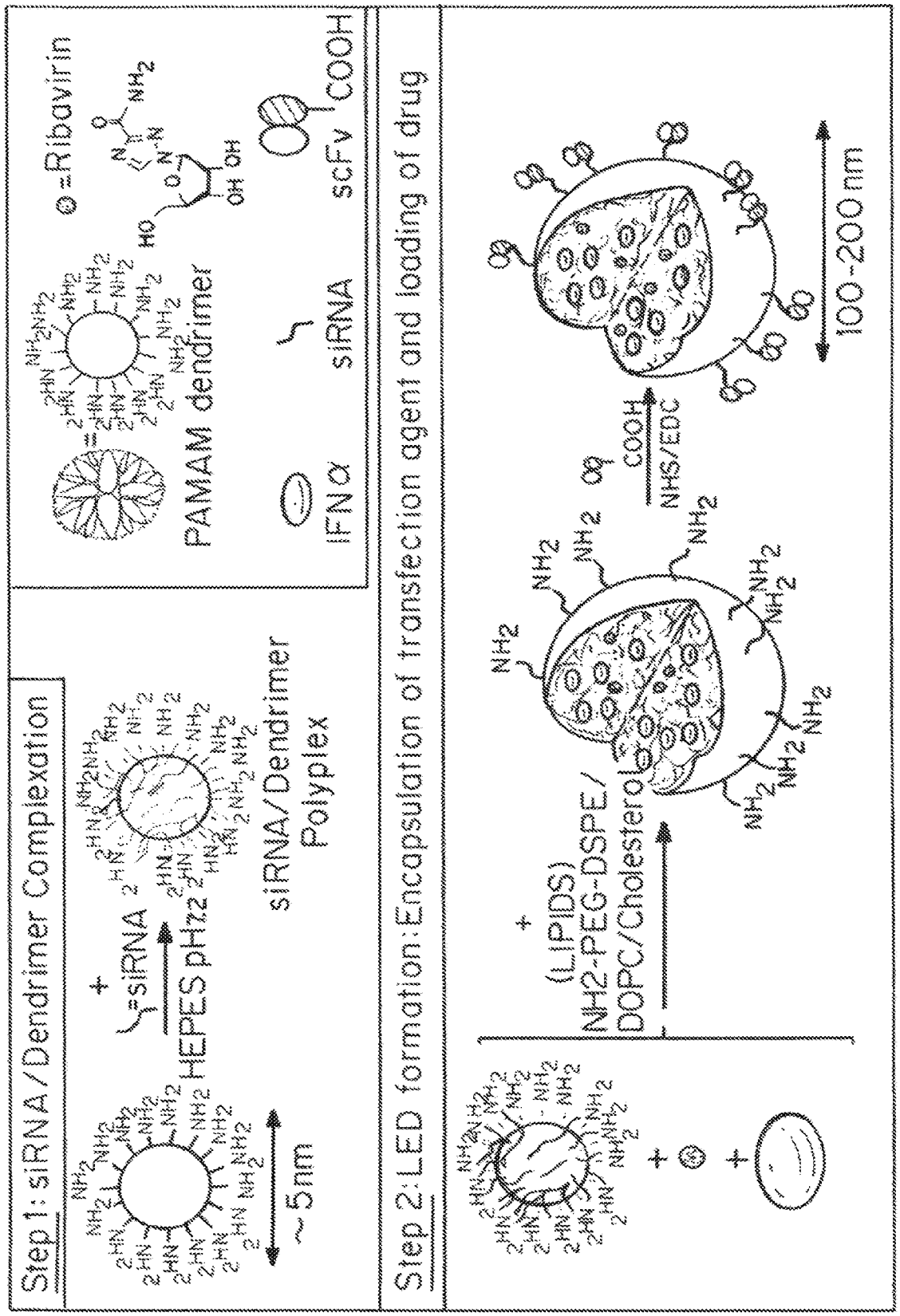
Figure 7B:
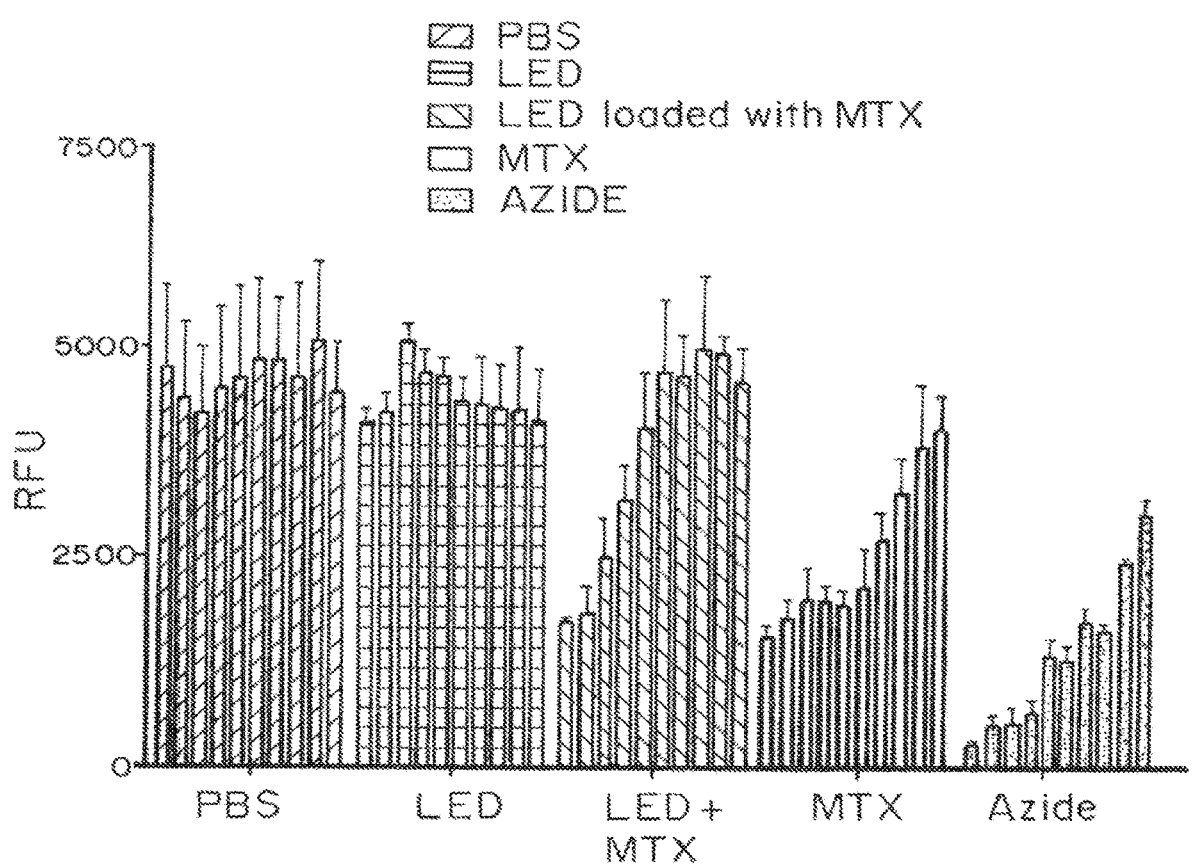
Figure 7C:
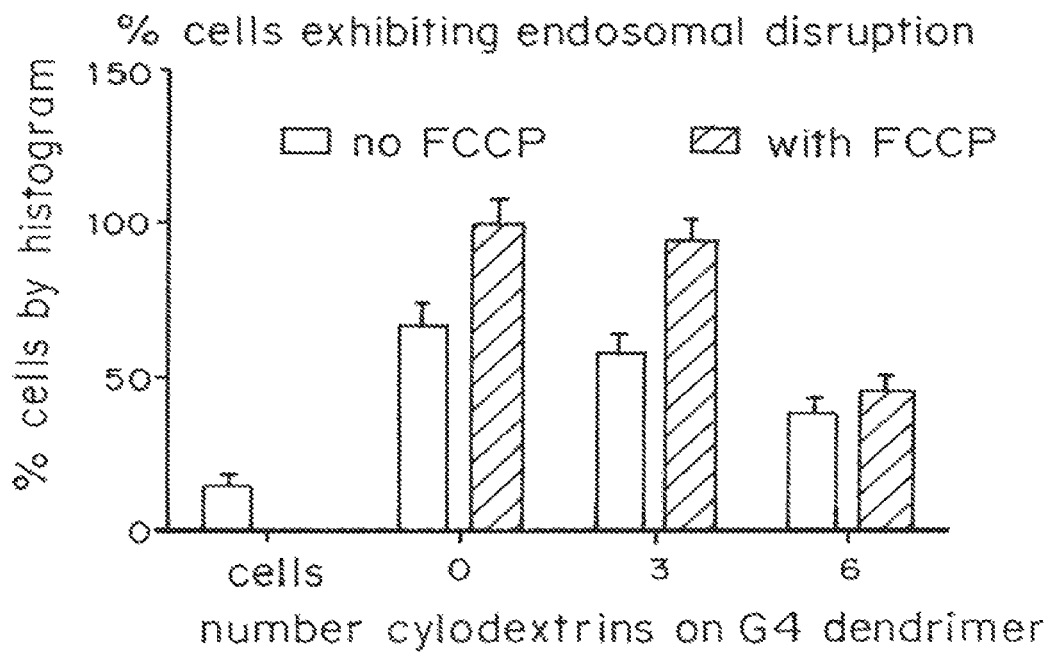
Figure 7D:
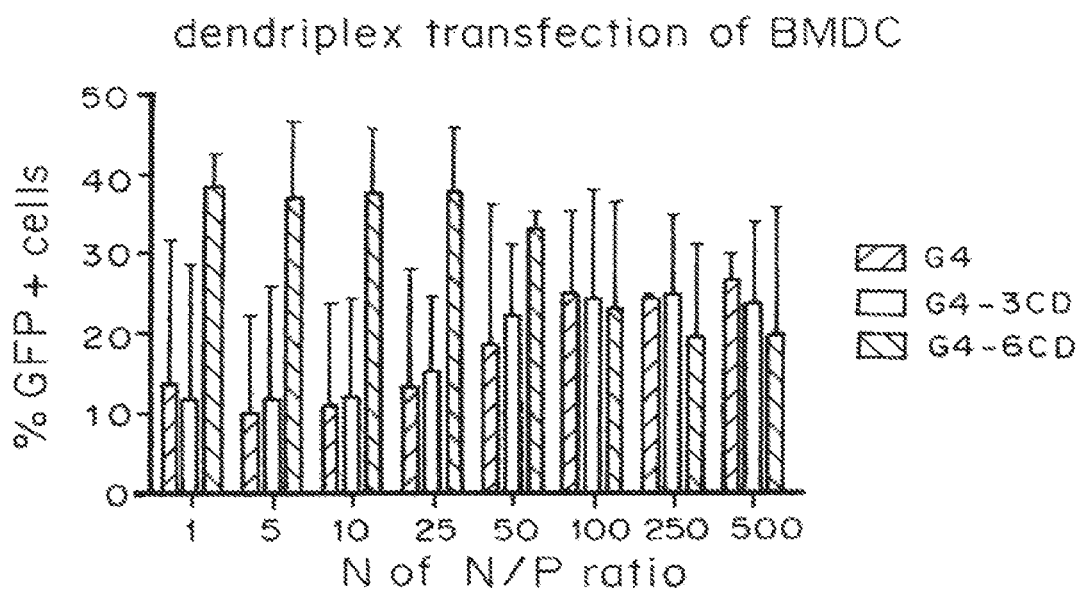
Figure 7E:
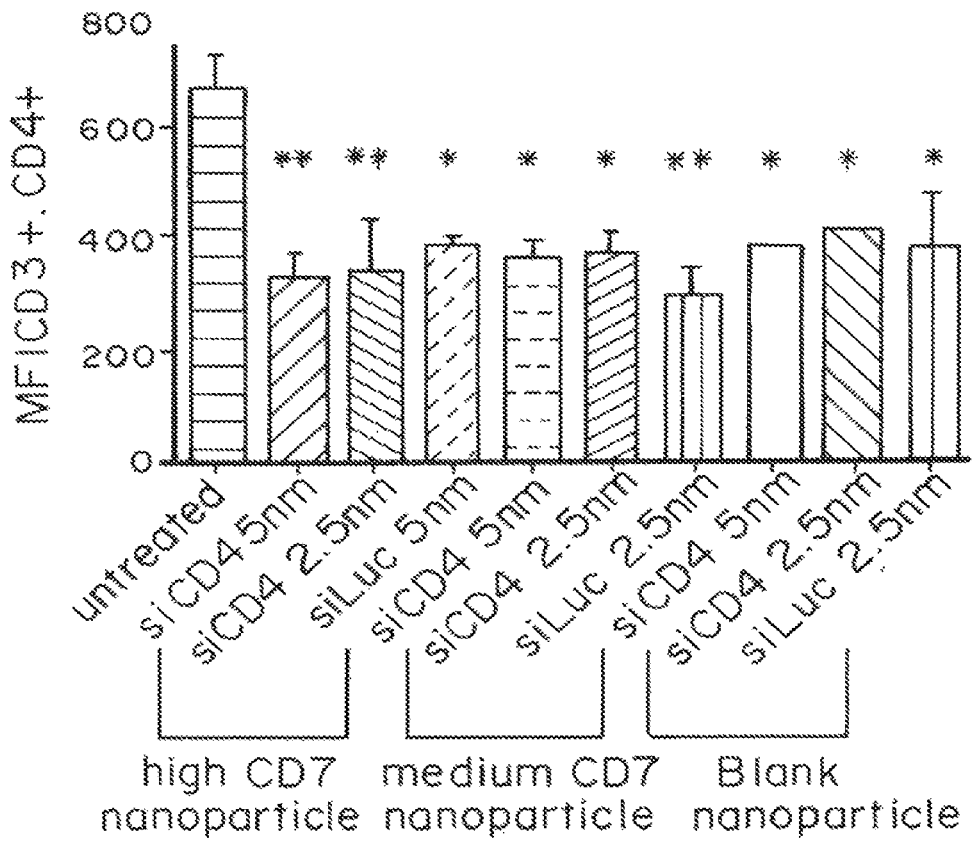
Figure 7F:
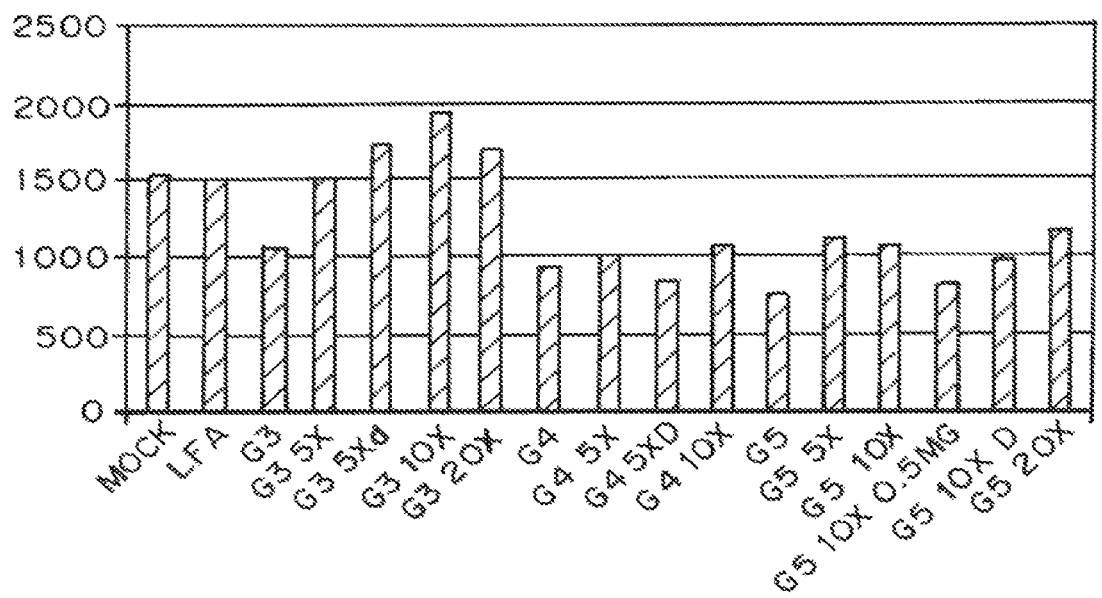
Figure 8A:
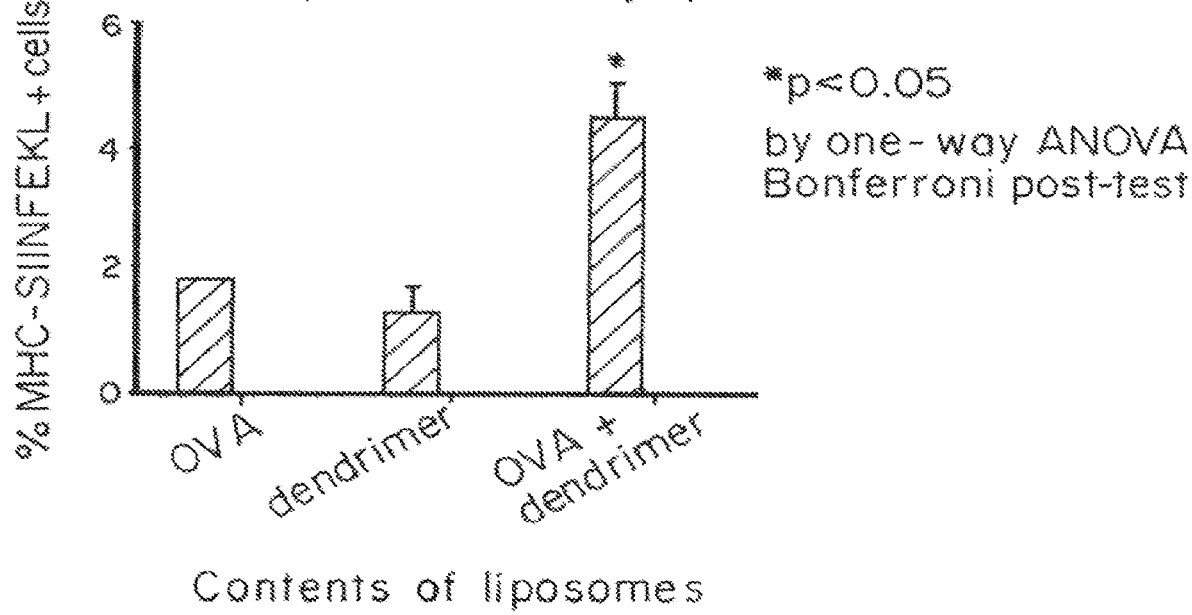
Figure 8B:
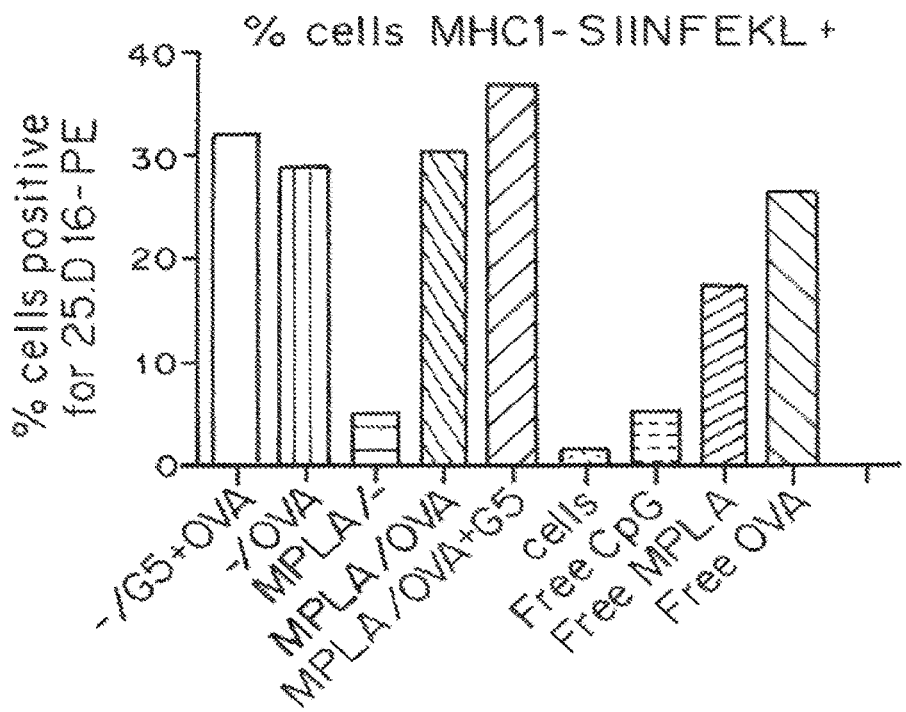
Figure 8C:
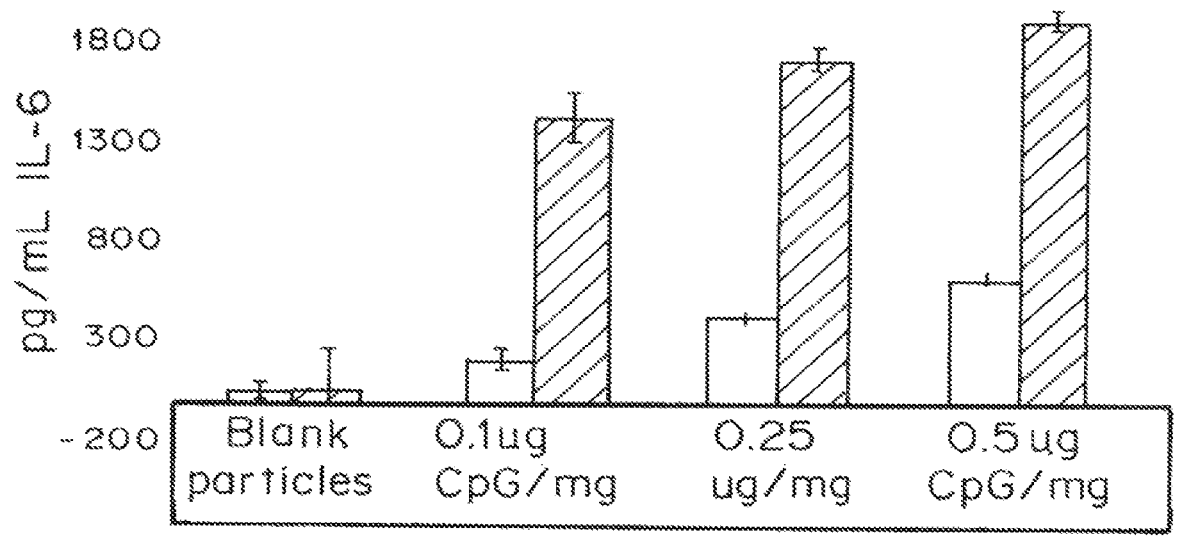

FIG. 7A is a schematic of LED preparation encapsulating siRNA/Dendrimer polyplex and drug combinations, with covalent modification of the Outer Shell with targeting antibodies or single chain variable fragments (scFv). FIG. 7B is a graph of the cytotoxicity of LED and LED encapsulating the model drug methotrexate (MTX). Bars indicate successive dilutions of LED or drug or combinations from 1 mg/ml to 10 μg/ml. Azide is used as a positive control for cell killing. FIG. 7C is a bar graph showing the % cells exhibiting endosomal disruption following treatment with unmodified generation 4 PAMAM dendrimers (G4), or dendrimers conjugated to cyclodextrin molecules (CD) that substituted and shielded primary amines with or without FCCIP, a small molecule ionophore, carbonylcyanide p-trifluoromethoxyphenylhydrazone. FIG. 7D is a bar graph showing the number of GFP positive cells as a percent of total cells transfected with pGFP using various LEDs (G4, 04-3CD, 04-6CD) at various N/P ratios. FIG. 7E is a bar graph showing relative number of MFICD3+, CD4+ cells control and various LEDs encapsulating different dosages of CD4 or Luciferase siRNA constructs. FIG. 7F is a bar graph showing the level of GFP expression in 293T cells stably transfected with eGFP following transfection of an siGFP construct using LIPOFECTAMINE® or various LEDs containing combinations of different dendrimer (G)-cyclodextrin conjugates (CDs). This graph measures the mean fluorescence intensity (MFI) of GFP to assess silencing ability of modified dendrimers complexed with siGFP. The x-axis should read as follows:

mock: nonsense siRNA
LFA: control siRNA against LFA
G3: unmodified generation 3 PAMAM dendrimer
G3 5x: G3 dendrimer with 1 cyclodextrin conjugated (G3-1CD)
G3 5xd: 03 with 2 CD conjugated (G3-2CD)
G3 10x: G3 with 3 CD conjugated (G3-3CD)
G3 20x: G3 with 3.4 CD conjugated (G3-3.4CD)
G4: G4 dendrimer with no modifications (G4)
G4 5x: G4 dendrimer with 1 CD conjugated (G4-1CD)
G4 5xd: G4 dendrimer with 1.3 CD conjugated (G4-1.3CD)
G4 10x: G4-3CD
G5: generation 5 (G5) dendrimer with no modifications
G5 5x: G5-1CD
G5 10x: G5-3CD
G5 10x0.5 mg: G5-3CD, 500 ug used instead of 200 μg in other treatments
G5 10xD: G5-2.5CD
G5 20x: G5-4CD FIG. 8A is a bar graph showing the % MHC-SIINFEKL, murine bone-marrow-derived dendritic cells (BMDCs). MHC-SINFEKL positive cells following treatment with liposomes containing ovalbumin alone (OVA), dendrimer alone (OVA), or a combination of OVA and dendrimer. * p<0.05 by one-way ANOVA Bonferroni post-test. FIG. 8B is a bar graph showing the % MIHC-SINFEKL positive cells (by 25.D16-PE staining) with various controls and liposomes including one or more of dendrimer (i.e., G5), antigen (i.e., ovalbumin (OVA)), and surface modifications (i.e., MPLA, and/or CpG) as labeled. The particle formulation containing MPLA, OVA, G5, and CpG was not shown since it encapsulated a prohibitively low amount of OVA protein, and normalizing treatment groups by the amount of OVA resulted in cell toxicity because the particle concentration was higher than other groups. FIG. 8C is a bar graph showing the IL-6 (pg/nL) expressed from bone marrow dendritic cells (BMDC) treated with LED presenting increasing amounts of CpG.

DETAILED DESCRIPTION OF THE INVENTION

I. Definitions

"Nanolipogel," as used herein, refers to a core-shell nanoparticle having a polymer matrix core, which can contain a host molecule, within a liposomal shell, which may be unilamellar or bilamellar, optionally crosslinked.

"Host molecule," as used herein, refers to a molecule or material which reversibly associates with an active agent to form a complex. In particular embodiments, the host is a molecule that forms an inclusion complex with an active agent. Inclusion complexes are formed when an active agent (i.e., the guest) or portion of an active agent inserts into a cavity of another molecule, group of molecules, or material (i.e., the host). The host may be a small molecule, an oligomer, a polymer, or combinations thereof. Exemplary hosts include polysaccharides such as amyloses, cyclodextrins, and other cyclic or helical compounds containing a plurality of aldose rings, for example, compounds formed through 1.4 and 1.6 bonding of monosaccharides (such as glucose, fructose, and galactose) and disaccharides (such as sucrose, maltose, and lactose). Other exemplary host compounds include cryptands, cryptophanes, cavitands, crown ethers, dendrimers, ion-exchange resins, calixarenes, valinomycins, nigericins, catenanes, polycatenanes, carcerands, cucurbiturils, and spherands.

"Small molecule," as used herein, refers to molecules with a molecular weight of less than about 2000 g/mol, more preferably less than about 1500 g/mol, most preferably less than about 1200 g/mol.

"Hydrogel," as used herein, refers to a water-swellable polymeric matrix formed from a three-dimensional network of macromolecules held together by covalent or non-covalent crosslinks, that can absorb a substantial amount of water (by weight) to form a gel.

"Nanoparticle", as used herein, generally refers to a particle having a diameter from about 10 nm up to, but not including, about 1 micron, preferably from 100 nm to about 1 micron. The particles can have any shape. Nanoparticles having a spherical shape are generally referred to as "nanospheres".

"Molecular weight" as used herein, generally refers to the relative average chain length of the bulk polymer, unless otherwise specified. In practice, molecular weight can be estimated or characterized using various methods including gel permeation chromatography (GPC) or capillary viscometry. GPC molecular weights are reported as the weight-average molecular weight (Mw) as opposed to the number-average molecular weight (Mn). Capillary viscometry provides estimates of molecular weight as the inherent viscosity determined from a dilute polymer solution using a particular set of concentration, temperature, and solvent conditions.

"Mean particle size" as used herein, generally refers to the statistical mean particle size (diameter) of the particles in a population of particles. The diameter of an essentially spherical particle may refer to the physical or hydrodynamic diameter. The diameter of a non-spherical particle may refer preferentially to the hydrodynamic diameter. As used herein, the diameter of a non-spherical particle may refer to the largest linear distance between two points on the surface of the particle. Mean particle size can be measured using methods known in the art, such as dynamic light scattering.

"Monodisperse" and "homogeneous size distribution", are used interchangeably herein and describe a population of nanoparticles or microparticles where all of the particles are the same or nearly the same size. As used herein, a monodisperse distribution refers to particle distributions in which 90% of the distribution lies within 15% of the median particle size, more preferably within 10% of the median particle size, most preferably within 5% of the median particle size.

"Active Agent", as used herein, refers to a physiologically or pharmacologically active substance that acts locally and/or systemically in the body. An active agent is a substance that is administered to a patient for the treatment (e.g., therapeutic agent), prevention (e.g., prophylactic agent), or diagnosis (e.g., diagnostic agent) of a disease or disorder.

II. Nanolipogels

Nanolipogels are core-shell nanoparticulates that combine the advantages of both liposomes and polymer-based particles for sustained delivery of active agents. As discussed in more detail below, typically, the outer shell protects cargo, provides biocompatibility and a surface for functionalization with targeting molecule(s). The outer shell encapsulates components so they are not exposed until desired, for example, in response to environmental conditions or stimuli, creating monodisperse, reproducible particle populations, and mediating internalization into desired cell types. The inner core, which can be a dendrimer or other polymer, has separate and additive functionalities to outer shell. For example, the inner shell allows for secondary deposition of drug, vaccine, or imaging agent; increases loading of components with different physiochemical properties into the particle; allows for tunable release of contents from particles; increases cytosolic availability of DNA/RNA, drug, and/or protein by disrupting endosomes, all leading to enhanced drug effects, antigen presentation, and transfection/silencing.

Nanolipogels have a polymer matrix core containing one or more host molecules. The polymeric matrix is preferably a hydrogel, such as a crosslinked block copolymer containing one or more poly(alkylene oxide) segments, such as polyethylene glycol, and one or more aliphatic polyester segments, such as polylactic acid. One or more host molecules, such as a cyclodextrin, dendrimer, or ion exchange resin, is dispersed within or covalently bound to the polymeric matrix. The hydrogel core is surrounded by a liposomal shell.

Nanolipogels can be constructed to incorporate a variety of active agents that can subsequently be released in a controlled fashion. Active agents can be dispersed within the hydrogel matrix, associated with one or more host molecules, dispersed within the liposomal shell, covalently attached to the liposomal shell; and combinations thereof. Active agents can be selectively incorporated at each of these locales within the nanolipogel. Furthermore, the release rate of active agents from each of these locales can be independently tuned. Because each of these locales possesses distinct properties, including size and hydrophobicity/hydrophilicity, the chemical entities independently incorporated at each of these locales can differ dramatically with respect to size and composition. For example, nanolipogels can be loaded with one or more proteins dispersed within the polymeric matrix as well as small molecule hydrophobic drugs associated with host molecules.

In this way, nanolipogels can provide simultaneous sustained release of agents that differ widely in chemical composition and molecular weight. In a non-limiting example, nanolipogels may be loaded with both a hydrophobic, small molecule antigen associated with a host molecule and an immunoadjuvant, such as an immunostimulatory protein, dispersed within the polymeric matrix. These nanolipogels can provide sustained release of the antigen together with the adjuvant, so as to optimize an immune response. In a particular example, simultaneous sustained delivery by nanolipogels of an immunostimulatory protein, Interleukin-2 (IL-2), as well as a low molecular weight organic molecule, 2-(5-benzo[1,3]dioxol-5-yl-2-tert-butyl-3H-imidazol-4-yl)-6-methylpyridine hydrochloride, an inhibitor of transforming growth factor-β (TGF-β), is achieved. This construct leads to an anti-tumor response in a murine system that is far superior to that achievable with the administration in solution of either agent alone or a combination of the two. Additionally, nanolipogels can favorably modulate biodistribution of one or more active agents encapsulated therein.

Nanolipogels are typically spherical in shape, with average particle sizes ranging between about 50 nm and about 1000 nm, more preferably between about 75 nm and about 300 nm, most preferably between about 90 nm and about 200 nm. In certain embodiments, the nanolipogels possess an average particle size between about 100 nm and about 140 nm. Particles may be non-spherical.

Depending upon the nature of the lipids present in the liposomal shell of the nanolipogels, nanolipogels having a positive, negative, or near neutral surface charge may be prepared. In certain embodiments, the nanolipogels possess a near neutral surface charge. In certain embodiments, the nanolipogels possess a ζ-potential of between about 10 mV and about −10 mV, more preferably between about 5 mV and about −5 mV, more preferably between about 3 mV and about −3 mV, most preferably between about 2 mV and about −2 mV.

A. Core

The nanolipogel core is formed from a polymeric matrix and one or more host molecules. The nanolipogel core may further include one or more active agents. The active agents may be complexed to the host molecules, dispersed with polymeric matrix, or combinations thereof.

1. Polymeric Matrix

The polymeric matrix of the nanolipogels may be formed from one or more polymers or copolymers. By varying the composition and morphology of the polymeric matrix, one can achieve a variety of controlled release characteristics, permitting the delivery of moderate constant doses of one or more active agents over prolonged periods of time.

The polymeric matrix may be formed from non-biodegradable or biodegradable polymers; however, preferably, the polymeric matrix is biodegradable. The polymeric matrix can be selected to degrade over a time period ranging from one day to one year, more preferably from seven days to 26 weeks, more preferably from seven days to 20 weeks, most preferably from seven days to 16 weeks.

In general, synthetic polymers are preferred, although natural polymers may be used. Representative polymers include poly(lactic acid), poly(glycolic acid), poly(lactic acid-co-glycolic acids), polyhydroxyalkanoates such as poly3-hydroxybutyrate or poly4-hydroxybutyrate; polycaprolactones; poly(orthoesters); polyanhydrides; poly(phosphazenes); poly(lactide-co-caprolactones); poly(glycolide-co-caprolactones); polycarbonates such as tyrosine polycarbonates; polyamides (including synthetic and natural polyamides), polypeptides, and poly(amino acids); polyesteramides; other biocompatible polyesters; poly(dioxanones); poly(alkylene alkylates); hydrophilic polyethers; polyurethanes; polyetheresters; polyacetals; polycyanoacrylates; polysiloxanes; poly(oxyethylene)/poly(oxypropylene) copolymers; polyketals; polyphosphates; polyhydroxyvalerates; polyalkylene oxalates; polyalkylene succinates; poly(maleic acids), polyvinyl alcohols, polyvinylpyrrolidone; poly(alkylene oxides) such as polyethylene glycol (PEG); derivativized celluloses such as alkyl celluloses (e.g., methyl cellulose), hydroxyalkyl celluloses (e.g., hydroxypropyl cellulose), cellulose ethers, cellulose esters, nitrocelluloses, polymers of acrylic acid, methacrylic acid or copolymers or derivatives thereof including esters, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate) (jointly referred to herein as "polyacrylic acids"), as well as derivatives, copolymers, and blends thereof.

As used herein, "derivatives" include polymers having substitutions, additions of chemical groups and other modifications to the polymeric backbones described above routinely made by those skilled in the art. Natural polymers, including proteins such as albumin, collagen, gelatin, prolamines, such as zein, and polysaccharides such as alginate and pectin, may also be incorporated into the polymeric matrix. While a variety of polymers may be used to form the polymeric matrix, generally, the resulting polymeric matrix will be a hydrogel. In certain cases, when the polymeric matrix contains a natural polymer, the natural polymer is a biopolymer which degrades by hydrolysis, such as a polyhydroxyalkanoate.

In preferred embodiments, the polymeric matrix contains one or more crosslinkable polymers. Preferably, the crosslinkable polymers contain one or more photo-polymerizable groups, allowing for the crosslinking of the polymeric matrix following nanolipogel formation. Examples of suitable photo-polymerizable groups include vinyl groups, acrylate groups, methacrylate groups, and acrylamide groups. Photo-polymerizable groups, when present, may be incorporated within the backbone of the crosslinkable polymers, within one or more of the sidechains of the crosslinkable polymers, at one or more of the ends of the crosslinkable polymers, or combinations thereof.

The polymeric matrix may be formed from polymers having a variety of molecular weights, so as to form nanolipogels having properties, including drug release rates, optimal for specific applications. Generally, the polymers which make up the polymeric matrix possess average molecular weights of about 500 Da and 50 kDa. In cases where the polymeric matrix is formed from non-crosslinkable polymers, the polymers typically possess average molecular weights ranging between about 1 kDa and about 50 kDa, more preferably between about 1 kDa and about 70 kDa, most preferably between about 5 kDa and about 50 kDa. In cases where the polymeric matrix is formed from crosslinkable polymers, the polymers typically possess lower average molecular weights ranging between about 500 Da and about 25 kDa, more preferably between about 1 kDa and about 10 kDa, most preferably between about 3 kDa and about 6 kDa. In particular embodiments the polymeric matrix is formed from a crosslinkable polymer having an average molecular weight of about 5 kDa.

In some embodiments, the polymeric matrix is formed from a poly(alkylene oxide) polymer or a block copolymer containing one or more poly(alkylene oxide) segments. The poly(alkylene oxide) polymer or poly(alkylene oxide) polymer segments may contain between 8 and 500 repeat units, more preferably between 40 and 300 repeat units, most preferably between 50 and 150 repeat units. Suitable poly(alkylene oxides) include polyethylene glycol (also referred to as polyethylene oxide or PEG), polypropylene 1,2-glycol, poly(propylene oxide), polypropylene 1,3-glycol, and copolymers thereof.

In some embodiments, the polymeric matrix is formed from an aliphatic polyester or a block copolymer containing one or more aliphatic polyester segments. Preferably the polyester or polyester segments are poly(lactic acid) (PLA), poly(glycolic acid) PGA, or poly(lactide-co-glycolide) (PLGA).

In preferred embodiments, the polymeric matrix is formed from a block copolymer containing one or more poly(alkylene oxide) segments, one or more aliphatic polyester segments, and optionally one or more photo-polymerizable groups. In these cases, the one or more poly(alkylene oxide) segments imbue the polymer with the necessary hydrophilicity, such that the resultant polymer matrix forms a suitable hydrogel, while the polyester segments provide a polymeric matrix with tunable hydrophobicity/hydrophilicity and/or the desired in vivo degradation characteristics.

The degradation rate of the polyester segments, and often the corresponding drug release rate, can be varied from days (in the case of pure PGA) to months (in the case of pure PLA), and may be readily manipulated by varying the ratio of PLA to PGA in the polyester segments. In addition, the poly(alkylene oxides), such as PEG, and aliphatic polyesters, such as PGA, PLA, and PLGA have been established as safe for use in humans; these materials have been used in human clinical applications, including drug delivery system, for more than 30 years.

In certain embodiments, the polymeric matrix is formed from a tri-block copolymer containing a central poly(alkylene oxide) segment, adjoining aliphatic polyester segments attached to either end of the central poly(alkylene oxide) segment, and one or more photo-polymerizable groups. Preferably, the central poly(alkylene oxide) segment is PEG, and aliphatic polyesters segments are PGA, PLA, or PLGA.

Generally, the average molecular weight of the central poly(alkylene oxide) segment is greater than the average molecular weight of the adjoining polyester segments. In certain embodiments, the average molecular weight of the central poly(alkylene oxide) segment is at least three times greater than the average molecular weight of one of the adjoining polyester segments, more preferably at least five times greater than the average molecular weight of one of the adjoining polyester segments, most preferably at least ten times greater than the average molecular weight of one of the adjoining polyester segments.

In some cases, the central poly(alkylene oxide) segment possesses an average molecular weight ranging between about 500 Da and about 10,000 Da, more preferably between about 1,000 Da and about 7,000 Da, most preferably between about 2,500 Da and about 5,000 Da. In particular embodiments, average molecular weight of the central poly(alkylene oxide) segment is about 4,000 Da. Typically, each adjoining polyester segment possesses an average molecular weight ranging between about 100 Da and about 3,500 Da, more preferably between about 100 Da and about 1,000 Da, most preferably between about 100 Da and about 500 Da.

In a preferred embodiment, the polymeric matrix is formed from the tri-block copolymer shown below

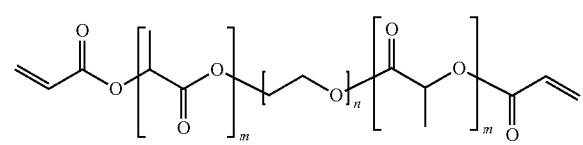

where m and n are, independently for each occurrence, integers between 1 and 500, more preferably between 10 and 150.

Examples of preferred natural polymers include proteins such as albumin, collagen, gelatin and prolamines, for example, zein, and polysaccharides such as alginate, cellulose derivatives and polyhydroxyalkanoates, for example, polyhydroxybutyrate. The in vivo stability of the microparticles can be adjusted during the production by using polymers such as poly(lactide-co-glycolide) copolymerized with polyethylene glycol (PEG). If PEG is exposed on the external surface, it may increase the time these materials circulate due to the hydrophilicity of PEG.

Examples of preferred non-biodegradable polymers include ethylene vinyl acetate, poly(meth)acrylic acid, polyamides, copolymers and mixtures thereof.

The matrix can also be made of gel-type polymers, such as alginate, produced through traditional ionic gelation techniques. The polymers are first dissolved in an aqueous solution, mixed with barium sulfate or some bioactive agent, and then extruded through a microdroplet forming device, which in some instances employs a flow of nitrogen gas to break off the droplet. A slowly stirred (approximately 100-170 RPM) ionic hardening bath is positioned below the extruding device to catch the forming microdroplets. The microparticles are left to incubate in the bath for twenty to thirty minutes in order to allow sufficient time for gelation to occur. Microparticle particle size is controlled by using various size extruders or varying either the nitrogen gas or polymer solution flow rates. Chitosan microparticles can be prepared by dissolving the polymer in acidic solution and crosslinking it with tripolyphosphate. Carboxymethyl cellulose (CMC) microparticles can be prepared by dissolving the polymer in acid solution and precipitating the microparticle with lead ions. In the case of negatively charged polymers (e.g., alginate, CMC), positively charged ligands (e.g., polylysine, polyethyleneimine) of different molecular weights can be ionically attached.

Perhaps the most widely used are the aliphatic polyesters, specifically the hydrophobic poly(lactic acid) (PLA), more hydrophilic poly(glycolic acid) PGA and their copolymers, poly(lactide-co-glycolide) (PLGA). The degradation rate of these polymers, and often the corresponding drug release rate, can vary from days (PGA) to months (PLA) and is easily manipulated by varying the ratio of PLA to PGA. Second, the physiologic compatibility of PLGA and its hompolymers PGA and PLA have been established for safe use in humans; these materials have a history of over 30 years in various human clinical applications including drug delivery systems. PLGA nanoparticles can be formulated in a variety of ways that improve drug pharmacokinetics and biodistribution to target tissue by either passive or active targeting. The microparticles are designed to release molecules to be encapsulated or attached over a period of days to weeks. Factors that affect the duration of release include pH of the surrounding medium (higher rate of release at pH 5 and below due to acid catalyzed hydrolysis of PLGA) and polymer composition. Aliphatic polyesters differ in hydrophobicity and that in turn affects the degradation rate. Specifically the hydrophobic poly(lactic acid) (PLA), more hydrophilic poly (glycolic acid) PGA and their copolymers, poly(lactide-co-glycolide) (PLGA) have various release rates. The degradation rate of these polymers, and often the corresponding drug release rate, can vary from days (PGA) to months (PLA) and is easily manipulated by varying the ratio of PLA to PGA.

2. Host Molecules

Host molecules are molecules or materials which reversibly associate with an active agent to form a complex. By virtue of their ability to reversibly form complexes with active agents, host molecules can function to control the release of a complexed active agent in vivo.

In some cases, the host molecule is a molecule that forms an inclusion complex with an active agent. Inclusion complexes are formed when an active agent (i.e., the guest) or portion of an active agent inserts into a cavity of another molecule, group of molecules, or material (i.e., the host). Typically, the guest molecule associates with the host molecule without affecting the framework or structure of the host. For example, in the case of inclusion complexes, the size and shape of the available cavity in the host molecule remain substantially unaltered as a consequence of complex formation.

The host molecule may be a small molecule, an oligomer, a polymer, or combinations thereof. Exemplary hosts include polysaccharides such as amyloses, cyclodextrins, and other cyclic or helical compounds containing a plurality of aldose rings, for example, compounds formed through 1.4 and 1.6 bonding of monosaccharides (such as glucose, fructose, and galactose) and disaccharides (such as sucrose, maltose, and lactose). Other exemplary host compounds include cryptands, cryptophanes, cavitands, crown ethers, dendrimers, ion-exchange resins, calixarenes, valinomycins, nigericins, catenanes, polycatenanes, carcerands, cucurbiturils, and spherands.

In still other embodiments, organic host compounds or materials include carbon nanotubes, fullerenes, and/or grapheme-based host materials. Carbon nanotubes (CNTs) are allotropes of carbon with a cylindrical nanostructure. Nanotubes are members of the fullerene structural family, which also includes the spherical buckyballs, and the ends of a nanotube may be capped with a hemisphere of the buckyball structure. Their name is derived from their long, hollow structure with the walls formed by one-atom-thick sheets of carbon, called graphene. These sheets are rolled at specific and discrete ("chiral") angles, and the combination of the rolling angle and radius decides the nanotube properties. Nanotubes can be categorized as single-walled nanotubes (SWNTs) and multi-walled nanotubes (MWNTs). Nanotubes and/or fullerenes can serve as hosts, for example, by encapsulating or entrapping the material to be delivered (i.e., the guest) within the tubes or fullerenes. Alternatively, the exterior and/or interior of the tubes and/or fullerenes can be functionalized with functional groups which can complex to the guest to be delivered. Complexations include, but are not limited to, ionic interactions, hydrogen bonding, Van der Waals interactions, and pi-pi interactions, such as pi-stacking.

Graphenes are also an allotrope of carbon. The structure of graphene is a one-atom-thick planar sheet of sp-bonded carbon atoms that are densely packed in a honeycomb crystal lattice. Graphene is the basic structural element of some carbon allotropes including graphite, charcoal, carbon nanotubes and fullerenes. The guest to be delivered can associate with and/or complex to graphene or functionalized graphene as described above for nanotubes and fullerenes.

The host material can also be an inorganic material, including but not limited to, inorganic phosphates and silica.

Suitable host molecules are generally selected for incorporation into nanolipogels in view of the identity of the active agent(s) to be delivered and the desired drug release profile. In order to form a complex with the active agent being delivered, the host molecule is generally selected to be complimentary to the active agent both in terms of sterics (size) and electronics (charge and polarity). For example, in the case of host molecules that form inclusion complexes with the active agent to be delivered, the host molecule will typically possess an appropriately-sized cavity to incorporate the active agent. In addition, the host molecule typically possesses a cavity of appropriate hydrophobicity/hydrophilicity to promote complex formation with the active agent. The strength of the guest-host interaction will influence the drug release profile of the active agent from the nanolipogel, with stronger guest-host interactions generally producing more prolonged drug release.

Generally, the host molecules are dispersed within the polymeric matrix that forms the nanolipogel core. In some cases, one or more host molecules are covalently coupled to the polymeric matrix. For example, the host molecules may be functionalized with one or more pendant reactive functional groups that react with the polymer matrix. In particular embodiments, the host molecules contain one or more pendant reactive functional groups that react with the polymer matrix to crosslink the polymer matrix. Examples of suitable reactive functional groups include methacrylates, acrylates, vinyl groups, epoxides, thiiranes, azides, and alkynes.

In certain embodiments, the host molecule is a cyclodextrin. Cyclodextrins are cyclic oligosaccharides containing six ($\alpha$-cyclodextrin), seven ($\beta$-cyclodextrin), eight ($\gamma$-cyclodextrin), or more $\alpha$-(1,4)-linked glucose residues. The hydroxyl groups of the cyclodextrins are oriented to the outside of the ring while the glucosidic oxygen and two rings of the non-exchangeable hydrogen atoms are directed towards the interior of the cavity. As a result, cyclodextrins possess a hydrophobic inner cavity combined with a hydrophilic exterior. Upon combination with a hydrophobic active agent, the active agent (i.e., the guest) inserts into the hydrophobic interior of the cyclodextrin (i.e., the host).

The cyclodextrin may be chemically modified such that some or all of the primary or secondary hydroxyl groups of the macrocycle, or both, are functionalized with one or more pendant groups. The pendant groups may be reactive functional groups that can react with the polymeric matrix, such as methacrylates, acrylates, vinyl groups, epoxides, thiiranes, azides, alkynes, and combinations thereof. The pendant groups may also serve to modify the solubility of the cyclodextrin. Exemplary groups of this type include sulfinyl, sulfonyl, phosphate, acyl, and $C_1$-$C_{12}$ alkyl groups optionally substituted with one or more (e.g., 1, 2, 3, or 4) hydroxy, carboxy, carbonyl, acyl, oxy, and oxo groups. Methods of modifying these alcohol residues are known in the art, and many cyclodextrin derivatives are commercially available.

Examples of suitable cyclodextrins include $\alpha$-cyclodextrin; $\beta$-cyclodextrin; $\gamma$-cyclodextrin; methyl $\alpha$-cyclodextrin; methyl $\beta$-cyclodextrin; methyl $\gamma$-cyclodextrin; ethyl $\beta$-cyclodextrin; butyl $\alpha$-cyclodextrin; butyl $\beta$-cyclodextrin; butyl $\gamma$-cyclodextrin; pentyl $\gamma$-cyclodextrin; hydroxyethyl $\beta$-cyclodextrin; hydroxyethyl $\gamma$-cyclodextrin; 2-hydroxypropyl $\alpha$-cyclodextrin; 2-hydroxypropyl $\beta$-cyclodextrin; 2-hydroxypropyl $\gamma$-cyclodextrin; 2-hydroxybutyl $\beta$-cyclodextrin; acetyl $\alpha$-cyclodextrin; acetyl $\beta$-cyclodextrin; acetyl $\gamma$-cyclodextrin; propionyl $\beta$-cyclodextrin; butyryl $\beta$-cyclodextrin; succinyl $\alpha$-cyclodextrin; succinyl $\beta$-cyclodextrin; succinyl $\gamma$-cyclodextrin; benzoyl $\beta$-cyclodextrin; palmityl $\beta$-cyclodextrin; toluenesulfonyl $\beta$-cyclodextrin; acetyl methyl $\beta$-cyclodextrin; acetyl butyl $\beta$-cyclodextrin; glucosyl $\alpha$-cyclodextrin; glucosyl $\beta$-cyclodextrin; glucosyl $\gamma$-cyclodextrin; maltosyl $\alpha$-cyclodextrin; maltosyl $\beta$-cyclodextrin; maltosyl $\gamma$-cyclodextrin; $\alpha$-cyclodextrin carboxymethylether; $\beta$-cyclodextrin carboxymethylether; γ-cyclodextrin carboxymethylether; carboxymethylethyl β-cyclodextria; phosphate ester α-cyclodextrin; phosphate ester β-cyclodextrin; phosphate ester γ-cyclodextrin; 3-trimethylammonium-2-hydroxypropyl β-cyclodextrin; sulfobutyl ether β-cyclodextrin; carboxymethyl α-cyclodextrin; carboxymethyl β-cyclodextrin; carboxymethyl γ-cyclodextrin, and combinations thereof.

Preferred cyclodextrins include α-cyclodextrins, β-cyclodextrins, and γ-cyclodextrins functionalized with one or more pendant acrylate or methacrylate groups. In a particular embodiment, the host molecule is a β-cyclodextrin functionalized with multiple methacrylate groups. An exemplary host molecule of this type is illustrated below, wherein R represents a $C_1$-$C_6$ alkyl group.

cally associating with active agents, as described above. In addition, medium-sized dendrimers, such as three- and four-generation PAMAM dendrimers, may possess internal voids spaces which can accommodate active agents, for example, by complexation of nucleic acids.

In some embodiments the host molecule is a dendrimer conjugated to a cyclodextrin. In some embodiments, the cyclodextrin(s) shields primary amines of dendrimer. Suitable dendrimers and cyclodextrins are discussed above. Unmodified dendrimer (i.e., generation 4 PAMAM dendrimer (04)) was empirically better at endosomal disruption than dendrimer conjugated with cyclodexrin (CD) (See the Examples below). Without being bound by theory, it is believed that terminal amine groups on PAMAM dendrimers provide endosomal buffering and disrupt endosomes by the

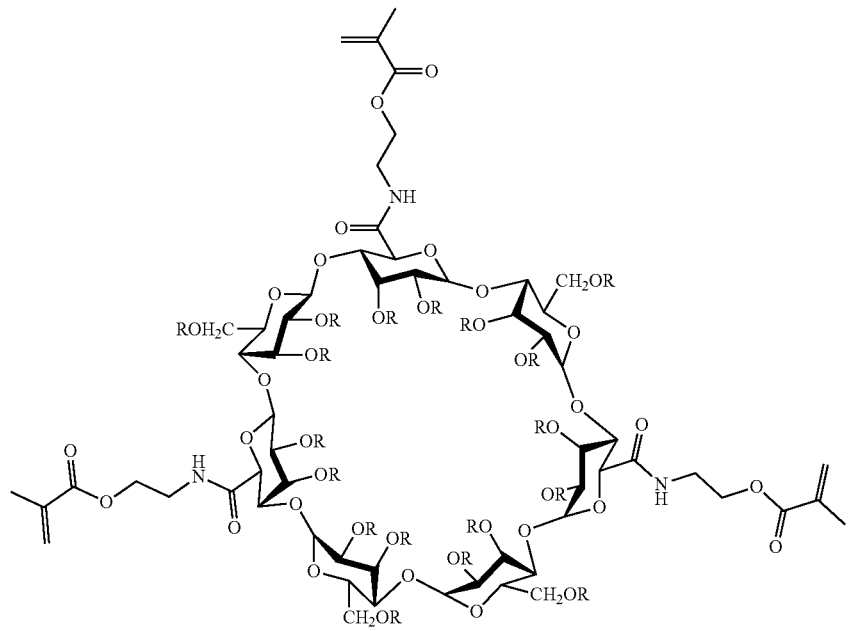

As a further example, the host molecule may also be a material that temporarily associates with an active agent via ionic interactions. For example, conventional ion exchange resins known in the art for use in controlled drug release may serve as host molecules. See, for example, Chen, et al. "Evaluation of ion-exchange microspheres as carriers for the anticancer drug doxorubicin: in vitro studies." *J. Pharm. Pharmacol.* 44(3):211-215 (1992) and Farag, et at "Rate of release of organic carboxylic acids from ion exchange resins" *J. Pharm. Sci.* 77(10):872-875(1988).

By way of exemplification, when the active agent being delivered is a cationic species, suitable ion exchange resins may include a sulfonic acid group (or modified sulfonic acid group) or an optionally modified carboxylic acid group on a physiologically acceptable scaffold. Similarly, where the active agent is an anionic species, suitable ion exchange resins may include amine-based groups (e.g., trimethylamine for a strong interaction, or dimethylethanolamine for a weaker interaction). Cationic polymers, such as polyethyleneimine (PEI), can function as host molecules for complex oligonucleotides such as siRNA.

In other cases, the host molecule is a dendrimer, such as a poly(amidoamine) (PAMAM) dendrimer. Cationic and anionic dendrimers can function as host materials by ioniproton sponge effect. Accordingly, increasing CD results in a decrease in endosomal disruption. As discussed in the Examples below, different combinations of dendrimers and cyclodextrins can be used to modulate the transfection efficiency and level of endosomal disruption in the cell.

Preferably, the one or more host molecules are present in an amount of from about 0.1% to about 40% w/w of the polymeric matrix, more preferably from about 0.1% to about 25% w/w of the overall formulation.

3. Active Agents

Active agents to be delivered include therapeutic, nutritional, diagnostic, and prophylactic agents. The active agents can be small molecule active agents or biomacromolecules, such as proteins, polypeptides, or nucleic acids. Suitable small molecule active agents include organic and organometallic compounds. The small molecule active agents can be a hydrophilic, hydrophobic, or amphiphilic compound.

Exemplary therapeutic agents that can be incorporated into nanolipogels include tumor antigens, CD4+ T-cell epitopes, cytokines, chemotherapeutic agents, radionuclides, small molecule signal transduction inhibitors, photothermal antennas, monoclonal antibodies, immunologic danger signaling molecules, other immunotherapeutics, enzymes, antibiotics, antivirals (especially protease inhibitors alone or in combination with nucleosides for treatment of HIV or Hepatitis B or C), anti-parasites (helminths, protozoans), growth factors, growth inhibitors, hormones, hormone antagonists, antibodies and bioactive fragments thereof (including humanized, single chain, and chimeric antibodies), antigen and vaccine formulations (including adjuvants), peptide drugs, anti-inflammatories, immunomodulators (including ligands that bind to Toll-Like Receptors (including but not limited to GpG oligonucleotides) to activate the innate immune system, molecules that mobilize and optimize the adaptive immune system, molecules that activate or up-regulate the action of cytotoxic T lymphocytes, natural killer cells and helper T-cells, and molecules that deactivate or down-regulate suppressor or regulatory T-cells), agents that promote uptake of nanolipogels into cells (including dendritic cells and other antigen-presenting cells), nutraceuticals such as vitamins, and oligonucleotide drugs (including DNA, RNAs, antisense, aptamers, small interfering RNAs, ribozymes, external guide sequences for ribonuclease P, and triplex forming agents).

Exemplary diagnostic agents include paramagnetic molecules, fluorescent compounds, magnetic molecules, and radionuclides, x-ray imaging agents, and contrast agents.

In certain embodiments, the nanolipogel includes one or more anti-cancer agents. Representative anti-cancer agents include, but are not limited to, alkylating agents (such as cisplatin, carboplatin, oxaliplatin, mechlorethamine, cyclophosphamide, chlorambucil, dacarbazine, lomustine, carmustine, procarbazine, chlorambucil and ifosfamide), antimetabolites (such as fluorouracil (5-FU), gemcitabine, methotrexate, cytosine arabinoside, fludarabine, and floxuridine), antimitotics (including taxanes such as paclitaxel and decetaxel and *vinca* alkaloids such as vincristine, vinblastine, vinorelbine, and vindesine), anthracyclines (including doxorubicin, daunorubicin, valrubicin, idarubicin, and epirubicin, as well as actinomycins such as actinomycin D), cytotoxic antibiotics (including mitomycin, plicamycin, and bleomycin), topoisomerase inhibitors (including camptothecins such as camptothecin, irinotecan, and topotecan as well as derivatives of epipodophyllotoxins such as amsacrine, etoposide, etoposide phosphate, and teniposide), antibodies to vascular endothelial growth factor (VEGF) such as bevacizumab (AVASTIN®), other anti-VEGF compounds; thalidomide (THALOMID®) and derivatives thereof such as lenalidomide (REVLIMID®); endostatin; angiostatin; receptor tyrosine kinase (RTK) inhibitors such as sunitinib (SUTENT®); tyrosine kinase inhibitors such as sorafenib (Nexavar®), erlotinib (Tarceva®), pazopanib, axitinib, and lapatinib; transforming growth factor-α or transforming growth factor-β inhibitors, and antibodies to the epidermal growth factor receptor such as panitumumab (VECTIBIX®) and cetuximab (ERBITUX®).

In certain embodiments, the nanolipogel includes one or more immunomodulatory agents. Exemplary immunomodulatory agents include cytokines, xantbines, interleukins, interferons, oligodeoxynucleotides, glucans, growth factors (e.g., TNF, CSF, GM-CSF and G-CSF), hormones such as estrogens (diethylstilbestrol, estradiol), androgens (testosterone, HALOTESTIN® (fluoxymesterone)), progestins (MEGACE® (megestrol acetate), PROVERA® (medroxyprogesterone acetate)), and corticosteroids (prednisone, dexamethasone, hydrocortisone).

Examples of immunological adjuvants that can be associated with the particles include, but are not limited to, TLR ligands, C-Type Lectin Receptor ligands, NOD-Like Receptor ligands, RLR ligands, and RAGE ligands. TLR ligands can include lipopolysaccharide (LPS) and derivatives thereof, as well as lipid A and derivatives there of including, but not limited to, monophosphoryl lipid A (MPL), glycopyranosyl lipid A, PET-lipid A, and 3-O-desacyl-4'-monophosphoryl lipid A. In a specific embodiment, the immunological adjuvant is MPL. In another embodiment, the immunological adjuvant is LPS. TLR ligands can also include, but are not limited to, TLR3 ligands (e.g., polyinosinic-polycytidylic acid (poly(I:C)), TLR7 ligands (e.g., imiquimod and resiquimod), and TLR9 ligands.

The nanolipogel may also include antigens and/or adjuvants (i.e., molecules enhancing an immune response). Peptide, protein, and DNA based vaccines may be used to induce immunity to various diseases or conditions. Cell-mediated immunity is needed to detect and destroy virus-infected cells. Most traditional vaccines (e.g. protein-based vaccines) can only induce humoral immunity. DNA-based vaccine represents a unique means to vaccinate against a virus or parasite because a DNA based vaccine can induce both humoral and cell-mediated immunity. In addition, DNA based vaccines are potentially safer than traditional vaccines. DNA vaccines are relatively more stable and more cost-effective for manufacturing and storage. DNA vaccines consist of two major components, DNA carriers (or delivery vehicles) and DNAs encoding antigens. DNA carriers protect DNA from degradation, and can facilitate DNA entry to specific tissues or cells and expression at an efficient level.

In certain embodiments, the nanolipogel core contains two or more active agents. In preferred embodiments, the nanolipogel core contains both a small molecule hydrophobic active agent, preferably associated with one or more suitable host molecules, and a hydrophilic active agent dispersed within the polymeric matrix. In particular embodiments, the hydrophilic active agent is a protein, such as a therapeutic cytokine. By incorporating a hydrophobic active agent in association with a host molecule and a hydrophilic molecule dispersed within the polymeric matrix, controlled release of two or more active agents, including two or more active agents with varied physiochemical characteristics (such as solubility, hydrophobicity/hydrophilicity, molecular weight, and combinations thereof) can be achieved.

In a preferred embodiment demonstrated by the examples, the host molecule is used to deliver a low molecular weight compounds such as a chemotherapeutic, where the host molecule retards release of the low molecular weight compound, and a larger hydrophilic compound, such as a cytokine, so that release of both molecules occurs over a similar time period.

B. Shell Components

Nanolipogels include a liposomal shell composed of one or more concentric lipid monolayers or lipid bilayers. The shell can further include one or active agents, targeting molecules, or combinations thereof.

1. Lipids

Nanolipogels include a liposomal shell composed of one or more concentric lipid monolayers or lipid bilayers. The composition of the liposomal shell may be varied to influence the release rate of one or more active agents in vivo. The lipids may also be covalently crosslinked, if desired, to alter in vivo drug release.

The lipid shell can be formed from a single lipid bilayer (i.e., the shell may be unilamellar) or several concentric lipid bilayers (i.e., the shell may be multilamellar). The lipid shell may be formed from a single lipid; however, in preferred embodiments, the lipid shell is formed from a combination of more than one lipid. The lipids can be neutral, anionic or cationic lipids at physiologic pH.

Suitable neutral and anionic lipids include sterols and lipids such as cholesterol, phospholipids, lysolipids, lysophospholipids, and sphingolipids. Neutral and anionic lipids include, but are not limited to, phosphatidylcholine (PC) (such as egg PC, soy PC), including 1,2-diacyl-glycero-3-phosphocholines; phosphatidylserine (PS), phosphatidylglycerol, phosphatidylinositol (PI); glycolipids; sphingophospholipids, such as sphingomyelin; sphingoglycolipids (also known as 1-ceramidyl glucosides), such as ceramide galactopyranoside, gangliosides and cerebrosides; fatty acids, sterols containing a carboxylic acid group such as cholesterol or derivatives thereof; and 1,2-diacyl-sn-glycero-3-phosphoethanolamines, including 1,2-dioleoyl-sn-Glycero-3-phosphoethanolamine or 1,2-dioleolylglyceryl phosphatidylethanolamine (DOPE), 1,2-dihexadecylphosphoethanolamine (DHPE), 1,2-distearoylphosphatidylcholine (DSPC), 1,2-dipalmitoylphosphatidylcholine (DPPC), and 1,2-dimyristoylphosphatidylcholine (DMPC). Also suitable are natural (e.g., tissue derived L-α-phosphatidyl: egg yolk, heart, brain, liver, soybean) and/or synthetic (e.g., saturated and unsaturated 1,2-diacyl-sn-glycero-3-phosphocholines, 1-acyl-2-acyl-sn-glycero-3-phosphocholines, 1,2-diheptanoyl-SN-glycero-3-phosphocholine) derivatives of these lipids.

Suitable cationic lipids include N-[1-(2,3-dioleoyloxy) propyl]-N,N,N-trimethyl ammonium salts, also referred to as TAP lipids, for example as a methylsulfate salt. Suitable TAP lipids include, but are not limited to, DOTAP (dioleoyl-), DMTAP (dimyristoyl-), DPTAP (dipalmitoyl-), and DSTAP (distearoyl-). Other suitable cationic lipids include dimethyldioctadecyl ammonium bromide (DDAB), 1,2-diacyloxy-3-trimethylammonium propanes, N-[1-(2,3-dioloyloxy)propyl]-N,N-dimethyl amine (DODAP), 1,2-diacyloxy-3-dimethylammonium propanes, N-[1-(2,3-dioleyloxy)propyl]-N,N,N-trimethylammonium chloride (DOTMA), 1,2-dialkyloxy-3-dimethylammonium propanes, dioctadecylamidoglycylspermine (DOGS), 3-[N—(N',N'-dimethylamino-ethane)carbamoyl]cholesterol (DC-Chol); 2,3-dioleoyloxy-N-(2-(speriniecarboxamido)-ethyl)-N,N-dimethyl-1-propanaminium trifluoro-acetate (DOSPA), β-alanyl cholesterol, cetyltrimethylammonium bromide (CTAB), $diC_{14}$-amidine, N-tert-butyl-N'-tetradecyl-3-tetradecylamino-propionamidine, N-(alpha-trimethylanmnonioacetyl)didodecyl-D-glutamate chloride (TMAG), ditetradecanoyl-N-(trimethylammonio-acetyl)diethanolamine chloride, 1,3-dioleoyloxy-2-(6-carboxy-spermyl)-propylamide (DOSPER), and N,N,N',N'-tetramethyl-, N'-bis(2-hydroxylethyl)-2,3-dioleoyloxy-1,4-butanediammonium iodide, 1-[2-(acyloxy)ethyl]2-alkyl(alkenyl)-3-(2-hydroxyethyl)-imidazolinium chloride derivatives, such as 1-[2-(9 (Z)-octadecenoyloxy)ethyl]-2-(8(Z)-heptadecenyl-3-(2-hydroxyethyl)imidazolinium chloride (DOTIM) and 1-[2-(hexadecanoyloxy)ethyl]-2-pentadecyl-3-(2-hydroxyethyl) imidazolinium chloride (DPTIM), and 2,3-dialkyloxypropyl quaternary ammonium derivatives containing a hydroxyalkyl moiety on the quaternary amine, for example, 1,2-dioleoyl-3-dimethyl-hydroxyethyl ammonium bromide (DORI), 1,2-dioleyloxypropyl-3-dimethyl-hydroxyethyl ammonium bromide (DORIE), 1,2-dioleyloxypropyl-3-dimetyl-hydroxypropyl ammonium bromide (DORIE-HP), 1,2-dioleyl-oxy-propyl-3-dimethyl-hydroxybutyl ammonium bromide (DORIE-HB), 1,2-dioleyloxypropyl-3-dimethyl-hydroxypentyl ammonium bromide (DORIE-Hpe), 1,2-dimyristyloxypropyl-3-dimethyl-hydroxylethyl ammonium bromide (DMRIE), 1,2-dipalmityloxypropyl-3-dimethyl-hydroxyethyl ammonium bromide (DPRIE), and 1,2-disteryloxypropyl-3-dimethyl-hydroxyethyl ammonium bromide (DSRIE).

Other suitable lipids include PEGylated derivatives of the neutral, anionic, and cationic lipids described above. Incorporation of one or more PEGylated lipid derivatives into the lipid shell can result in a nanolipogel which displays polyethylene glycol chains on its surface. The resulting nanolipogels may possess increased stability and circulation time in vivo as compared to nanolipogels lacking PEG chains on their surfaces. Examples of suitable PEGylated lipids include distearoylphosphatidylethanlamine-polyethylene glycol (DSPE-PEG), including DSPE PEG(2000 MW) and DSPE PEG (5000 MW), dipalmitoyl-glycero-succinate polyethylene glycol (DPGS-PEG), stearyl-polyethylene glycol and cholesteryl-polyethylene glycol.

In preferred embodiments, the lipid shell is formed from a combination of more than one lipid. In certain embodiments the lipid shell is formed from a mixture of at least three lipids. In particular embodiments, the lipid shell is formed from a mixture of phosphatidyl choline (PC), 1,2-distearoyl-sn-glycero-3-phosphoethanolamine-N-[amino (polyethylene glycol)-2000] (DSPE-PEG), and cholesterol.

In some embodiments, the lipid shell is formed from a mixture of one or more PEGylated phospholipids and one or more additional lipids or sterols. In certain instances, the molar ratio of the one or more PEGylated lipids to the one or more additional lipids or sterols ranges from about 1:1 to about 1:6, more preferably from about 1:2 to about 1:6, most preferably from about 1:3 to about 1:5. In particular embodiments, the molar ratio of the one or more PEGylated lipids to the one or more additional lipids or sterols is about 1:4.

In some embodiments, the lipid shell is formed from a mixture of one or more phospholipids and one or more additional lipids or sterols. In certain instances, the molar ratio of the one or more phospholipids to the one or more additional lipids or sterols ranges from about 1:1 to about 6:1, more preferably from about 2:1 to about 6:1, most preferably from about 3:1 to about 5:1. In particular embodiments, the molar ratio of the one or more phospho lipids to the one or more additional lipids or sterols is about 4:1.

In a preferred embodiments, the lipid shell is formed from a mixture of a phospholipid, such as phosphatidyl choline (PC), a PEGylated phospholipid, such as 1,2-distearoyl-sn-glycero-3-phosphoethanolamine-N-[amino(polyethylene glycol)-2000] (DSPE-PEG), and cholesterol. In particular embodiments, the lipid shell is formed from a mixture of phosphatidyl choline, 1,2-distearoyl-sn-glycero-3-phosphoethanolamine-N-[amino(polyethylene glycol)-2000] (DSPE-PEG), and cholesterol in a 3:1:1 molar ratio.

2. Targeting Molecules and Molecules Decreasing RES Uptake

The surface of the nanolipogels, or the core host, can be modified to facilitate targeting through the attachment of targeting molecules. Exemplary target molecules include proteins, peptides, nucleic acids, lipids, saccharides, or polysaccharides that bind to one or more targets associated with an organ, tissue, cell, or extracellular matrix, or specific type of tumor or infected cell. The degree of specificity with which the nanolipogels are targeted can be modulated through the selection of a targeting molecule with the appropriate affinity and specificity. For example, a targeting moiety can be a polypeptide, such as an antibody that specifically recognizes a tumor marker that is present exclusively or in higher amounts on a malignant cell (e.g., a tumor antigen). Suitable targeting molecules that can be used to direct nanoparticles to cells and tissues of interest, as well as methods of conjugating target molecules to nanoparticles, are known in the art. See, for example, Ruoslahti, et al. *Nat. Rev. Cancer,* 2:83-90 (2002). Targeting molecules can also include neuropilins and endothelial targeting molecules, integrins, selectins, and adhesion molecules. Targeting molecules can be covalently bound to nanolipogels using a variety of methods known in the art.

In certain embodiments, the liposomal shell includes one or more PEGylated lipids. The PEG, or other hydrophilic polyalkylene oxide, avoids uptake of the lipogels by the reticuloendothelial system ("RES"), thereby prolonging in vivo residence time.

The surface of the nanolipogels can be modified to facilitate targeting through the attachment of targeting molecules. These can be proteins, peptides, nucleic acid molecules, saccharides or polysaccharides that bind to a receptor or other molecule on the surface of a targeted cell. The degree of specificity can be modulated through the selection of the targeting molecule. For example, antibodies are very specific. These can be polyclonal, monoclonal, fragments, recombinant, or single chain, many of which are commercially available or readily obtained using standard techniques. T-cell specific molecules and antigens which are bound by antigen presenting cells as well as tumor targeting molecules can be bound to the surface of the nanolipogel and/or to the host molecule. The targeting molecules may be conjugated to the terminus of one or more PEG chains present on the surface of the liposomal shell.

3. Active Agents

The shell of the nanolipogels may optionally contain one or more active agents, including any of the active agents described above.

Hydrophobic active agents, such as proteins, may be covalently connected to the surface of the nanolipogel, whereas hydrophilic active agents may be covalently connected to the surface of the nanolipogel or dispersed within the liposomal shell. In certain embodiments, the liposomal shell includes one or more PEGylated lipids. In these cases, one or more active agents may be conjugated to the terminus of one or more PEG chains present on the surface of the liposomal shell. In particular embodiments, one or more active agents are covalently connected to the surface of the nanolipogel via a linking group that is cleaved in response to an external chemical or physical stimulus, such as a change in ambient pH, so as to trigger release of the active agent at a desired physiological locale.

III. Methods of Manufacture, Loading, and Pharmaceutical Compositions

A. Methods of Manufacture and Loading

A nanolipogel is a nanoparticle that combines the advantages of both liposomes and polymer-based particles for sustained delivery of nucleic acids, proteins and/or small molecules. The nanolipogel can be in the form of spheres, discs, rods or other geometries with different aspect ratios. The nanosphere can be larger, i.e., microparticles. The nanolipogel is typically formed of synthetic or natural polymers capable of encapsulating agents by remote loading and tunable in properties so as to facilitate different rates of release. Release rates are modulated by varying the polymer to lipid ratio from 0.05 to 5.0, more preferably from 0.5 to 1.5.

Nanolipogels are designed to be loaded with agents either prior to, during or after formation and subsequently function as controlled-release vehicles for the agents. The nanolipogel can be loaded with more than one agent such that controlled release of the multiplicity of agents is subsequently achieved.

The nanolipogel is loaded with one or more first agents during formation and one or more second agents following formation by the process of rehydration of the nanolipogel in the presence of the second agents. For example, the nanolipogel is loaded with a molecule that serves as an adjuvant and the nanolipogel thereafter incorporates one or more target antigens after formation, for the controlled release of adjuvant together with the antigens. Alternatively, the nanolipogel loaded with adjuvant is inserted into the site of a tumor in a patient, the tumor is ablated, the nanolipogel is loaded with released tumor antigens and the nanolipogel releases the tumor antigens together with adjuvant into the body of the patient in a controlled manner.

In another embodiment, the nanolipogel is loaded with an antigen, a molecule that serves as an adjuvant and a targeting molecule for antigen presenting cells, the nanolipogel is taken up by antigen presenting cells and the antigen is appropriately processed and presented to T-helper and cytotoxic T-cells to promote a cell-mediated immune response.

In yet another embodiment, the nanolipogel loaded with a molecule that serves as an adjuvant and a targeting molecule for antigen presenting cells is inserted into the site of a tumor in a patient, the tumor is ablated and the nanolipogel is loaded with released tumor antigens, the nanolipogel is taken up by antigen presenting cells and the released tumor antigens are appropriately processed and presented to T-helper and cytotoxic T-cells to promote a cell-mediated immune response.

B. Pharmaceutical Compositions

Pharmaceutical compositions including nanolipogels are provided. Pharmaceutical compositions can be for administration by parenteral (intramuscular, intraperitoneal, intravenous (IV) or subcutaneous injection), transdermal (either passively or using iontophoresis or electroporation), or transmucosal (nasal, vaginal, rectal, or sublingual) routes of administration or using bioerodible inserts and can be formulated in dosage forms appropriate for each route of administration.

In some embodiments, the compositions are administered systemically, for example, by intravenous or intraperitoneal administration, in an amount effective for delivery of the compositions to targeted cells. Other possible routes include trans-dermal or oral.

In certain embodiments, the compositions are administered locally, for example by injection directly into a site to be treated. In some embodiments, the compositions are injected or otherwise administered directly to one or more tumors. Typically, local injection causes an increased localized concentration of the compositions which is greater than that which can be achieved by systemic administration. In some embodiments, the compositions are delivered locally to the appropriate cells by using a catheter or syringe. Other means of delivering such compositions locally to cells include using infusion pumps (for example, from Alza Corporation, Palo Alto, Calif.) or incorporating the compositions into polymeric implants (see, for example, P. Johnson and J. G. Lloyd-Jones, eds., Drug Delivery Systems (Chichester, England: Ellis Horwood Ltd., 1987), which can effect a sustained release of the nanolipogels to the immediate area of the implant.

The nanolipogels can be provided to the cell either directly, such as by contacting it with the cell, or indirectly, such as through the action of any biological process. For example, the nanolipogels can be formulated in a physiologically acceptable carrier or vehicle, and injected into a tissue or fluid surrounding the cell. The nanolipogels can cross the cell membrane by simple diffusion, endocytosis, or by any active or passive transport mechanism.

As further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. Generally dosage levels of 0.001 to 10 mg/kg of body weight daily are administered to mammals. Generally, for intravenous injection or infusion, dosage may be lower. Generally, the total amount of the nanolipogel-associated active agent administered to an individual will be less than the amount of the unassociated active agent that must be administered for the same desired or intended effect.

1. Formulations for Parenteral Administration

In a preferred embodiment the nanolipogels are administered in an aqueous solution, by parenteral injection. The formulation can be in the form of a suspension or emulsion. In general, pharmaceutical compositions are provided including effective amounts of one or more active agents optionally include pharmaceutically acceptable diluents, preservatives, solubilizers, emulsifiers, adjuvants and/or carriers. Such compositions can include diluents sterile water, buffered saline of various buffer content (e.g., Tris-HC, acetate, phosphate), pH and ionic strength; and optionally, additives such as detergents and solubilizing agents (e.g., TWEEN® 20, TWEEN® 80 also referred to as polysorbate 20 or 80), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

2. Formulations for Topical and Mucosal Administration

The nanolipogels can be applied topically. Topical administration can include application to the lungs, nasal, oral (sublingual, buccal), vaginal, or rectal mucosa. These methods of administration can be made effective by formulating the shell with transdermal or mucosal transport elements. For transdermal delivery such elements may include chemical enhancers or physical enhancers such as electroporation or microneedle delivery. For mucosal delivery PEGylation of the outer shell or addition of chitosan or other mucosal permeants or PH protective elements for oral delivery.

Compositions can be delivered to the lungs while inhaling and traverse across the lung epithelial lining to the blood stream when delivered either as an aerosol or spray dried particles having an aerodynamic diameter of less than about 5 microns.

A wide range of mechanical devices designed for pulmonary delivery of therapeutic products can be used, including but not limited to nebulizers, metered dose inhalers, and powder inhalers, all of which are familiar to those skilled in the art. Some specific examples of commercially available devices are the Ultravent® nebulizer (Mallinckrodt Inc., St. Louis, Mo.); the Acorn® II nebulizer (Marquest Medical Products, Englewood, Colo.); the Ventolin® metered dose inhaler (Glaxo Inc., Research Triangle Park, N.C.); and the Spinhaler® powder inhaler (Fisons Corp., Bedford, Mass.). Nektar, Alkermes and Mannkind all have inhalable insulin powder preparations approved or in clinical trials where the technology could be applied to the formulations described herein.

Formulations for administration to the mucosa will typically be spray dried drug particles, which may be incorporated into a tablet, gel, capsule, suspension or emulsion. Standard pharmaceutical excipients are available from any formulator. Oral formulations may be in the form of chewing gum, gel strips, tablets, capsules, or lozenges. Oral formulations may include excipients or other modifications to the particle which can confer enteric protection or enhanced delivery through the GI tract, including the intestinal epithelia and mucosa (see Samstein, et al. *Biomaterials.* 29(6): 703-8 (2008).

Transdermal formulations may also be prepared. These will typically be ointments, lotions, sprays, or patches, all of which can be prepared using standard technology. Transdermal formulations can include penetration enhancers. Chemical enhancers and physical methods including electroporation and microneedles can work in conjunction with this method.

IV. Methods of Treatment

The methods of treatment typically include using nanolipogels loaded with one or more active agents, to deliver the one or more active agents into cells, or to a cell's microenvironment. The methods typically include contacting the active agent-loaded nanolipogel with one more cells. The contacting can occur in vivo or in vitro.

Administration of a drug or other cargo to cells or a subject using nanolipogels can be compared to a control, for example, delivery of the drug or other cargo to cells or a subject using conventional delivery methods such as free cargo/drug delivery, delivery using conventional PLGA nanoparticles, or delivery using conventional liposomal methods such as LIPOFECTAMINE®. Nanolipogels can be used to deliver cargo to target cells with increased efficacy compared to conventional delivery methods. In some embodiments less cargo or drug is required when delivered using nanolipogels compared to conventional delivery methods to achieve the same or greater therapeutic benefit.

In some embodiments toxicity is reduced or absent compared to conventional delivery methods. For example, in some embodiments, white blood cell, platelet, hemoglobin, and hematocrit levels were within normal physiological ranges; no liver or renal toxicities are observed; body weight and serum concentrations for alkaline phosphatase, alanine transferase, total bilirubin, and blood urea nitrogen are normal; or combinations thereof following administration of loaded nanolipogels to the subject.

A. In Vivo Methods

The disclosed compositions can be used in a method of delivering active agents to cells in vivo. In some in vivo approaches, the compositions are administered to a subject in a therapeutically effective amount. As used herein, the term "effective amount" or "therapeutically effective amount" means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, etc.), the disease, and the treatment being effected.

1. Drug Delivery

The particles can be used to deliver an effective amount of one or more therapeutic, diagnostic, and/or prophylactic agents to an individual in need of such treatment. The amount of agent to be administered can be readily determine by the prescribing physician and is dependent on the age and weight of the patient and the disease or disorder to be treated.

The particles are useful in drug delivery (as used herein "drug" includes therapeutic, nutritional, diagnostic and prophylactic agents), whether injected intravenously, subcutaneously, or intramuscularly, administered to the nasal or pulmonary system, injected into a tumor milieu, administered to a mucosal surface (vaginal, rectal, buccal, sublingual), or encapsulated for oral delivery. The particles may be administered as a dry powder, as an aqueous suspension (in water, saline, buffered saline, etc), in a hydrogel, organogel, in capsules, tablets, troches, or other standard pharmaceutical excipient The preferred embodiment is a dry powder rehydrated with the capsulant of interest in sterile saline or other pharmaceutically acceptable excipient.

As discussed herein, compositions can be used to as delivery vehicles for a number of active agents including small molecules, nucleic acids, proteins, and other bioactive agents. The active agent or agents can be encapsulated within, dispersed within, and/or associated with the surface of the nanolipogel particle. In some embodiments, the nanolipogel packages two, three, four, or more different active agents for simultaneous delivery to a cell.

2. Transfection

The disclosed compositions can be for cell transfection of polynucleotides. As discussed in more detail below, the transfection can occur in vitro or in vivo, and can be applied in applications including gene therapy and disease treatment. The compositions can be more efficient, less toxic, or a combination thereof when compared to a control. In some embodiments, the control is cells treated with an alternative transfection reagent such as LIPOFECTAMINE 2000.

The particular polynucleotide delivered by the nanolipogel can be selected by one of skill in the art depending on the condition or disease to be treated. The polynucleotide can be, for example, a gene or cDNA of interest, a functional nucleic acid such as an inhibitory RNA, a tRNA, an rRNA, or an expression vector encoding a gene or cDNA of interest, a functional nucleic acid a tRNA, or an rRNA. In some embodiments two or more polynucleotides are administered in combination.

In some embodiments, the polynucleotide encodes a protein. Exemplary proteins include, for example, (a) angiogenic and other factors including growth factors such as acidic and basic fibroblast growth factors, vascular endothelial growth factor, endothelial mitogenic growth factors, epidermal growth factor, transforming growth factor α and β, platelet-derived endothelial growth factor, platelet-derived growth factor, tumor necrosis factor-α, hepatocyte growth factor and insulin-like growth factor; (b) cell cycle inhibitors such as cyclin-dependent kinases, thymidine kinase ("TK"), and other agents useful for interfering with cell proliferation; (c) bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. BMPs are typically dimeric proteins that can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

In some embodiments, the polynucleotide is not integrated into the host cell's genome (i.e., remains extrachromosomal). Such embodiments can be useful for transient or regulated expression of the polynucleotide, and reduce the risk of insertional mutagenesis. Therefore, in some embodiments, the nanolipogels are used to deliver mRNA or non-integrating expression vectors that are expressed transiently in the host cell.

In some embodiments, the polynucleotide is integrated into the host cell's genome. For example, gene therapy is a technique for correcting defective genes responsible for disease development. Researchers may use one of several approaches for correcting faulty genes: (a) a normal gene can be inserted into a nonspecific location within the genome to replace a nonfunctional gene. This approach is most common; (b) an abnormal gene can be swapped for a normal gene through homologous recombination; (c) an abnormal gene can be repaired through selective reverse mutation, which returns the gene to its normal function; (d) the regulation (the degree to which a gene is turned on or off) of a particular gene can be altered.

Gene therapy can include the use of viral vectors, for example, adenovirus, adeno-associated virus, herpes virus, vaccinia virus, polio virus, AIDS virus, neuronal trophic virus, Sindbis and other RNA viruses, including these viruses with the HIV backbone. Also useful are any viral families which share the properties of these viruses which make them suitable for use as vectors. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promoter cassette is inserted into the viral genome in place of the removed viral DNA.

Gene targeting via target recombination, such as homologous recombination (HR), is another strategy for gene correction. Gene correction at a target locus can be mediated by donor DNA fragments homologous to the target gene (Hu, et al., Mol. Biotech., 29:197-210 (2005); Olsen, et al., J. Gene Med., 7:1534-1544 (2005)). One method of targeted recombination includes the use of triplex-forming oligonucleotides (TFOs) which bind as third strands to homopurine/homopyrimidine sites in duplex DNA in a sequence-specific manner. Triplex forming oligonucleotides can interact with either double-stranded or single-stranded nucleic acids.

Methods for targeted gene therapy using triplex-forming oligonucleotides (TFO's) and peptide nucleic acids (PNAs) are described in U.S. Published Application No. 20070219122 and their use for treating infectious diseases such as HIV are described in U.S. Published Application No. 2008050920. The triplex-forming molecules can also be tail clamp peptide nucleic acids (tcPNAs), such as those described in U.S. Published Application No. 2011/0262406. Highly stable PNA:DNA:PNA triplex structures can be formed from strand invasion of a duplex DNA with two PNA strands. In this complex, the PNA/DNA/PNA triple helix portion and the PNA/DNA duplex portion both produce displacement of the pyrimidine-rich triple helix, creating an altered structure that has been shown to strongly provoke the nucleotide excision repair pathway and to activate the site for recombination with the donor oligonucleotide. Two PNA strands can also be linked together to form a bis-PNA molecule.

The triplex-forming molecules are useful to induce site-specific homologous recombination in mammalian cells when used in combination with one or more donor oligonucleotides which provides the corrected sequence. Donor oligonucleotides can be tethered to triplex-forming molecules or can be separate from the triplex-forming molecules. The donor oligonucleotides can contain at least one nucleotide mutation, insertion or deletion relative to the target duplex DNA.

Double duplex-forming molecules, such as a pair of pseudocomplementary oligonucleotides, can also induce recombination with a donor oligonucleotide at a chromosomal site. Use of pseudocomplementary oligonucleotides in targeted gene therapy is described in U.S. Published Application No. 2011/0262406. Pseudocomplementary oligonucleotides are complementary oligonucleotides that contain one or more modifications such that they do not recognize or hybridize to each other, for example due to steric hindrance, but each can recognize and hybridize to complementary nucleic acid strands at the target site. In some embodiments, pseudocomplementary oligonucleotides are pseudocomplemenary peptide nucleic acids (pcPNAs). Pseudocomplementary oligonucleotides can be more efficient and provide increased target site flexibility over methods of induced recombination such as triple-helix oligonucleotides and bis-peptide nucleic acids which require a polypurine sequence in the target double-stranded DNA.

B. In Vitro Methods

The disclosed compositions can be used in a method of delivering active agents to cells in vitro. For example, the nanolipogels can be used for in vitro transfection of cells. The method typically involves contacting the cells with nanolipogels including a polynucleotide in an effective amount to introduce the polynucleotide into the cell's cytoplasm. In some embodiments, the polynucleotide is delivered to the cells in an effective amount to change the genotype or a phenotype of the cell. The cells can be primary cells isolated from a subject, or cells of an established cell line. The cells can be of a homogenous cell type, or can be a heterogeneous mixture of different cells types. For example, the polyplexes can be introduced into the cytoplasm of cells from a heterogenous cell line possessing cells of different types, such as in a feeder cell culture, or a mixed culture in various states of differentiation. The cells can be a transformed cell line that can be maintained indefinitely in cell culture. Exemplary cell lines are those available from American Type Culture Collection including tumor cell lines.

Any eukaryotic cell can be transfected to produce cells that express a specific nucleic acid, for example, a metabolic gene, including primary cells as well as established cell lines. Suitable types of cells include, but are not limited to, undifferentiated or partially differentiated cells including stem cells, totipotent cells, pluripotent cells, embryonic stem cells, inner mass cells, adult stem cells, bone marrow cells, cells from umbilical cord blood, and cells derived from ectoderm, mesoderm, or endoderm. Suitable differentiated cells include somatic cells, neuronal cells, skeletal muscle, smooth muscle, pancreatic cells, liver cells, and cardiac cells. In another embodiment, siRNA, antisense polynucleotides (including siRNA or antisense polynucleotides) or inhibitory RNA can be transfected into a cell using the compositions described herein.

The methods are particularly useful in the field of personalized therapy, for example, to repair a defective gene, de-differentiate cells, or reprogram-cells. For example, target cells are first isolated from a donor using methods known in the art, contacted with the nanolipogel including a polynucleotide causing a change to the in vitro (ex vivo), and administered to a patient in need thereof. Sources or cells include cells harvested directly from the patient or an allographic donor. In preferred embodiments, the target cells to be administered to a subject will be autologous, e.g. derived from the subject, or syngenic. Allogeneic cells can also be isolated from antigenically matched, genetically unrelated donors (identified through a national registry), or by using target cells obtained or derived from a genetically related sibling or parent.

Cells can be selected by positive and/or negative selection techniques. For example, antibodies binding a particular cell surface protein may be conjugated to magnetic beads and immunogenic procedures utilized to recover the desired cell type. It may be desirable to enrich the target cells prior to transient transfection. As used herein in the context of compositions enriched for a particular target cell, "enriched" indicates a proportion of a desirable element (e.g. the target cell) which is higher than that found in the natural source of the cells. A composition of cells may be enriched over a natural source of the cells by at least one order of magnitude, preferably two or three orders, and more preferably 10, 100, 200, or 1000 orders of magnitude. Once target cells have been isolated, they may be propagated by growing in suitable medium according to established methods known in the art. Established cell lines may also be useful in for the methods. The cells can be stored frozen before transfection, if necessary.

Next the cells are contacted with the disclosed composition in vitro to repair, de-differentiate, re-differentiate, and/or re-program the cell. The cells can be monitored, and the desired cell type can be selected for therapeutic administration. For examples, in some embodiments the disclosed methods are be used to create allogeneic pluripotent or multipotent cells (i.e., stem cells) from differentiated cells, or to change the phenotype of immune cells.

Following repair, de-differentiation, and/or re-differentiation and/or reprogramming, the cells are administered to a patient in need thereof. In the most preferred embodiments, the cells are isolated from and administered back to the same patient. In alternative embodiments, the cells are isolated from one patient, and administered to a second patient. The method can also be used to produce frozen stocks of altered cells which can be stored long-term, for later use. In one embodiment, fibroblasts, keratinocytes or hematopoietic stem cells are isolated from a patient and repaired, de-differentiated, or reprogrammed in vitro to provide therapeutic cells for the patient.

C. Diseases to Be Treated

The compositions including nanolipogel delivery vehicles can be used to treat a variety of diseases and conditions, for example, cancer and infectious diseases. The compositions can be administered to the subject therapeutically or prophylactically. Exemplary therapeutic and prophylactic strategies are discussed in more detail below and in the Examples.

For example, in some embodiments, a cell penetrating peptide, also known as cell permeable peptides, protein transduction domains (PTDs), membrane translocating sequences (MTSs) and Trojan peptides, (for example a stimulus-responsive cell penetrating peptide) is a conjugated to a dendrimer in a nanolipogel formulation. Cell penetrating peptides include, but are not limited to, virus-derived or mimicking polymers such as TAT, influenza fusion peptide, rabies virus glycoprotein fragment (RVG), neuropilin, penetratin, and polyarginines. Anaspec has commercially available CPPs:

The nanolipogel can be used to deliver active agents to cells including, but not limited to difficult to penetrate cells, HIV infected cells, T cell lymphomas, and B cells.

In some embodiments, the nanolipogel includes a death receptor agonist (such as Fas/CD95 ligand and TRAIL/Apo2L) and death receptors (such as Fas/CD95, TRAIL-R1/DR4, and TRAIL-R2/DR5) which is involved in immune-mediated neutralization of activated or autoreactive lymphocytes, virus-infected cells, and tumor cells. Dysregulation of death receptor-dependent apoptotic signaling pathways has been implicated in the development of autoimmune diseases, immunodeficiency, and cancer. Moreover, the death ligand TRAIL has gained considerable interest as a potential anticancer agent, given its ability to induce apoptosis of tumor cells without affecting most types of untransformed cells. The FLICE-inhibitory protein (FLIP) potently blocks TRAIL-mediated cell death by interfering with caspase-8 activation. Pharmacologic down-regulation of FLIP might serve as a therapeutic means to sensitize tumor cells to apoptosis induction by TRAIL. Accordingly, death ligands or receptors can be incorporated onto or into the nanolipogel as the targeting moiety and/or as the active agent to enhance cell specific delivery and to sensitivity target cells, such as a cancer cells or virally transformed cells, to apoptosis.

In some embodiments, the nanolipogel includes a moiety that specifically targets a sirtuin. Sirtuin or Six2 proteins are a class of proteins that possess either histone deacetylase or mono-ribosyltransferase activity. Sirtuins regulate important biological pathways in bacteria, archaea and eukaryotes, and have been implicated in influencing aging and regulating transcription, apoptosis and stress resistance, as well as energy efficiency and alertness during low-calorie situations. Accordingly, Sirtuin or Sir2 proteins can be targeted as part of an anti-aging prophylactic or therapeutic strategy.

In some embodiments, the active agent(s) includes a Histone deacetylase inhibitor (HDACi). HDACi are chemical compounds that interfere with the function of HDAC enzymes. They inhibit HDAC enzyme activity, and therefore, tip the equilibrium in favor of acetylated histones. HDACi can also affect the activity of many non-histone proteins, as they can also be targeted by lysine acetylation/deacetylation, leading to an increased episode of acetylation of many gene clusters, leading to an increase of transcription activity and, subsequently, upregulation of specific genes. In some embodiments, the active agent includes a chemotherapeutic agent. Co-delivery of an HDACi and a chemotherapeutic drug may be particularly effective for treating cancers, including multi-drug resistant cancers such as pancreatic cancer and melanoma.

In some embodiments, the nanolipogel is part of a vaccine strategy. For example, the nanolipogel can be used to deliver an antigen, an immunostimulant, an adjuvant, or a combination thereof. In some embodiments, the nanolipogel includes a target moiety that directs the delivery vehicle to specific immune cells, for example, antigen presenting cells such as dendritic cells. In some embodiments, the nanolipogel includes one or more antigen presenting cell targeting moieties displayed on the outer shell, and TLR ligands inside or outside the nanolipogel, alone or in combination with an antigen. The antigen can be any known antigen, for example, an antigen derived from a bacteria, a virus, a fungi, a parasite, or another microbe, or tumor antigens or environmental antigens.

In some embodiments the nanolipogel includes pH responsive elements so that the contents of the nanolipogel are released upon encountering a low pH. This strategy can be employed to increase delivery of the nanolipogel contents to tumor cells or microenvironments or cardiac cells under hypoxic conditions. In some embodiments, the nanolipogels are used in photodynamic therapy. For example, pH-sensitive nanolipogel can release a photodynamic therapy agent such as hypercirin, the area of treatment, for example tumor cells, or a tumor microenvironment.

In some embodiments, the active agent(s) includes a Transcription Activator-Like Effector Nucleases (TALENs). TALENs are artificial restriction enzymes generated by fusing the TAL effector DNA binding domain to a DNA cleavage domain. TALENs can be employed for efficient, programmable, and specific DNA cleavage and represent powerful tools for genome editing in situ. Synthetic transcription factors using TALE domain constructs can also be used for gene regulation by pairing the TALE DNA binding domain with an endogenous activation domain affecting expression at specific sites in complex genomes. Transcription activator-like effectors (TALEs) can be quickly engineered to bind practically any DNA sequence. Accordingly, TALENs can be used in gene therapy methods, for example to edit HIV-associated genes such as CCR5, or to treat monogenetic mutations in genetic diseases such as cystic fibrosis.

In some embodiments, the nanolipogel includes a pathogen-associated molecular pattern molecule (PAMP) targeting moiety. PAMPs are small molecular motifs associated with groups of pathogens, that are recognized by cells of the innate immune system. They are recognized by Toll-like receptors (TLRs) and other pattern recognition receptors (PRRs) in both plants and animals. They activate innate immune responses, protecting the host from infection, by identifying some conserved non-self molecules. For example, bacterial Lipopolysaccharide (LPS), an endotoxin found on the bacterial cell membrane of a bacterium, is considered to be the prototypical PAMP. LPS is specifically recognized by TLR 4, a recognition receptor of the innate immune system. Other PAMPs include, but are not limited to, bacterial flagellin (recognized by TLR 5), lipoteichoic acid from Gram positive bacteria, peptidoglycan, and nucleic acid variants normally associated with viruses, such as double-stranded RNA (dsRNA), recognized by TLR 3 or unmethylated CpG motifs, recognized by TLR 9. Accordingly, one or more PAMPs can be used to increase an immune response against an infectious disease.

In some embodiments, the nanolipogel includes a damage-associated molecular pattern molecule (DAMP). DAMPs include intracellular molecules released by activated or necrotic cells and extracellular matrix molecules that are upregulated upon injury or degraded following tissue damage. DAMPs are danger signals that alert the immune signal to tissue damage upon infection and tissue damage, but have also been implicated in excessive inflammation including rheumatoid arthritis, cancer, and atherosclerosis (Piccinini and Midwood, *Mediators of Inflammation*, Vol. 2010, Article ID 672395, 21 pages). For example, in some embodiments, DAMPs can be used as part of a nanolipogel strategy to induce an immune response wherein the DAMPs mimic a necrotic cell. Exemplary DAMPs include, but are not limited to, F-actin, HMGB1 (high mobility group box protein-1), S100A8/S100A9, heat-shock proteins, uric acid and DNA. In some embodiments, DAMPs are incorporated into a vaccine strategy, for example, a cancer vaccine strategy. For example, DAMP can be delivered to immune cells using a nanolipogel decorated with an antigen presenting cell targeting ligand. In some embodiments, the cancer vaccine strategy also include delivery of one or more tumor associated antigens.

D. Exemplary Disease Treatment Strategies

1. Methods of Immunotherapy and Cancer Treatment

One mechanism behind how melanomas and other cancers evade the antitumor response is postulated to be the inability of the innate immune system to recognize the tumor as 'non-self'. This may occur due to the secretion of a number of immunosuppressive factors by tumor cells, including transforming growth factor-β (TGF-β3), a pleiotropic cytokine that decreases natural killer cell (NK) number and function and cytotoxic T lymphocyte (CTL) function while increasing the number of regulatory T lymphocytes (Tregs). TGF-β activity has been extensively evaluated in a number of animal disease systems, including murine tumor models, and its secretion is suspected to thwart high-dose interleukin-2 (IL-2) therapy, which is supposed to enhance NK and CTL activity against melanomas and renal cell cancers but lacks efficacy in the majority of patients. This has led groups to evaluate strategies to counteract immunosuppressive factors secreted from tumors, including TGF-β. Although the exact source of intratumoral TGF-β has not been well-established, the cytokine has been found at high levels in a large number of different tumors, including melanomas. It is believed that TGF-β is pivotal for tumor cell growth and differentiation as well as maintaining an immunosuppressive environment to protect an established tumor from the host immune response, rendering it an ideal target for cancer therapies. In particular, its suppressive effect on the number of NK cells present in tumor beds may be crucial for immune tolerance, as these cells play an important role in the anti-tumor response.

Examples demonstrate the efficacy of simultaneous, sustained release of IL-2 and SB against tumors. Given the vastly different physiochemical properties of IL-2, a soluble 17 kDa protein, and SB, a small hydrophobic drug (Log P=4.33), co-encapsulation for sustained release of both agents presented a challenge for conventional particle technologies. For example, liposomes are easily modified for encapsulation of small hydrophilic molecules, and even proteins, but the stability of these formulations and the release profiles of encapsulated agents are not easily controlled. Biodegradable solid particles, on the other hand, such as those fabricated from poly(lactic-co-glycolic acid) (PLGA), are highly stable and have controllable release characteristics, but pose complications for facile encapsulation and controlled release of therapeutic cytokines or for combinatorial delivery.

Metastatic melanoma is highly aggressive, leaving untreated patients with a median survival of less than 12 months. The ineffectiveness of surgical interventions, radiation and cytotoxic chemotherapies has resulted in immunotherapy as the primary treatment modality. Approximately 5% of patients with metastatic melanoma achieve durable complete remissions when treated with high dose IL-2, presumably via induction or expansion of activation of melanoma-specific T cell responses. However, because high dose-related toxicity of IL-2 hampers its therapeutic benefits, newer generation formulations aim to reduce the administered dose by increasing the half-life of the cytokine in circulation. Some examples include fusion proteins (IL-2/Ig), pegylated IL-2, IL-2/anti-IL-2 complexes, liposomal formulations and viral and plasmid vectors. Nanolipogel combination delivery of TGF-β inhibitor and IL-2 enhances tumor immunotherapy. The sustained release of two diverse chemical agents from nanolipogels elicits an impressive anti-tumor effect. The tumor microenvironment thwarts conventional immunotherapy through multiple immunologic mechanisms. Several of these mechanisms are believed to include secretion of the transforming growth factor-β (TGF-β), which stunts local tumor immune responses. Thus, even a high dose of interleukin-2 (IL-2), a conventional cytokine FDA-approved treatment for metastatic melanoma, only induces limited responses.

To overcome the immunoinhibitory nature of the tumor microenvironment, a vehicle is needed for releasing to the tumor microenvironment in a controlled fashion an inhibitor of TGF-β together with IL-2. One well-known inhibitor of TGF-β is 2-(5-benzo[1,3]dioxol-5-yl-2-tert-butyl-3H-imidazol-4-yl)-6-methylpyridine hydrochloride (known as SB-505124 and referred to herein as SB). However, given the vastly different physiochemical properties of IL-2, a soluble 17 kDa protein, and SB, a small hydrophobic drug (Log P=4.33), co-encapsulation for sustained release of both agents presented a challenge for conventional particle technologies. The nanolipogel platform combines features of both liposomes and polymer-based particles for encapsulation and sustained delivery of therapeutic proteins and small molecule hydrophobic drugs.

The sustained delivery of both IL-2 and SB from this system induces potent antitumor immune responses in a B16/B6 mouse model of melanoma after intratumoral or systemic administration. Nanolipogels releasing TGF-β inhibitor and IL-2 significantly delayed tumor growth, increased survival of tumor-bearing mice and increased intratumoral natural killer cells (NK). Additionally, induction of remission with this combination therapy was mediated through activation of both the innate and adaptive arms of the immune response, with the innate arm playing a critical role in mediating antitumor activity in vivo. The formulation offers an advantage by not only increasing the cytokine half-life in circulation but also by co-delivering in a sustained manner SB, a potent pleiotropic inhibitor that suppresses the tumor's ability to thwart an immune response.

Combination therapies that stimulate immune responses while overcoming the tumor inhibitory environment are attractive modalities for cancer immunotherapy. The nanolipogel platform which has been demonstrated to be effective in combination therapy in the Examples below in turn provide a platform for therapy in a variety of diseases in which it is desirable to simultaneously utilize combinations of drugs in a treatment regimen. Such combination therapies, and the diseases in which they are useful, are well known in the art.

Exemplary cancer therapies are outlined in Table 1 below. The table presents a pathological aberrance that is addressed by the therapy; the cells target(s) of the therapy; one, two, or three therapeutic molecules that can be delivered by the nanolipogels alone or in any combination thereof; a desired target or targeting moiety can be used to target the nanoliposomes; the preferred delivery mechanism; and intended effects of the therapy.

TABLE 1

Exemplary Cancer Therapies and Strategies

| Disease | Pathological Abberrance | Cell Target(s) | Delivered Molecule (DM) 1: | Delivered Molecule 2: |
|---|---|---|---|---|
| Multi-Drug Resistant (MDR) cancer | chemo drugs kill rapidly dividing cells cancer senescence evades drugs | cancer cells | histone deacetylase inhibitor (HDACi) | chemo drug |
| MDR Cancer | induced Tregs (iTregs) enhance cancer immunoediting | iTregs | siRNA against FoxP3 | HDACi to modify epigenetics |
| MDR Cancer | IL-10 Tregs have same suppressive fxn as FoxP3 iTregs in mouse | IL-10 Tregs | unclear. IL-2 plays a role . . . | |
| Cancer | cancer cells create in visibility to immune cells | tumor cells | pHLIP-calreticulin | |
| Cancer | tumor-associated macrophages (TAMs) promoting disease | TAMs | | |
| Unresectable Pancreatic Cancer | BC-819 plasmid | | | |
| Unresectable, MDR Pancreatic Cancer | drug delivery challenges, resististance to chemo | Pancreatic Cancer Cells | HDAC inhibitor (SAHA, TSA, etc) | chemo drug |

| Disease | DM3: | Targeting Strategy | Delivery Mechanism | Effect |
|---|---|---|---|---|
| Multi-Drug Resistant (MDR) cancer | | cancer-dependent EPR, folate, TAA, etc | preferrably HDACi is delivered first | HDACi initiates transcription, resensitizes cells to chemo |
| MDR Cancer | | iTreg surface markers not nTreg | | |
| MDR Cancer | | | | |
| Cancer | ATP, HMGB1 | pH-sensitive | other DAMPs could be employed | tumor cells mimic immunogenic cell death, create inflammatory response |
| Cancer | | | | |
| Unresectable Pancreatic Cancer | | | | |
| Unresectable, MDR Pancreatic Cancer | | antibody for tumor associated antigen (TAA) | | HDACi initiates transcription, resensitizes cells to chemo |

2. Infectious Diseases

Non-limiting examples of additional diseases that can be treated using the compositions and methods disclosed herein include infectious diseases, viral or microbial, in which a combination antiviral or antibiotic regimen, respectively, is the desirable strategy. For example, an anti-HIV formulation could include activators to initiate HIV replication, inhibitors that prevent HIV infection of new cells and a mixture of death-inducers that are exclusively activated within the infected cell with no harm befalling the others. The outer lipid shell can be fabricated with an antibody that attaches specifically to a molecule expressed on all human T-cells. This serves as the targeting vehicle that protects the encased components and fuses with target T-cells. The nanolipogel core is fabricated from a safe, FDA approved polymer encapsulating a 'dendrimer'.

This inner dendrimer core is complexed with 1) A HDAC inhibitor (HDACi) that activates HIV. This agent inhibits enzymes known as histone deacetylases (HDACs) that constantly remove acetyl groups on histones, enabling continued binding of histones to chromosomal DNA, which helps keep HIV latent; 2) A plasmid that encodes RNA-inhibitors called short interfering RNA (siRNA) that bind exclusively to the viral RNA and destroy it by a cellular pathway called RNA interference. siRNAs can be designed to target only the intended mRNA target with minimal side effects providing an immense advantage. These siRNAs can be expressed in all T-cells so as to prevent viral spread from the infected cell as well as productive infection in uninfected cells; and 3) Another plasmid that encodes siRNAs controlled by a promoter that is activated exclusively by the HIV proteins tat and rev and hence expressed only in infected cells. These siRNAs are designed to bind and destroy RNAs of proteins that promote cell survival. Upon attachment the entire system is internalized by the cellular machinery without altering cell physiology or homeostasis, the outermost particle breaks down to release the inner drug/gene-complexed core, which is further degraded releasing the components. Thus the system is doubly regulated for attachment only to T-cells, the reservoirs for latent HIV and selective destruction of infected T-cell reservoirs.

Exemplary therapies and strategies of treating HIV and other infectious diseases are outlined in Table 2 below. The table presents a pathological aberrance that is addressed by the therapy; the cells target(s) of the therapy; one, two, or three therapeutic molecules that can be delivered by the nanolipogels alone or in any combination thereof; a desired target or targeting moiety can be used to target the nanoliposomes; the preferred delivery mechanism; and intended effects of the therapy.

TABLE 2

Exemplary HIV Therapies and Strategies

| Disease | Pathological Abberrance | Cell Target(s) | Delivered Molecule (DM) 1: | Delivered Molecule 2: |
|---|---|---|---|---|
| HIV | latently infected T cells evade HAART | latent infected CD4+ | HDAC inhibitor (SAHA, T5A, etc) | siRNA against specific HIV proteins necessary for propogation |
| HIV | Tregs attenuate HIV immune-activation, suppress immune response to HIV + other pathogens | FoxP3+ Tregs, perhaps Ag-specific | siRNA targeting FoxP3 | |
| HIV | HAART drugs go everywhere | infected CD4+ T ceils | HAART drug 1 | HAART drug 2 |
| HIV | CCR5 allows HIV entry | CD4+ T cells | Zinc Finger Nuclease (ZFN) or TALEN against CCR5 | |
| HIV | MHC-restricted HIV epitopes do not mount sufficient immune response | APCs (DCs, macrophages) | ZFN or TALEN to change MHC sequence | |
| HIV | MHC-restricted HIV epitopes do not mount sufficient immune response | cells that will interface with T cells - even epithelial cells | optimal MHC-HIV epitope molecules | |
| Epstein-Barr Virus | B cells infected with EBV, virus replicates | EBV-infected B cells | siRNA against EBV targets | |
| Malaria | parasite infects RBCs | infected RBCs | plasmid DNA | more plasmid DNA |
| Leishmania | parasite lives in macrophages | infected macrophages | myriad small molecule drugs | excess dendrimer to help break endosome |

| Disease | DM3: | Targeting Strategy | Delivery Mechanism | Effect |
|---|---|---|---|---|
| HIV | | anti-CD7-palmitate | preferrably, HDACi is released first | expressed proteins are toxic, latent cells die |
| HIV | | anti-CD4 | | deactivate permissive Tregs |
| HIV | HAART drug 3 | anti-CD4 | | bundle HAART drugs to increase efficiency, decrease side effects |
| HIV | | anti-CD4 | prophylactic strategy | protect against HIV cellular entry |
| HIV | | passive or TLR ligand, anti-DEC205 | | modulate TCR/MHC-HIV epitope interactions to initiate robust immune response |
| HIV | | | pH-responsive insertion of MHC/epitopes for TCR presentation | make lots of APC: presenting HIV epitopes in ways the propogate immuno response |
| Epstein-Barr Virus | | anti-8220, others | Ayman's siRNA sequence | prevent virus from replicating - purge disease |
| Malaria | | | Choukri Mamoun plasmids | transform parasite, identify drug resistant infected RBCs |

TABLE 2-continued

| Exemplary HIV Therapies and Strategies | | |
|---|---|---|
| Leishmania | mannose, Fc fragment, etc | expel parasite from endolysosome, kill it |

3. Other Indications

Yet another non-limiting example is cardiovascular disease in which combination therapies well known in the art are in use to simultaneously lower both blood pressure and cholesterol levels. It is notable in a number of such diseases that modulating biodistribution would also offer advantages in the treatment strategy and as some of the Examples in this invention demonstrate, the use of nanolipogels offers promise with regard to control of biodistribution.

The success of combination therapies is a safe and flexible delivery platform that releases a variety of effector molecules with different physiochemical properties to tumor beds in a sustained fashion, such as the nanolipogel delivery system developed in this work. Recent work has demonstrated that the combination of another TGF-β receptor-I inhibitor (LY364947) and the cytotoxic chemotherapeutic agent, doxorubicin, was effective in a particulate formulation against pancreatic and gastric carcinomas. Cytokines, including IL-2, represent a complex network of soluble proteins critical for immunological and effector cell function. In a similar fashion, small molecule hydrophobic drugs, such as TGF-3 antagonists, represent a class of immunomodulators that can overcome barriers posed by tumors to escape the immune response. The sustained delivery of these agents in combination to tumor beds can induce therapeutic immune responses, while reducing the immune-resistant nature of the tumor microenvironment.

The B16 melanoma model was used to validate that the difficulties in ensuring simultaneous, synergistic delivery of both labile proteins and small hydrophobic molecules can be addressed by rational engineering of a nanoscale delivery system fabricated from inert, biodegradable components with a history of use, individually, in different drug delivery applications. The Examples illustrate that the activation of the innate arm of the immune system is a critical immunologic mechanism underlying the synergistic effects of simultaneously delivering IL-2 and SB, resulting in delayed tumor growth and enhanced survival of tumor-bearing mice. Administration of SB in combination with IL-2 stimulated the innate immune system, greatly increasing the number of NY in tumors in mice receiving this combination. Absence of therapeutic efficacy following NK depletion demonstrated that stimulation of the innate arm by nanoparticles releasing both agents was crucial for achieving an improvement in survival in this model. Particles releasing SB, IL-2 alone or the combination also stimulated the adaptive immune system, enhancing activated $CD8^+$: Treg ratios. These results show that the combination therapy can stimulate both arms of the immune system simultaneously.

Nanocarriers designed to release both soluble cytokines and hydrophobic drug molecules in a sustained fashion, even without tumor targeting, can be used to simultaneously deliver a combination of key immunomodulators to decrease the local immunosuppressive environment and enhance anti-tumor responses. The combination of IL-2 and a TGF-β antagonist at the tumor site led to significant tumor delay, and, in select cases, macroscopic remissions in the B16/B6 murine melanoma model. It is notable that aggressive tumors such as melanoma inherently develop leaky vasculature with 100 to 800 nm pores due to rapid vessel formation to sustain a rapidly growing tumor. This defect in vasculature and poor lymphatic drainage results in enhanced permeation and retention of nanoparticles within the tumor bed. This is often called the enhanced permeation and retention (EPR) and is a form of 'passive targeting.' The basis for increased accumulation of drug-loaded nanoparticles in tumors over normal tissues is that, unlike tumor beds supplied by leaky vasculature, normal tissues contain capillaries with tight junctions that are less permeable to nanosized particles. Passive targeting can therefore result in several fold increases in particulate concentrations in solid tumors compared to free administration of antibodies or other drugs and may explain the increased survival and effective treatment of metastasis observed after intravenous injection.

This is one example of how nanolipogels can be used to advantage with regard to biodistribution. Other strategies to further increase this survival index include increasing the frequency of injections, dosage per injection or inclusion of tumor retention ligands on the surface of the nanoparticle to improve the selective delivery of agents and retention in the tumor microenvironment. The activity of tumor infiltrating lymphocytes and NK can be enhanced by the delivery of additional cytokines such as IL-15, which belongs to the IL-2 family of cytokines and which can function to enhance the survival of IL-2 activated cells.

The present invention will be further understood by reference to the following non-limiting examples.

EXAMPLES

Example 1: Preparation of Nanolipogels for Delivery of Anti-Tumor Molecules

Materials and Methods

Nanolipogel synthesis. "Nanolipogel" ("nLG") particles were fabricated from a degradable polymer (FIG. 1B). Liposomes were used as nanoscale molds for photo-initiated hydrogel formation. To achieve sustained release of the hydrophobic drug in conjunction with encapsulated proteins, methacrylate-conjugated β-cyclodextrins (CDs) were incorporated into the interior of the liposomes. β-cyclodextrins have a long history as solubilization agents for hydrophobic compounds and are key excipients in various pharmaceutical formulations. This formulation procedure enabled co-encapsulation of both proteins as well as small hydrophobic drugs within the interior of the lipid bilayer (FIG. 1A-1B).

Conjugated CDs were created by reaction of succinylated-CDs with photosensitive methacrylate groups through hydrolysable ester groups. (FIG. 1A) Complexation of SB or rhodamine (for imaging) with functionalized CD was verified by proton nuclear magnetic resonance ($^1$H NMR) on a 500 MHz Bruker spectrometer. All samples were dissolved in 1-10 mg/ml in $D_2O$ for characterization with the solvent as a reference.

PLA-PEG-PLA diacrylate was synthesized in two steps according to Sawhney, et al. *Macromole* 26, 581-587 (1993). All chemicals were purchased from Sigma unless otherwise noted and were of ACS grade or higher. α,ω-dihydroxy poly(ethylene oxide) with a molecular weight of 4000 g/mol, 3,6-dimethyl-1,4-dioxane-2,5-dione (dl-lactide), and tin(II) 2-ethylhexanoate (stannous octoate) were charged into a round-bottom flask under nitrogen in a 5:1:0.0075 mol ratio and the reaction was stirred under vacuum at 200° C. for 4 hours, followed by stirring at 160° C. for 2 hours. After cooling to room temperature, the resulting copolymer was dissolved in dichloromethane and precipitated in anhydrous ether. This intermediate was dissolved in dichloromethane (10 g/mL) and cooled to 0° C. in an ice bath. Per 10 g of polymer intermediate, 440 μL triethylamine and 530 μL acryloyl chloride were added under nitrogen and the reaction mixture was stirred for 12 hours at 0° C. and 12 hours at room temperature. The mixture was filtered and the resulting polymer was precipitated in diethyl ether. The final polymer was redissolved in dichloromethane, re-precipitated in hexanes and characterized by FTIR and NMR.

The complexation of Rhodamine and SB505124 with cyclodextrins was examined by proton nuclear magnetic resonance ($^1$H NMR) spectroscopy on a 500 MHz Bruker spectrometer.

Nanolipogel formulation. All lipids were obtained from Avanti Polar Lipids and used without further preparation. Phosphatidyl choline (PC), 1,2-distearoyl-sn-glycero-3-phosphoethanolamine-N-[amino(polyethylene glycol)-2000] (DSPE-PEG), and cholesterol were mixed in chloroform in a 3:1:1 molar ratio and liposomes were formulated using a remote loading technique of Peer, et al. Science 319, 627-630 (2008). Lipid-labeled fluorescent liposomes were formulated by incorporation of 10% 1,2-distearoyl-sn-glycero-3-phosphoethanolamine-N-[poly(ethylene glycol)2000-N'-carboxyfluorescein] (DSPE-PEG-Fluorescein). Briefly, the dissolved lipids were mixed in a glass scintillation vial, followed by complete solvent removal with a directed nitrogen stream. This formed a thin lipid film on the inner glass surfaces, which was rehydrated by the addition of 1× phosphate buffered saline (PBS). Cycles of thirty second vortexing followed by 5 min idle sitting at room temperature were repeated ten times and the resulting multilamellar liposomes were extruded 10 times through a 5 μm polycarbonate membrane (Whatman), 10 times through a 1 μm membrane and finally 11 times through a 100 nm using a LIPEX extruder (Northern Lipids, Inc.). The resulting unilamellar liposomes were then frozen and lyophilized.

Lyophilized liposomes were reconstituted with a solution containing 5% (w/v) polymer (FIG. 1B) and 2.5 mg/mL Ciba Irgacure 2959 as the photoinitiator and: no other additive (nLG-Empty), 9 mg f-CD-solubilized SB/100 mg nLG (nLG-SB; SB505124, Sigma), 1 μg IL-2/100 mg lipids (LG-IL-2; Aldesleukin Proleukin, Novartis), or both f-CD-solubilized SB and IL-2 (nLG-SB+IL-2). CD (randomly succinylated β-CD; CTD, Inc.) was functionalized with 2-aminoethyl methacrylate by stirring a 1:3 molar ratio of the compounds in 1×PBS for 1 hour at room temperature. SB was incorporated into f-CD by adding the drug dissolved in methanol to the f-CD. After 20 minutes of vigorous stirring at room temperature to form the complexes, the methanol was evaporated with a directed stream of nitrogen. The reconstitution step proceeded with 30 minutes of vortexing to rehydrate the liposomes. The liposomes were then irradiated under UV light for 8 minutes with a Blak-Ray long wave ultraviolet lamp (Model B 100) at a 10 cm working distance. Directly prior to UV irradiation, the samples were diluted fivefold to prevent macroscale gellation. The resulting nanolipogels were pelleted by centrifugation (five minutes at 7200 rcf) and resuspended in 1×PBS. This centrifugation/resuspension procedure was repeated three times. Nanolipogels were aliquotted and frozen at −20° C. until further use. For consistency, all nanolipogels were frozen prior to use (in vitro or in vivo). Final size and dispersity was confirmed by resuspending nanolipogels in 1×PBS for analysis on a ZetaPALS dynamic light scattering instrument. The zeta potential of PC/cholesterol liposomes, PC/cholesterol/PE-PEG-NH$_2$ liposomes, and nanolipogels were evaluated in 0.1×PBS using a Malvern nanosizer.

For TEM analysis, nanolipogel samples were stained with osmium tetroxide and then imaged on an FEI Tenai Biotwin microscope. Lipid-specific osmium tetroxide staining of cryosectioned samples had a localized staining pattern confined to the exterior membrane of the particle.

Results

Liposomes were used as nanoscale molds for photoinitiated hydrogel formation. To achieve sustained release of the hydrophobic drug in conjunction with encapsulated proteins, methacrylate-conjugated β-cyclodextrins (CDs) were incorporated into the interior of the liposomes. β-cyclodextrins have a long history as solublization agents for hydrophobic compounds and are key excipients in various pharmaceutical formulations.

Complexation of SB or rhodamine (for imaging) with functionalized CD was verified using $^1$H NMR. The functionalized CD (f-CD) becomes covalently bound to the liposome-encapsulated polymer matrix during photo-induced polymerization, thus the SB can only be released upon f-CD/SB hydrolysis of the polymer ester groups and subsequent diffusion out of the nanolipogel, enabling sustained release compared to the burst-dominated release of SB in the absence of gelled CD. This system enabled control over the release of remotely loaded IL-2 without compromising its bioactivity and enabled simultaneous release of both protein and drug compared to single component release. The release profile of SB/IL-2-loaded nanolipogels was not altered by incubation in serum and release was substantively completed by 7 days.

To demonstrate the impact of polymerization in the nLG on the release profile of SB and IL-2, release kinetics of both agents were compared with release from liposomes and solid poly(lactide-co-glycolide) nanoparticles (PLGA NPs) encapsulating both agents. Incorporation of photocured polymer in the nanolipogel vehicle enabled a more sustained release of SB compared to liposomes and a more complete release compared to conventional 50:50 (PLGA NPs) of the same diameter. The release kinetics of the drug is seen to be intermediate between that of diffusion dependent release from liposomes and hydrolysis dependent release from PLGA. Comparative cumulative release of IL-2 from liposomes, nanolipogels, and PLGA NPs demonstrated that encapsulation of IL-2 in nanolipogels enabled better sustained release of cytokine.

The bioactivity of the SB and IL-2 were unaffected by lipogel incorporation. Encapsulation of IL-2 (80%) and/or drug (36%) did not significantly affect nanolipogel diameter; dynamic light scattering analysis revealed a mean diameter of 120 nm and polydispersity index of 0.2. Liposomes and nanolipogels incorporating amine-terminated PEGylated phosphatidyl ethanolamine demonstrated a neutral zeta potential, compared to the approximately −22±10 mV zeta potential of liposomes formulated with only phosphatidyl choline and cholesterol. Cryo-TEM of nanolipogels showed the formation of spherical liposomal structures, detectable by light scattering even after disruption of the liposomal exterior by detergent, validating an inner gel core with approximately the same diameter as the intact nanolipogel. The in vitro cytotoxicity of this system was negligible.

To investigate the biodistribution and clearance of this platform, CD-solubilized rhodamine was used as a fluorescent surrogate marker model for SB; rhodamine complexation with CD had been previously used to qualify guest-host interactions with CDs. This was confirmed here by $^1$H NMR.

Encapsulation of SB or SB+IL-2 had no significant effect on particle mean diameter or polydispersity. FIG. 1D shows that the zeta potential of liposomes and nanolipogels incorporating amine-terminated PE-PEG was found to be close to neutral. FIG. 1E shows the composition and formulation properties of the nanolipogel formulation. FIG. 1F shows the polymer structure verified by $^1$H NMR. Cryo-TEM of nanolipogels demonstrated the formation of spherical liposomal structures. FIG. 1G shows that the photopolymerized polymer/CD forms nanoparticulate hydrogel structures that are detectable by light scattering even after disruption of the liposomal exterior by detergent.

Example 2: In Vitro Release and Bioactivity Studies

Materials and Methods

Controlled release studies. To demonstrate the advantage of nanolipogel vehicles for controlled release of encapsulated agents over prolonged periods of time, a series of studies were conducted to evaluate in vitro release of nanolipogel particles containing SB and/or IL-2. Release studies were performed at 37° C. with constant agitation in 1×PBS+10% fetal bovine serum. At each time point the complete volume was removed and replaced with fresh buffer after centrifugation (five minutes at 7200 ref). Nanolipogels were resuspended by manual pipetting. Absorbance measurements to determine SB concentrations were performed with a Beckman Coulter plate reader at 300 mu. Absorbance readings from nLG-Empty particles were subtracted from those obtained from nLG-SB particles to ensure readings were due only to encapsulated SB. IL-2 release was determined using an IL-2 ELISA kit (BD Biosciences) with humanized capture (BD, 555051) and biotinylated-detection (BD, 555040) antibodies according to the manufacturer's instructions. For IL-2 used in these studies, the international unit conversion was 22 MU=1.3 mg.

The functionalized CD (f-CD) becomes covalently bound to the liposome-encapsulated polymer matrix during photo-induced polymerization, thus the SB can only be released upon f-CD/SB hydrolysis of the polymer ester groups and subsequent diffusion out of the nanolipogel, enabling sustained release compared to the burst-dominated release of SB in the absence of gelled CD.

Bioactivity studies. Cumulative release of nLG-IL-2 was performed at 1, 3, 5, and 7 days in complete media [RPMI media (Gibco) with 10% fetal bovine serum (Atlanta Biological) and penicillin/streptomycin (Sigma) supplemented with L-glutamine (Sigma), non-essential amino acids (Gibco), Hepes buffer (Sigma), gentamicin (Sigma), and β-mercaptoethanol (Sigma)]. Splenocytes were isolated from a B6 mouse and 1×10$^6$ cells were added in 500 μL T cell media to each well of a 24 well plate previously coated with 10 μg/mL anti-CD3 (coated overnight in 1×PBS at 4° C.) and 5 sg/mL soluble anti-CD28 (BD Biosciences). The media from release studies was filtered through a 0.22-μm syringe filter (Whatman) and 500 μL was added to the wells. Additionally all wells contained 5 μg/mL soluble anti-CD28 (BD Biosciences). Soluble IL-2 was added at varying concentrations to control wells to as a standard. Cells were incubated at 37° C. and cellular stimulation was assessed after 72 hours using an IFN-γ ELISA (BD Biosciences).

Results

FIGS. 2A-2E are comparative release profiles from nLG, liposomes and solid polymer nanoparticles (PLGA). Cumulative CD- or methacrylate functionalized-CD (f-CD)-solubilized SB released from nLGs normalized by initial carrier mass demonstrated that polymerization of nanolipogels improved the sustained nature of SB release (FIG. 2A). Hydroxypropyl i-CD was used for SB complexation with the unfunctionalized CD. Cumulative IL-2 released determined by ELISA (immunoactive) and by a bioactivity study (bioactive) from nLGs normalized by initial nanolipogel mass demonstrated that bioactivity of IL-2 was unaffected by encapsulation (FIG. 2B). Release of SB and IL-2 was not affected by incubation of 10 mg nLG in 1 ml full serum (FIG. 2C). Comparative cumulative release of SB from liposomes, nanolipogels, and degradable polymeric (poly lactide-co-glycolide) nanoparticles (PLGA NPs) demonstrated that incorporation of photo-cured polymer in the nanolipogel vehicle enabled better sustained release and more complete release of cyclodextrin-solubilized SB (FIG. 2D). PLGA NPs (mean diameter=150±50 nm) were prepared by using a modified water/oil/water double emulsion technique. Liposomes were prepared in an identical manner as the nLG without the polymer core. Liposomes were loaded with IL-2 and SB similar to nanolipogels. The diminished percent of encapsulated SB released from PLGA NPs is attributed to the interaction of the relatively hydrophobic polymer with SB. All particulate formulations were dissolved in 0.1N NaOH+1% SDS to determine 100% release at 7 days (arrow) (FIG. 2D). Comparative cumulative release of IL-2 from liposomes, nanolipogels, and PLGA NPs demonstrated that encapsulation of IL-2 in nanolipogels enabled better sustained release of cytokine. Cumulative release is presented as % of total IL-2 released through 7 days. (FIG. 2E) Data in all graphs represent mean of triplicate samples ±1 standard deviation. FIG. 2F compares the sizes and loading of IL-2 and SB in PLGA, nanolipogels and liposomes.

This system enabled control over the release of remotely loaded IL-2 without compromising its bioactivity. Loading of IL-2 in the polymer hydrogel space outside of the CD enabled simultaneous release of both protein and drug. The decreased total release of both components (FIG. 2C) compared to single component release was likely due to steric limitations within the interior of the nanolipogel or decreased loading efficiency of SB and IL-2. The release profile of SB/IL-2-loaded nanolipogels was not altered by incubation in serum and release was substantively completed by 7 days.

To demonstrate the impact of polymerization in the nanolipogel on the release profile of SB and IL-2 the release kinetics of both agents were compared with release from liposomes and solid poly(lactide-co-glycolide) nanoparticles (PLGA NPs) encapsulating both agents. Incorporation of photocured polymer in the nanolipogel vehicle enabled a more sustained release of SB compared to liposomes and a more complete release compared to conventional 50:50 (PLGA NPs) of the same diameter. The release kinetics of the drug is intermediate between that of diffusion-dependent release from liposomes and hydrolysis-dependent release from PLGA. Comparative cumulative release of IL-2 from liposomes, nanolipogels, and PLGA NPs demonstrated that encapsulation of IL-2 in nanolipogels enabled better sustained release of cytokine.

Bioactivity. Nanolipogel vehicles provide the wherewithal to control release of encapsulated agents without compromising bioactivity. The bioactivity of the SB and IL-2 were unaffected by lipogel incorporation. IFN-γ production was correlated with IL-2 concentration to determine bioactivity.

Example 3: Characterization of Nanolipogels

Encapsulation of IL-2 (80%) and/or drug (36%) did not significantly affect nanolipogel diameter; dynamic light scattering analysis revealed a mean diameter of 120 nm and polydispersity index of 0.2. Liposomes and nanolipogels incorporating amine-terminated PEGylated phosphatidyl ethanolamine demonstrated a neutral zeta potential, compared to the −22±10 mV zeta potential of liposomes formulated with only phosphatidyl choline and cholesterol. Cryo-TEM of nanolipogels showed the formation of spherical liposomal structures, detectable by light scattering even after disruption of the liposomal exterior by detergent, validating an inner gel core with approximately the same diameter as the intact nanolipogel. The in vitro cytotoxicity of this system was negligible.

Example 4: Biodistribution

To investigate the biodistribution and clearance of the nanolipogels, CD-solubilized rhodamine was as a fluorescent surrogate marker model for SB; rhodamine complexation with CD had been previously used to qualify guest-host interactions with CDs. This was confirmed by $^1$H NMR. The in vivo pharmacokinetics of rhodamine following systemic administration was evaluated in healthy mice receiving a single intravenous administration of nLG-rhod, an equivalent dose of free rhodamine, or PBS control via tail vein injection.

Results

Spectrofluorometric analysis of rhodamine extracted from blood showed 15.7±4.1% and 7.7±3.7% (mean±s.d.) of the initial dose of nanolipogel remaining at 1 and 24 hours respectively post-injection. Free rhodamine was rapidly cleared and was not detectable in blood at any of the time points taken following injection.

FIGS. 3A-3G are graphs showing controlled release, clearance, and biodistribution. The distribution of both nanolipogel carrier and encapsulated drug payload was investigated using dual-labeled NLG; fluorescein-labeled phosphoethanolamine was incorporated into the lipid component of rhodamine-loaded nanolipogels. Spectrofluorimetric analysis at 540/625 nm and 490/517 nm showed dose-dependent fluorescence with no spectral overlap. FIG. 3A is a graph of cumulative IL-2 (ng/mg nLG) and drug (μg SB/mg nLG) released from co-loaded nLGs normalized by carrier mass. Error bars in all plots represent ±1 standard deviation. FIG. 3B is a graph showing clearance (percent of initial dose) of drug dose over time in days: Encapsulation in nanolipogels significantly increased the remaining percentage of initial dose in the blood at 1 and 24 hours post-injection (two population t test, p<0.01 ###). FIG. 3C is a graph of whole body distribution. Mice received a single dose of rhodamine-loaded nanolipogel or soluble rhodamine (in saline) via intravenous tail vein injection. Animals were sacrificed at 1, 24, 48, and 72 hours post-injection for extraction and quantification of fluorescence.

Whole body biodistribution was determined with rhodamine labeling. Significantly higher (two population t test, p<0.01) amounts of rhodamine were detected in the major organs of nanolipogel-treated animals compared to animals injected with free dye. FIG. 3D is a graph of time dependent accumulation n in subcutaneous tumor: Cumulative rhodamine tumor penetration (circles) after B16 peritumoral injection in B6 mice. Peritumoral tissue was collected to quantify the remaining dose of nLG surrounding the tumor (squares). Controlled release demonstrates release of rhodamine, but not lipid (FIG. 3E). Mice bearing subcutaneous B16 tumors received a single IV (tail vein) injection of dual-labeled NLG. Animals were sacrificed at 1, 2, 3, and 7 days post injection and tissues collected for homogenization, extraction, and quantification of rhodamine and fluorescein-PE. Analysis of serum showed prolonged circulation of both encapsulant and delivery vehicle. Similar patterns of biodistribution were observed between lipid (FIG. 3F) and drug payload (FIG. 3G), with highest accumulations of drug occurring in the lungs and liver.

Analysis of the biodistribution to major organs showed that the lungs, liver and kidney were primary sites of accumulation of both nanolipogel-encapsulated rhodamine and free rhodamine. Encapsulation in nanolipogel increased both the total initial dose to most tissues as well as the cumulative dose over three days.

Example 5: Cytotoxic and Safety Studies

Materials and Methods

Cell titer blue (Invitrogen) was used as a cell viability marker according to the manufacturer's instructions. Chinese Hamster Ovary—(CHO) cells (ATCC) were placed in 96 well plates at a density of $5 \times 10^4$ cells/well (except the standard, which contained a serial dilution of the number of cells). Cells were incubated for 24 hours at 37° C. with serial dilutions of 1×PBS (positive control), sodium azide (negative control; Sigma), liposomes, or nanolipogels. Liposomes were fabricated similarly to nanolipogels but, after lyophilization, were reconstituted with pure 1×PBS and were not subjected to UV irradiation. Nanolipogels were from the nLG-Empty group. After 24 hours the cell titer blue reagent was added (20 μL/100 μL volume). The cells were further incubated for 4 hours at 37° C., after which they were pelleted and the fluorescence of the supernatant was measured. 100% cell survival is defined as the average of survival from the 1×PBS group and 0% survival that from the azide group. All samples were run in triplicate and the experiment was repeated three times with similar results.

To examine the in vivo safety of nanolipogel particles, C57/B16 mice were administered a single intravenous dose of nanolipogels and acute toxicology was measured 7 days later. Lung toxicity was evaluated by histology to determine if systemically administered nanolipogels induced any acute inflammation.

Results

No statistically significant toxic effects were observed from the administration of empty nanolipogels or nanolipogels co-encapsulated with SB505124 (SB) or IL-2. No hepatotoxicity was observed, as measured by serum levels of alkaline phosphatase and alanine aminotransferase. Normal physiological reference ranges given by the IDEXX VetTest® system for mouse alkaline phosphatase and alanine aminotransferase were 62-209 IU/L and 28-132 IU/L, respectively. Furthermore, no renal toxicity was observed, as blood urea nitrogen levels were within the normal mouse reference range of 18-29 mg/dL. A complete blood count was also performed to identify any hematological toxicity. Leukocyte counts, platelet counts, and hemoglobin content were all within normal physiological ranges for mouse (leukocytes: $1.8\text{-}10.7\times10^3$ cells/uL; platelets: $592\text{-}2971\times10^3$ cells/uL; hemoglobin: 11.0-15.1 g/dL). Hematoxylin and eosin staining of lungs demonstrated no obvious pulmonary toxicity. Bronchiolar and alveolar structures appeared normal, and no disruption to epithelial layers or inflammatory infiltrates were observed in lung sections.

The in vitro results demonstrate that nanolipogels have similar negligible toxicities to liposomes.

Healthy C57/B16 mice were administered a single intravenous dose of nanoparticle combination therapy or controls and acute toxicology measured 7 days later. No significant toxicities were observed in serum measurements of alkaline phosphatase or serum alanine aminotransferase. Normal physiological ranges for mouse alkaline phosphatase are approximately 62-209 IU/L and for alanine aminotransferase approximately 28-132 IU/L. No renal toxicity was observed, as blood urea nitrogen levels were within the normal mouse reference range of 18-29 mg/dL. Complete blood counts demonstrated that normal physiological ranges leukocyte counts, platelet counts, and hemoglobin content. Lung toxicity was evaluated by histology to determine presence of acute inflammation. Hematoxylin and eosin staining of lungs demonstrated no obvious pulmonary toxicity or inflammatory infiltrates; bronchiolar and alveolar structures appeared normal with no disruption to epithelial layers.

Example 6: Drug Delivery to Tumors and Antitumor Activity—Subcutaneous Tumors The effects of IL-2 and TGF-β antagonist monotherapies to enhance the antitumor responses against B16 melanomas were determined.

Materials and Methods

A paired t test (two-tailed) was used to analyze differences in tumor areas and masses. OriginPro version 8.1 (Microcal) and Prism version 5.01 (GraphPad Software, Inc.) were used for the analyses. Survival studies were analyzed using the Kaplan-Meier and Wilcoxon-Gehan tests with Origin.

In vivo subcutaneous tumor studies. B16-F10 cells (ATCC) were cultured in DMEM (Gibco) and suspended at $2\times10^6$ cells/mL in 1×PBS (kept on ice) directly prior to injection. For subcutaneous tumor studies, female 6-8 week-old B6 albino mice were sedated with AErrane (isofluorane; Baxter) and the right hind flank was shaved prior to a subcutaneous injection of 50 µL of the cellular suspension. Tumors were monitored and treatment began when the average tumor area reached approximately 5.5 mm² (8-10 days after B16 injection; mice were rearranged to normalize tumor sizes across groups). Mice were sedated with isofluorane for intratumoral nanolipogel administration. Each dose consisted of 5 mg nanolipogels.

Observers were blinded for tumor area and survival studies. Mice were euthanized with carbon dioxide when any one tumor dimension was greater than 15 mm, when exhibiting any sign of sickness, or at one week post-treatment for FACS analyses studies. The in vivo delivery study used 5 mg injections/mouse of f-CD-solubilized rhodamine (Sigma)-loaded nanolipogels, prepared as described above for nLG-SB. Five mice per group were euthanized at different timepoints and tumors were extracted and weighed.

Rhodamine was extracted by homogenizing the tumors in 500 µL deionized water (DI). Two freeze/thaw cycles at −80° C./room temperature were used to ensure cells were completely lysed then homogenates were thawed to room temperature and 40% (v/v) dimethylsulfoxide and 1% (v/v) TWEEN® 80 were added to dissolve particles. After vortexing, the homogenates were frozen at −80° C. for 24 hours, thawed at room temperature and vortexed for 10 minutes, then cellular debris was pelleted by 30 minutes centrifugation at 13000 rpm. The supernatant was removed and fluorescence was measured with excitation 540 nm/emission 625 nm.

In Vivo Nanolipogel

As encapsulation in nanolipogels decreased clearance of free drug and improved biodistribution, localized therapy of subcutaneous tumors was evaluated first to assess therapeutic efficacy. Weekly intratumoral administration of soluble SB alone failed to delay tumor growth (FIG. 4A), consistent with previous results using LY364947 in preclinical prostate and gastric animal cancer models. A similar null effect was observed when both soluble SB and IL-2 were co-administered in weekly doses (FIG. 4A). The nanolipogel encapsulated SB administered individually (nLG-SB) significantly delayed tumor growth (FIG. 4A), resulting in mice with smaller tumors after one week of therapy (FIG. 4B). Although nanolipogel encapsulated IL-2 administered individually (nLG-IL-2) did not significantly delay tumor growth (FIG. 4A), the tumor masses at one week were significantly smaller than tumors obtained from mice in the control group (FIG. 4B).

These results are in accord with prior studies demonstrating the efficacy of sustained release of either IL-2 or small molecules inhibiting TGF-β signaling over pulses of these agents for enhancement of antitumor responses. When comparing all treatment groups, the most striking and significant reduction in both tumor growth rate and tumor mass after one week of therapy was observed in the mice receiving simultaneous sustained delivery of SB and IL-2 (FIGS. 4A and 4B).

Results

Tumor size in treated and untreated mice correlated with their survival (FIG. 4A; 4C). Administration of soluble SB or SB in combination with IL-2 did not improve survival over untreated controls, while nanolipogel formulations of IL-2 or SB alone modestly increased average survival times (FIG. 4C). In contrast, the nanolipogel-delivered combination immunotherapy dramatically increased survival (FIG. 4C). As observed with the tumor kinetics data, administration of particles releasing each agent slightly improved survival; however, mice receiving combination therapy via particles releasing both agents demonstrated markedly smaller tumors and longer survival compared to the other treatment groups. Of the animals receiving nLG-SB+IL-2, 100% survived through the study endpoint at 35 days after initial tumor implantation. Complete tumor regression and survival was observed in a cohort (40%) of the group through 60 days. (FIG. 4C)

Drug delivery to tumors following localized peritumoral injection of rhodamine-loaded nLG (nLG-rhod) was evaluated by comparative measurement of rhodamine concentrations in tumors versus peritumoral tissues. The pharmacokinetic profile suggested sustained delivery of drug from the localized depot of nLG: at 24 hours after peritumoral administration, only 3±1% of the initial dose had penetrated into the tumor mass and 36±17% of the initial dose remained in the surrounding tissues. Over the course of 7 days, the cumulative rhodamine concentration in the tumor increased to 25±0.5% of initial dose, while total rhodamine concentration in the peritumoral tissue decreased to 4±2% of initial dose.

Example 7: In Vivo Nanolipogel Biodistribution, Safety, and Metastatic Lung Tumor Studies A significant unmet need is improved biodistribution of short-lived cytokines and hydrophobic drugs in the treatment of distant metastatic tumors. Genetically modified mice containing T-cells resistant to TGF-β signaling abrogated the development of metastatic B16 melanoma deposits in the lungs, providing additional motivation for assessing TGF-0 blockade with and without IL-2 therapy in this tumor model. The effect of systemic nanolipogel therapy against highly aggressive B16 lung metastases was tested in this model. It has previously been shown that intravenous injection of B16 cells results in rapid metastatic tumor growth in the lungs of B6 mice.

Materials and Methods

Metastatic B16 melanomas were established in female 6-8 week old B6 mice by intravenous (tail vein) administration of 50 μL of B16 cellular suspension as described by Gorelik, et al. *Nat Med* 7, 1118-1122 (2001). Treatment was initiated 7 days later with each dose consisting of 5 mg nanolipogels administered intravenously via tail vein injection. Mice were euthanized when exhibiting external tumor growths, paralysis or weakness, significant weight loss, or at 14 days after the first treatment for FACS analyses studies. After sacrifice, the chest cavity was exposed and the lungs perfused by making a small incision in the right atrium and injecting 10 mL of cold PBS into the right ventricle. Lung metastases were counted by blinded observers who recorded dark circular masses ranging from 0.1-3 mm as unique tumors.

Biodistribution studies of nanolipogels were conducted in healthy and tumor-bearing mice after injection (local or systemic) of 5 mg of f-CD-solubilized rhodamine-loaded nanolipogels (with or without fluorescein-labeling of the lipid carrier). Rhodamine was extracted from homogenized tissues and quantified as described above. Acute toxicology was assessed in healthy C57/B16 mice seven days after an intravenous dose of buffer control, empty nanolipogels, or SB and IL-2-loaded nanolipogels. Hepatoxicity and renal toxicity were assessed via measurement of serum alkaline phosphatase, alanine aminotransferase and blood urea nitrogen levels. A complete blood count was performed to identify any hematological toxicity. Finally, lung toxicity was evaluated by histology to determine if systemically administered nanolipogels induced any acute inflammation.

Resected tumor tissue was fixed in 10% formalin for 24 hours and then embedded in paraffin. Tissue blocks were sectioned into 5 um slices and mounted on glass slides followed by hematoxylin and leukocyte staining anti-LCA (CD45)-peroxidase conjugate (1 ug/ml) (Life technologies).

An Olympus BX61WI fluorescence microscope in combination with a 20×, 0.95NA Olympus objective and LaVision Biotec two-photon microscopy system was used for imaging tumor vasculature and nanolipogel accumulation in tumors. Briefly, incisions were made to expose skin flaps surrounding subcutaneous tumors on anesthetized C57BL/6 mice. Intravital image acquisition was started 5 minutes after intravenous administration of nanolipogels. An auto-tunable Titanium-Sapphire two-photon laser (Chameleon Vision II, Coherent) pumped by a Verdi laser source was used for the excitation light source. Emitted light was collected with non-descanned detectors outfitted with the following bandpass filters: 435/90 nm, 525/50 and 615/100. The field of view for each xy plane was either 400 μm×400 μm or 500 μm×500 m, at a resolution of 0.8 um per pixel. Stacks of between 26 and 101 optical sections with 1 or 2 μm z spacing were acquired every 60 s over the course of one hour with the laser set at a wavelength of either 850 nm or 940 nm. Volocity® software (Improvision) was used to create sequences of image stacks.

Results

Tumor infiltrating lymphocytes were isolated from B16 melanomas as described by Petersen, et al. *J Immunother* 29, 241-249 (2006). Treatments were given by tail vein injection and were initiated one week after cell injection to assess efficacy against growing tumors. As was the case in mice bearing subcutaneous tumors, maximum survival benefit was observed in the group receiving the nanolipogel-encapsulated combination therapy. Mantel-Cox analysis demonstrated a statistically significant (p<0.01) increase in survival over animals receiving saline alone, i.e., no treatment (FIG. 5a). Half of the animals receiving nLG-SB+IL-2 survived through the study endpoint at 45 days. (FIG. 5a)

To examine the effect of treatment on tumor burden, animals were sacrificed two weeks after initial treatment and whole lung samples inspected visually for melanoma deposits. Administration of soluble SB with or without IL-2 co-therapy failed to reduce the number of lung tumors at three weeks (Figure Sb). Maximum tumor burden reduction was observed in animals receiving the nanolipogel-delivered combination therapy (FIG. 5b).

Comparative biodistribution was repeated in mice bearing B16 metastatic lung tumors. Dual-labeled nanolipogels formulated by incorporating fluorescein-labeled PEG-phosphoethanolamine into the lipid membrane of rhodamine-loaded nanolipogels were used to assess trafficking of the particles versus trafficking of the payload. Fluorescein-labeled PEG did not interfere with detection or release of rhodamine. Lung tumor-bearing mice received a single IV (tail vein) dose of dual-labeled nanolipogel. B16 metastases were often visible as approximately 1 mm irregular nodules under bright field observation while the fluorescein-labeled lipid of the delivery vehicle and rhodamine were detected under fluorescent filters up to 24 hours post administration. Fluorescent detection of lipid was significantly diminished by 4 days after administration.

To test for accumulation of nanolipogel and drug in distant tumors beyond lung tissue, biodistribution experiments were repeated in mice bearing distant subcutaneous tumors. Following intravenous injection, lipid and rhodamine concentrations were quantified in subcutaneous tumors and in homogenized tissues at various time points after administration. Peak tumoral concentrations of lipid and rhodamine, 8.8±4.0% and 2.5±0.8% per gram of tumor, respectively, were observed one day after administration. An analysis of all tissues confirmed biodistribution patterns that were similar for both the lipid and rhodamine components of the nanolipogel system indicating that the drug payload was associated with the particles during biodistribution. Trafficking of nanolipogels and payload within the vasculature of tumors was validated by imaging subcutaneous tumors with time-resolved two-photon laser scanning intravital microscopy after intravenous injection. Accumulation of fluorescein-labeled nanolipogels along the vasculature was detected both in the areas surrounding tumors as well as within the tumor itself within 30 minutes post-intravenous injection. Particle trafficking in the tumor vasculature was accompanied by an increase in the encapsulant fluorescence in the tumor microenvironment. Extravasation of rhodamine was evident in peritumoral tissue as well as the interstitial spaces between tumor cells.

Fluorescein-labeled PEG did not interfere with detection or release of rhodamine. An analysis of all tissues confirmed biodistribution patterns that were similar for both the lipid and rhodamine components of the nanolipogel system as well as within the tumor itself within 30 minutes post-intravenous injection.

Example 8: Immunological Mechanisms of Antitumor Effects of Nanolipogels

Materials and Methods

In order to elucidate the immunologic mechanisms behind the therapeutic effects of the sustained release combination therapy and the relative contribution of each agent delivered as monotherapies, tumor infiltrating lymphocytes (TILs) were harvested and evaluated in mice euthanized one to two weeks after the initial therapeutic dose. This time point was chosen based on when mice in all groups had developed either subcutaneous tumors of sufficient size (up to 10 mm in greatest dimension), or sufficient numbers of lung tumors (more than five), to isolate adequate number of TILs for analysis.

Tumor infiltrating lymphocytes were isolated from B16 melanomas. In brief, subcutaneous tumors or lung tumors were resected from mice; weighed, minced into sections approximately 3 mm in greatest dimension, then placed in 8 mL of serum-free RPMI media (Irving Scientific Santa Anna, CA) containing 175 U/mL of Collagenase IA (Sigma, no. C9891) for subcutaneous tumors or 100 U/mL of Collagenase IV (MP Biomedical, no. 195110) for lung tumors. The resulting tissue suspension was incubated at 37° C. for 1 hour, passed through a 70-gin tissue filter and the resulting cells were washed twice in serum free RPMI media. The pellet was resuspended in 0.5 mL of RPMI media then overlaid over mouse lympholyte-M media (Accurate Chemical, Westbury, NY) for lymphocyte isolation, followed by centrifugation at 1500×g per the manufacturer's instructions (Accurate Chemical). The resulting buffy coat layer was removed and washed in RPMI media as described above and subsequently resuspended in 1 mL of 1×PBS containing 0.5% bovine serum albumin (Sigma). All cell suspensions were counted to determine absolute numbers of isolated TILs and subsequently distributed to 96 well-plates for FACS staining and analysis.

A Becton Dickenson LSRII flow cytometer was used to quantify the percentage of immune effector cells ($CD4^+$, $CD8^+$ T-cells and NK cells) as well as Tregs in the tumor-bearing mice by evaluating the cell surface expression of CD4, CD8, NK1.1, TCR-beta as well as intracellular FoxP3 as per manufacturer's instructions (eBioscience, San Diego, CA). Absolute cell numbers were assessed by direct counting on a Coulter cell counter. Anti-CD4 (Pacific Blue-conjugated, no 558107) anti-CD8-a (Peridinin-chlorophyll-protein (PercP) conjugated, no. 553036), anti-NK1.1 (Fluoroscein isothyocyanate (FITC) conjugated, no. 553164), anti-TCR-beta (allophyocyanin (APC)-conjugated, no. 553174), anti-CD44 (FITC-conjugated, no. 553133) and anti-CD62L (APC-conjugated, no. 553152) were purchased from Becton Dickenson Pharmingen. The anti-FoxP3 kit (containing phycoerytherin-conjugated FoxP3 antibody, no. 72-5775-40) was purchased from eBioscience.

Cells were incubated with 40 µL antibody cocktails diluted appropriately (per vendor instructions) in 1×PBS containing 0.5% BSA and a 1:200 dilution of Fc blocking antibody 2.4G2 (anti-CD16/32) to prevent nonspecific binding. Cells were incubated with the antibody cocktails for 30 minutes at 4° C. then washed once prior to analysis on LSRII Green flow cytometer. For intracellular staining of FoxP3, cells were fixed, permeabilized and stained using a FoxP3 staining kit purchased (eBiosciences).

All FACS data were analyzed using FloJo software (Tree Star Inc., Ashland, OR). Absolute CD4 Tregs, CD8 T-cells and NK cells were determined by multiplying the absolute numbers of TILs normalized per gram of tumor by the percentages (gated first on live, TCR-$\beta$+/−) of $CD4^+$/$FoxP3^+$, $CD8^+$ or NK1.1+/TCR-Q cells measured by the LSRII Green flow cytometer. CD8/Treg ratios were obtained by dividing the absolute number of CD8 T-cells by the absolute number of regulatory T-cells.

NK1.1 antibodies were isolated from HB191 hybridoma as described by Yokoyama, W. M. Monoclonal antibody supernatant and ascites fluid production, in *Curr Prot Immunol* (ed. Margulies, D. H.) 2.6.1-2.6.9 (John Wiley & Sons, New York, 2000). These antibodies were injected intraperitoneally one day prior to B16 injection and every seven days thereafter. Each injection was 250 µL of a 1 mg/ml solution.

To confirm the NK depletion occurred successfully in mice treated with the NK1.1 antibody, approximately 300 microliters of blood and the spleens of NK depleted and NK proficient mice were obtained. Peripheral blood and splenocytes which were obtained using mechanical dissociation were treated with ACK lysis buffer (Lonza, Walkersville, MD) as per manufacturers protocol and subsequently stained for NK1.1 or TCR-$\beta$ using the antibodies described in the text. Percentages of NK1.1/TCR-beta negative cells indicated in right lower quadrants in Supplementary FIG. 8, which show successful NK depletion with anti-NK1.1 antibodies.

Results

The effects of IL-2 and TGF-$\beta$ antagonist monotherapies to enhance the antitumor responses against B16 melanomas were evaluated. As encapsulation in nanolipogels decreased, clearance of free drug and improved biodistribution, resulting in mice with smaller tumors after one week of therapy, the tumor masses at one week were significantly smaller than tumors obtained from mice in the control group.

Administered in nanolipogels alone or in combination with SB, IL-2 increased both the percentage and absolute numbers of activated $CD8^+$ T-cells in tumors (FIG. 6a; FIG. 6b) with minimal impact on overall CD4/CD8 ratios and $T_{regs}$, results that were consistent with reported clinical outcomes. Representative histological images of tumors showed that IL-2 significantly increased lymphocyte infiltration into tumors. Sustained administration of this cytokine also increased activated $CD8^+$: $T_{reg}$ ratios in TIL populations. (FIG. 6c)

Treatment with nLG-SB significantly increased activated $CD8^+$ populations (P<0.05), as did treatment with nLG-IL-2 or nLG-SB+IL-2 (P<0.001), over unloaded particles (nLG-Empty). All groups have significantly greater ratios (P<0.05) compared with empty nLGs.

These data, however, did not fully explain the observed results in mice receiving particles releasing both IL-2 and SB, suggesting another mechanism may be involved in the enhanced antitumor effects observed in the treated mice. Since TGF-$\beta$ can also regulate NK cell number and function, it was assessed whether this cell type was involved in the innate arm of the immune system present in TILs. In stark contrast to the relative number of TIL $T_{regs}$ observed in all tumor bearing mice, sustained administration of SB in combination with IL-2 resulted in substantially increased percentage (FIG. 6a) and absolute numbers (FIG. 6c) of NK cells present in tumor beds compared to groups receiving either "empty" particles or particles releasing either IL-2 or SB alone.

To validate that the therapeutic benefit observed in mice treated with particles releasing both agents was NK-dependent, studies were performed in NK-depleted mice. NK1.1 antibodies were used to deplete mice of NK cells and tumor cells were injected in NK-depleted mice and mice retaining NK cells. Mice were again euthanized one week after the initial treatment and tumor masses were measured.

Compared to the empty particle group, significantly more NKs were present in the lungs following treatment by nLG-SB+IL-2 ($P<0.05$), nLG-SB ($P<0.05$), and nLG-IL-2 ($P<0.01$). The nLG-SB+IL-2-treated group has significantly more NKs than the control group ($P<0.01$), the SB-treated group ($P<0.05$), and the IL-2-treated group ($P<0.01$). The nLG-SB+IL-2-treated WT group has significantly smaller tumors than all other treatment groups ($P<0.001$). The NKD nLG-SB and nLG-SB+IL-2 groups have significantly larger tumors than their WT counterparts (both $P<0.001$). Studies were repeated 2-3 times with similar results.

NK depletion did not affect the sizes of tumors in mice receiving particles releasing IL-2 alone (FIG. 6b). In contrast, absence of these cells abrogated the delay in tumor growth in animals receiving particles releasing SB and IL-2 (FIG. 6b). There was a modest therapeutic benefit in mice receiving particles releasing drug alone that was abrogated by NK depletion (FIG. 6b). There was a modest, statistically significant increase in NK cells in the TILs of mice treated with particles releasing SB alone (FIG. 6c).

Thus, the maximum therapeutic benefit observed in mice treated with particles simultaneously delivering SB and IL-2 therapies was likely related to enhanced numbers of NK cells at the tumor site, resulting in increased effector cell populations in the tumor.

Importantly, the clinical effects following systemic therapy were consistent with the results of localized therapy and drug biodistribution. Encapsulation in nanolipogel increased both the initial dose to the lungs as well as dose persistence over a three day period; on the third day after administration, 9.0 f 0.8% (mean t s.d.) of the initial dose of nanolipogels was measured in the lungs compared to 1.5 & 0.7% of soluble drug. This pharmacokinetic effect correlates with increased survival and a significant decrease in the number of tumors. Analysis of lung-infiltrating lymphocytes demonstrated that, as observed in subcutaneous tumors receiving intratumoral nLG-SB+IL-2 treatments, enhanced numbers of activated $CD8^+$ (FIG. 5a) and NK (FIG. 6a) effector cells mediated tumor abrogation and increased survival. These data indicate that significant antitumor responses against metastatic melanoma can indeed be achieved by the sustained, combined delivery of a TGF-β inhibitor drug and IL-2 in a clinically-relevant mode of administration.

Example 9: Comparative Distribution of Nanolipogel Carrier and Encapsulant

Materials and Methods

The distribution of both nanolipogel carrier and encapsulated drug payload was investigated using dual-labeled nanolipogels. Fluorescein-labeled phosphoethanolamine was incorporated into the lipid component of rhodamine-loaded nanolipogels. Spectrofluorimetric analysis at 540/625 nm and 490/517 nm demonstrated a dose-dependent fluorescence with no spectral overlap. There was controlled release of rhodamine, but not lipid.

Mice bearing subcutaneous B16 tumors received a single IV (tail vein) injection of dual-labeled NLG. Animals were sacrificed at 1, 2, 3, and 7 days post injection and tissues collected for homogenization, extraction, and quantification of rhodamine and fluorescein-PE.

Results

Analysis of serum showed prolonged circulation of both encapsulant and delivery vehicle. Similar patterns of biodistribution were observed between lipid and drug payload, with highest accumulations of drug occurring in the lungs and liver.

Example 10: Lipid Encapsulated Dendrimers for Combined Delivery of Nucleic Acids, Proteins, and Drugs The nanolipogel encapsulating dendrimers includes a main shell consisting of a liposome encapsulating a drug and siRNA/dendrimer complex which inserts in cells. Dendritic polymers (dendrimers) are a class of monodisperse polymers distinguished by their repeated branching structure emanating from a central core. This branching, which is inherent in the divergent synthesis of dendrimers, leads to a geometric growth of the polymer that can nearly approximate a sphere with increased branchings or higher generations (generation 6 or above). This branching creates a core ideally suited for entrapment of a variety of small hydrophobic molecules such as drugs as well as complexation of nucleic acids. For example, SUPERFECT® is a commercially available activated dendrimer transfection agent. Combined with their narrow molecular weight distribution and small size (less than 10 nm), dendrimers have been utilized for a large number of applications including drug and gene delivery. Dendrimers complexed with nucleic acids can be cleared rapidly upon in vivo administration and hence protective targeting of this complex would be a more attractive modality for site-specific delivery. The liposomal formulation serves two functions: 1) Protective encapsulation of siRNA complexed liposomes and 2) facilitating delivery of small molecule hydrophilic drugs such as rivoavrin or proteins such as IFNα. Complexation of the inner dendrimer core with siRNA: Nucleic acids are generally stabilized by cationic polymers in a polyplex formation akin to the physiological packaging of nucleic acids around histones. Cationic polyamidoamine (PAMAM) dendrimers, generation 5 (G5), diameter 5.4 nm, serves this purpose.

Materials and Methods siRNA/Dendrimer polyplexes are formed by combining G5 PAMAM and siRNA at an amine to phosphate (N/P) ratio of 1:1 to 10:1. The precise ratio which will yield optimal silencing can be determined by mixing stock siRNA and PAMAM at different molar ratios for 30 min at room temperature in sterile 10 mM HEPES buffer, pH 7.2 with light vortexing. This procedure yields a siRNA-dendrimer polyplex with a charge (zeta potential) of +20 or above and effective diameter of 10 nm, which is suitable for encapsulation in liposomes. Next, the polyplex is co-encapsulated with the drug (IFNα and/or Ribavirin) in the liposomal particle. A dehydrated lipid film comprised of distearoyl-glycero-phosphocholine (DSPC), cholesterol, and distearoylglycero-phosphoethanolanine (DSPE) with an amine terminated polyethylene glycol (PEG2000) spacer (DSPE-PEG2000-NH2) is first mixed in the molar ratio of 65:30:5, then rehydrated under sonication with a 10 mg/ml solution of siRNA/Dendrimer polyplex and drug. The ratio of drug to siRNA/dendrimer in solution can be tuned during formulation. Optimal ratio is dictated by in vitro and in vivo efficacy studies. The intrinsic "built-in" lipid PEGylation facilitates a longer circulation time compared to particles without PEG. PEG incorporation yields a steric hydration barrier shield which facilitates long-lived in vivo circulation. (i.e avoidance of the reticuloendothelial system and non-specific uptake by macrophages).

Following the mixing of drug and siRNA/Dendrimer polyplex in presence of lipids, the solution is extruded through a series of filters. First three times through a 5 µm filter, three times through 1 µm filter, and five times through a 200 nm filter collecting extrudate in a sterile tube. Excess siRNA complex, drug and lipids are removed by spinning for 45 minutes at 24000 rpm at 4 C (3×) in an ultracentrifuge.

FIG. 7A is a schematic of LED preparation encapsulating siRNA/dendrimer polyplex and drug combinations, with covalent modification of the outer shell with targeting antibodies or single chain variable fragments (scFv). Attachment of antibodies or scFv to the amine terminated liposome is achieved by activating the protein in 0.1 MES buffer (pH 5.5) in the presence of ethyldicarbodiimide and N-hydroxysuccinimide for 10 min followed by addition to particles in buffered saline (pH 7.4). This reaction activates carboxylate groups on the protein for covalent linkage to exposed amine groups on the particles (ref). Initially, the reaction stoichiometry is adjusted to yield an approximate density of 1-10 scFv molecules per particle, however, this density can be easily increased by varying the stoichiometry of the reaction to facilitate maximal internalization. Total time for the reaction is 30 min at room temperature. These reaction conditions have no effect on the integrity or function of encapsulated agents.

LEDs were tested for the ability to deliver a functional expression vector (pGFP) into BMDC, HeLa, 293T cells using different methacrylate-conjugated β-cyclodextrins (CDs) and Nitrogen/Phosphorus (N/P) ratio, and compared to vector delivery using LIPOFECTAMINE® 2000 and liposomes.

LEDs were also tested for the ability to deliver functional siRNA. Jurkat (human T cell line) were incubated with LEDs encapsulating siRNA against CD4 or Luciferase (Luc) and surface functionalized with anti-CD7 to mediate internalization.

Results

LEDs can facilitate drug internalization as depicted in FIG. 7A with macrophages in culture. The drug Methotrexate (MTX) was used as a model drug. FIG. 7B shows the cytotoxicity of LED and LED encapsulating the model drug methotrexate (MTX). Bars indicate successive dilutions of LED or drug or combinations starting from (1 mg/ml left to right to 10 µg/ml). Azide is used as a positive control for cell killing. Starting at 10%, left to right, and increasing to 1%, the graph shows that, compared to free drug (MTX), LED containing MTX were slightly less toxic, presumably because of drug sequestration. LEDs alone showed no cytotoxicity.

LEDs encapsulating the dye rhodamine facilitate internalization and cytoplasmic localization of the dye and LEDs containing the pGFP plasmid showed enhanced efficiency in transfection of macrophages compared to a standard transfection agent such as LIPOFECTAMINE®.

To determine if terminal amine groups on PAMAM dendrimers provide endosomal buffering and disrupt endosomes by the proton sponge effect, an Acridine Orange (a dye whose spectral properties change depending on its location in endosomes or cytosol) assay was used with BMDCs, which were treated with unmodified generation 4 PAMAM dendrimers (G4), or dendrimers conjugated to cyclodextrin molecules (CD) that substituted and shielded primary amines with or without ionophore carbonylcyanide-p-trifluoromethoxyphenylhydrazone (FCCP). The results indicate that of the tested combinations, unmodified 04 dendrimer was best at endosomal disruption followed by G4-3CD (FIG. 7C). G4-6CD was the least effective at endosomal disruption of the combinations tested, supporting the idea that proton sponge effect is mediated by primary amines and substituting amines with CD decreases buffering capabilities.

LEDs were also tested using different dendrimer (G)-cyclodextrin conjugates (CDs) and Nitrogen/Phosphorus (N/P) ratio, and compared to vector delivery (pGFP) using LIPOFECTAMINE® 2000 and liposomes in a variety of cells types. CD significantly affected dendriplex (FIG. 7D). Dendriplexes (from modified dendrimers) transfect better than Lipofectamine 2000 in BMDCs. LEDs also transfected better than liposomes encapsulating vector in BMDCs.

LEDs encapsulating siRNA against CD4 or Luciferase (Luc) and surface functionalized with anti-CD7 were test for the ability to mediate internalization target mRNA knockdown in Jurkat (human T cell line) cells. Results indicated that LED delivered siRNA reduced surface expression of CD4, or Luc relative to controls (FIG. 7E).

In a second experiment, LEDs including 200 ug of dendrimer and 400 µmol siGFP (Ctl=LFA:siGFP) were utilized to knockdown GFP expression is a stably transfected cell line. Stable 293T-eGFP cells were treated with dendrimers for 4 h in SFDMEM followed by examination of GFP expression. Cells treated with most dendrimer (G)-cyclodextrin conjugates (CDs) combinations exhibited greater reduction in GFP expression compared to mock and LIPOFECTAMINE®:siGFP controls (FIG. 7F).

Example 11: Antigen Cross Presentation with Lipid Encapsulated Dendrimers

Materials and Methods

Mouse Bone Marrow-Derived Dendritic Cells (BMDCs) were incubated with liposomes encapsulating ovalbumin (OVA) alone, dendrimer alone, or both OVA and dendrimer (LED).

Results

Controls of cells and empty liposomes showed undetectable levels of 25.D16 antibody staining, which binds MHC Class I-SINFEKL complexes. Cells receiving LEDs showed the highest level of antigen cross-presentation. *$p<0.05$ by one-way ANOVA Bonferroni post-test. (See FIG. 8A).

Example 12: Vaccine Delivery with Lipid Encapsulated Dendrimers

Materials and Methods

Antigen Presentation $1\times10^5$ BMDC/well (96 well plate)+25 uL liposomal particles. Particle groups:

a. −/− (nothing outside nothing inside particles)
b. −/OVA (nothing outside, OVA encapsulated)
c. −/G5+OVA (nothing outside, OVA and G5 dendrimer inside)
d. −/G5+OVA+CpG
e. MPLA/− (MPLA outside, nothing inside)
f. MPLA/OVA
g. MPLA/OVA+G5
h. MPLA/OVA+G5+CpG (MPLA outside; OVA, G5 dendrimer, CpG encapsulated)

Where OVA=ovalbumin, MPLA=monophosphoryl lipid A, G5=generation 5 dendrimer, CpG=CpG oligonucleotide (TLR9 ligand).

Treatment was incubated with BMDC for 24 hours followed by 4 day co-incubation with WT splenocyte.

Analysis of Pro-Inflammatory Cytokine Production

BMDCs were incubated with liposomal nanoparticles encapsulating antigen and surface-functionalized with increasing amounts of TLR ligand CpG for 24 hours before supernatant analysis by ELISA.

Results

Cells were stained with 25.D16-PE, an antibody that is specific for mouse MHC Class I-SIINFEKL complexes, as assessed for antigen cross-presentation by flow cytometery. The results indicated that −/OVA particles induce some cross-presentation, which was increased by OVA particles containing dendrimer. Particles combining MPLA, CpG, and dendrimer induce the highest amount of cross-presentation. (See FIG. 8B). Liposomal nanoparticles surface functionalized with CpG also induced a dose-dependent increase the production of pro-inflammatory cytokine IL-6. (See FIG. 8C, comparing blank particles, 0.1 µg CpG/mg particles, 0.25 µg CpG/mg particles, and 0.5 µg CpG/mg particles).

Modifications and variations of the compositions and methods of manufacture and use thereof will be obvious to those skilled in the art from the foregoing detailed description and are intended to come within the scope of the appended claims. All references are specifically incorporated.

We claim:

1. A nanolipogel comprising:
   (a) a polymeric matrix core comprising a host molecule that is reversibly complexed with at least one therapeutic, diagnostic or prophylactic active agent to be delivered, such that the or each active agent can be released under in vivo conditions, and
   (b) a lipid shell;
   wherein the or each therapeutic, diagnostic or prophylactic active agent is a nucleic acid.

2. A nanolipogel according to claim 1, wherein the or each nucleic acid is a DNA molecule such as a gene or cDNA molecule; or is an RNA molecule such as an inhibitory RNA, a tRNA, an rRNA, or an mRNA; or is an expression vector encoding a gene or cDNA of interest.

3. A nanolipogel according to claim 1, wherein the polymer matrix core comprises a dendrimer core that is reversibly complexed with the or each nucleic acid.

4. A nanolipogel according to claim 3, wherein the dendrimer is a cationic polyamidoamine (PAMAM) dendrimer.

5. A nanolipogel according to claim 4, wherein the cationic polyamidoamine (PAMAM) dendrimer is a G5 PAMAM dendrimer.

6. A nanolipogel according to claim 1, wherein the or each nucleic acid is reversibly complexed with a cationic polymer such as polyethyleneimine (PEI).

7. A nanolipogel according to claim 1, further comprising one or more additional active agents which are reversibly complexed with the host molecule, and/or dispersed within the polymeric matrix, and/or dispersed in or bound to the lipid shell.

8. A nanolipogel according to claim 7, which nanolipogel comprises two, three, four or more different active agents for simultaneous delivery to a cell, wherein the two, three, four or more different active agents are nucleic acids.

9. A nanolipogel according to claim 1, wherein the lipid shell is composed of one or more concentric lipid layers, optionally crosslinked, wherein the lipids can be neutral, anionic or cationic lipids at physiologic pH.

10. A nanolipogel according to claim 9, wherein the lipid is selected from the group consisting of cholesterol, phospholipids, lysolipids, lysophospholipids, and sphingolipids, and derivatives thereof.

11. A nanolipogel according to claim 9 wherein the lipid is a PEGylated derivative of a neutral, anionic, or cationic lipid.

12. A nanolipogel according to claim 1, wherein the or each nucleic acid is an mRNA or a non-integrating expression vector which can be expressed transiently in a host cell when released into the cytoplasm of the host cell.

13. A nanolipogel as claimed in claim 1, for use in a method of treating cancer or infectious disease in a subject, or for use in a method of vaccinating a subject to induce immunity against a disease or condition; which method comprises administering an effective amount of the nanolipogel to a subject in need thereof.

* * * * *